US010190955B2

(12) United States Patent
Hossain et al.

(10) Patent No.: US 10,190,955 B2
(45) Date of Patent: Jan. 29, 2019

(54) SYSTEMS AND METHODS FOR DETERMINING THE EFFECTIVE TOUGHNESS OF A MATERIAL AND FOR IMPLEMENTING MATERIALS POSSESSING IMPROVED EFFECTIVE TOUGHNESS CHARACTERISTICS

(71) Applicants: California Institute of Technology, Pasadena, CA (US); The Board of Supervisors of Louisiana State University and Agricultural and Mechanical College, Baton Rouge, LA (US)

(72) Inventors: Md. Zubaer Hossain, Newark, DE (US); Chun-Jen Hsueh, Pasadena, CA (US); Kaushik Bhattacharya, La Cañada Flintridge, CA (US); Guruswami Ravichandran, Arcadia, CA (US); Blaise Aurélien Bourdin, Baton Rouge, LA (US)

(73) Assignees: California Institute of Technology, Pasadena, CA (US); The Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 181 days.

(21) Appl. No.: 14/937,634

(22) Filed: Nov. 10, 2015

(65) Prior Publication Data

US 2016/0131564 A1 May 12, 2016

Related U.S. Application Data

(60) Provisional application No. 62/077,576, filed on Nov. 10, 2014.

(51) Int. Cl.
*G01N 3/40* (2006.01)
*G01N 3/08* (2006.01)

(52) U.S. Cl.
CPC .................. *G01N 3/40* (2013.01); *G01N 3/08* (2013.01); *G01N 2203/0017* (2013.01); *G01N 2203/0037* (2013.01); *G01N 2203/0066* (2013.01); *G01N 2203/0067* (2013.01); *G01N 2203/0218* (2013.01); *G01N 2203/0435* (2013.01)

(58) Field of Classification Search
CPC .... G01N 3/40; G01N 3/08; G01N 2203/0435; G01N 2203/0218; G01N 2203/0067; G01N 2203/0037; G01N 2203/0017; G01N 2203/0066; B32B 2307/536; B32B 2307/538; B32B 2307/558; B32B 2307/50
USPC ................................................. 428/217, 218
See application file for complete search history.

(56) References Cited

U.S. PATENT DOCUMENTS

| 5,692,414 | A  | * | 12/1997 | Gregoire | ............... F16F 15/305 74/572.12 |
| 5,773,374 | A  | * | 6/1998  | Wood     | .................. B29C 47/0021 442/399 |
| 6,878,466 | B1 | * | 4/2005  | Lange    | ..................... B32B 18/00 428/212 |
| 8,308,017 | B2 | * | 11/2012 | Schlag   | ..................... F16J 12/00 220/586 |
| 2010/0003482 | A1 | * | 1/2010 | Fukuda   | .................... C23C 16/30 428/218 |
| 2010/0121463 | A1 | * | 5/2010 | Tormala  | ................. A61L 27/446 623/23.75 |
| 2011/0132667 | A1 | * | 6/2011 | Smallman | ................ B01J 3/062 428/174 |
| 2014/0072776 | A1 | * | 3/2014 | Zalamea  | .................... C08J 5/18 428/188 |

OTHER PUBLICATIONS

Montgomery et al., "Processing and surface flaw tolerance of alumina bilayers", Journal of American Ceramic Society, Feb. 2005, vol. 88, No. 2, pp. 287-292.
Montgomery et al., "Thermoreversible gelcasting: A novel ceramic processing technique", Journal of the American Ceramic Society, May 2002, vol. 85, No. 5, pp. 1164-1168.
Mumm et al., "Interfacial debonding and sliding in brittle-matrix composites measured using an improved fiber pullout technique", Acta Metallurgica et Materialia, 1995, vol. 43, No. 3, pp. 1259-1270.
Munson et al., "TAO 2.0 Users Manual.", Argonne National Laboratory, ANL/MCS-TM-322, Jan. 2012, 76 pgs.
Nemat-Nasser et al., "Micromechanics: Overall Properties of Heterogenerous Materials.", Elsevier, North-Holland, the Netherlands, 1999, 16 pgs.
Notbohm et al., "Three-dimensional displacement and shape measurement with a diffraction-assisted grid method", Strain, 2013, vol. 49, pp. 399-408.
Ozkol et al., "Potentials of the "direct inkjet printing" method for manufacturing 3Y-TZP based dental restorations.", Journal of the European Ceramic Society, Mar. 20, 2012, vol. 32, No. 10, pp. 2193-2201.

(Continued)

*Primary Examiner* — Frank J Vineis
*Assistant Examiner* — Donald M Flores, Jr.
(74) *Attorney, Agent, or Firm* — KPPB LLP

(57) ABSTRACT

Systems and methods in accordance with embodiments of the invention determine the effective toughness of a given material, and also implement materials possessing improved effective toughness values. In one embodiment, a method of determining the effective toughness of a material includes: causing a crack to propagate through the material; where the relative constant velocity and the relative overall direction are prescribed and maintained for the duration of the propagation of the crack through the material; measuring the energy release rate of the crack as it propagates through the material; and defining the effective toughness of the material as the maximum value of the measured energy release rate.

16 Claims, 46 Drawing Sheets

(56) References Cited

OTHER PUBLICATIONS

Pallares et al., "Crack opening profile in dcdc specimen", International Journal of Fracture, vol. 156, No. 1, Mar. 27, 2009, pp. 11-20.
Pappacena et al., "Effect of pyrolyzation temperature on wood-derived carbon and silicon carbide", Journal of the European Ceramic Society, May 30, 2009, vol. 29, No. 14, pp. 3069-3077.
Pappacena et al., "Processing of wood-derived copper-silicon carbide composites via electrodeposition.", Composites Science and Technology, Jan. 4, 2010, vol. 70, No. 3, pp. 485-491.
Pappacena et al., "Thermal conductivity of porous silicon carbide derived from wood precursors.", Journal of American Ceramic Society, Mar. 31, 2007, vol. 90, No. 9, pp. 2855-2862.
Parfen'Eva et al., "Thermal conductivity of high-porosity biocarbon preforms of beech wood", Physics of the Solid State, 2010, vol. 52, No. 6, pp. 1115-1122.
Parfen'Eva et al., "Thermal conductivity of the pine-biocarbon-preform/copper composite", Physics of the Solid State, 2010, vol. 52, No. 7, pp. 1348-1355.
Pham et al., "Gradient damage models and their use to approximate brittle fracture", International Journal of Damage Mechanics, May 2011, vol. 20, pp. 618-652.
Pham et al., "The issues of the uniqueness and the stability of the homogeneous response in uniaxial tests with gradient damage models", Journal of the Mechanics and Physics of Solids, vol. 59, No. 6, Jun. 2011, pp. 1163-1190.
Ponson et al., "Crack propagation in brittle heterogeneous solids: material disorder and crack dynamics.", International Journal of Fracture, Apr. 7, 2010, vol. 162, pp. 21-31.
Pyzik et al., "Formation mechanism and microstructure development in acicular mullite ceramics by controlled decomposition of fluorotopaz", Journal of the European Ceramic Society, 2008, vol. 28, pp. 383-391.
Qiao et al., "Cleavage cracking resistance of high angle grain boundaries in Fe—3%Si alloy", Mechanics of Materials, vol. 35, No. 3-6, Mar.-Jun. 2003, pp. 313-331.
Ramanathan et al., "Quasistatic crack propagation in heterogeneous media.", Physical Review Letters, Aug. 4, 1997, vol. 79, No. 5, pp. 873-876.
Rice, "A Path Independent Integral and the Approximate Analysis of Strain Concentration by Notches and Cracks", Journal of Applied Mechanics, vol. 35, No. 2, Jun. 1968, pp. 379-386.
Rice, "First-Order Variation in Elastic Fields Due to Variation in Location of a Planar Crack Front", Journal of Applied Mechanics, vol. 52, No. 3, Sep. 1985, pp. 571-579.
Scherer et al., "Viscous sintering on a rigid substrate", Journal of the American Ceramic Society, Apr. 1985, vol. 68, No. 4, pp. 216-220.
Seitz et al., "Acrylic triblock copolymer design for thermoreversible gelcasting of ceramics: Rheological and green body properties", Journal of the American Ceramic Society, Feb. 24, 2009, vol. 92, No. 7, pp. 1519-1525.
Seitz et al., "Self-assembly and stress relaxation in acrylic triblock copolymer gels", Macromolecules, 2007, vol. 20, No. 4, pp. 1218-1226.
Shanti et al., "X-ray micro-computed tomography and tortuosity calculations of percolating pore networks", Acta Materialia, Mar. 31, 2014, vol. 71, pp. 126-135.
Srivastava et al., "Effect of inclusion density on ductile fracture toughness and roughness.", Journal of the Mechanics and Physics of Solids, 2014, vol. 63, pp. 62-79.
Stock, "Recent advances in x-ray microtomography applied to materials", International Materials Review, 2008, vol. 53, No. 3, pp. 129-181.
Suresh, "Fatigue crack deflection fracture surface-contact—micromechanical models.", Metallurgical Transactions A, Feb. 1985, vol. 16A, pp. 249-260.
Sutton et al., "Image Correlation for Shape, Motion and Deformation Measurements: basic concepts theory and applications", Springer Verlag, 2009, 332 pgs. (presented in three parts).
Takei et al., "Forbidden Directions for the Fracture of Thin Anisotropic Sheets: An Analogy with the Wulff Plot", Physical Review Letters, Apr. 5, 2013, vol. 110, No. 14, 144301-1-144301-5.
Tulliani et al., "Porous alumina and zirconia bodies obtained by a novel gel casting process.", Advances in Bioceramics and Porous Ceramics: Ceramic Engineering and Science Proceedings, Jul. 23, 2009, vol. 29, No. 7, pp. 327-338.
Wang et al., "Porous $\alpha l_2O_3$ ceramics prepared by gelcasting", Materials Research Bulletin, Dec. 1997, vol. 32, No. 12, pp. 1705-1712.
Wessel, "State of the art of the wol specimen for kic fracture toughness testing.", Engineering Fracture Mechanics, 1968, vol. 1, No. 1, pp. 77-103.
Wilkes et al., "Load partitioning in honeycomb-like silicon carbide aluminum alloy composites", Acta Materialia, Sep. 24, 2009, vol. 57, No. 20, pp. 6234-6242.
Wilkes et al., "Mechanical properties of wood-derived silicon carbide aluminum-alloy composites as a function of temperature", Journal of Materials Research, vol. 23, No. 6, Jun. 2008, pp. 1732-1743.
Wilkes et al., "X-ray micro-computed tomography of beech wood and biomorphic C, SiV and Sl/SiC composites", Philosophical Magazine, Jun. 11, 2009, vol. 89, No. 17, pp. 1373-1389.
Williams et al., "Crack Point Stress Singularities at a Bi-Material Interface", Journal of Applied Mechanics, vol. 30, No. 1, Mar. 1963, 10 pgs.
Withers et al., "Fatigue and damage in structural materials studied by x-ray tomography", Annual Review of Materials Research, May 1, 2012, vol. 42, pp. 81-103.
Xia et al., "Adhesion of Heterogeneous Thin Films II: Adhesive Heterogeneity", Journal of the Mechanics and Physics of Solids, Jun. 20, 2015, vol. 83, pp. 88-103.
Xia et al., "Adhesion of heterogeneous thin films—I: elastic heterogeneity.", Journal of the Mechanics and Physics of Solids, 2013, vol. 61, pp. 838-851.
Xia et al., "Diffraction Assisted Image Correlation: A novel method for measuring three dimensional deformation at micro-scale using two dimensional digital image correlation.", Experimental Mechanics, 2013, vol. 53, pp. 755-765.
Xia et al., "Toughening and asymmetry in peeling of heterogeneous adhesives.", Physical Review Letters, vol. 108, No. 19, May 11, 2012, pp. 196101-1-196101-5.
Xu et al., "Numerical simulations of fast crack growth in brittle solids", Journal of the Mechanics and Physics of Solids, Mar. 29, 1994, vol. 42, No. 9, pp. 1397-1434.
Zehnder, "Fracture Mechanics", Lecture Notes in Applied and Computational Mechanics, 2012, No. 62, Springer-Verlag, 235 pgs. (presented in two parts).
Zimmerman et al., "Forming textured microstructures via the gelcasting technique", Journal of the American Ceramic Society, 1997, vol. 80, No. 10, pp. 2725-2729.
Evans et al., "Toughening of ceramics by circumferential microcracking", Journal of the American Ceramic Society, Jul. 1981, vol. 64, No. 7, pp. 394-398.
Faber et al., "Crack deflection processes—I. Theory", Acta Metallurgica, 1983, vol. 31, No. 4, pp. 565-576.
Faber et al., "Crack deflection processes—II. Experiment", Acta Metallurgica, 1983, vol. 31, No. 4, pp. 577-584.
Faber et al., "Gelcasting of ceramic bodies", Ceramics and Composites Processing Methods, 2012, pp. 199-234.
Francfort et al., "Revisiting brittle fracture as an energy minimization problem", Journal of the Mechanics and Physics of Solids, vol. 46, No. 8, Aug. 1998, pp. 1319-1342.
Frenkel, "Viscous flow of crystalline bodies under the action of surface tension", Journal of Physics, Jan. 24, 1945, vol. IX, No. 5, pp. 385-391.
Freund, "Brittle crack growth modeled as the forced separation of chemical bonds within a K-field", Journal of the Mechanics and Physics of Solids, 2014, vol. 64, pp. 212-222.
Gao, "Fracture-analysis of nonhomogeneous materials via a moduli-perturbation approach.", International Journal of Solids and Structures, 1991, vol. 27, No. 13, pp. 1663-1682.

(56) References Cited

OTHER PUBLICATIONS

Gao et al., "A first-order perturbation analysis of crack trapping by arrays of obstacles.", Journal of Applied Mechanics, Dec. 1989, vol. 56, No. 4, pp. 828-836.
Griffith, "The phenomena of rupture and flow in solids", Royal Society of London Philosophical Transactions Series A, vol. 221, 1921, pp. 163-198.
Gurtin et al., "Configurational forces and the basic laws for crack propagation", Journal of the Mechanics and Physics of Solids, Jan. 9, 1996, vol. 44, No. 6, pp. 905-927.
He et al., "Crack deflection at an interface between dissimilar elastic materials", International Journal of Solids and Structures, vol. 25, No. 9, 1989, pp. 1053-1067.
Holland et al., "Ideal brittle fracture of silicon studied with molecular dynamics.", Physical Review Letters, vol. 80, No. 4, Jan. 26, 1998, pp. 746-749.
Hossain et al., "Effective toughness of heterogeneous solids", Journal of Mechanics and Physics of Solids, Jun. 20, 2014, vol. 71, pp. 15-32.
Hsiung et al., "Impact of doping on the mechanical behavior of acicular mullite.", Journal of the European Ceramic Society, Mar. 9, 2013, vol. 33, pp. 1955-1965.
Hsiung et al., "Microstructure and mechanical properties of acicular mullite.", Journal of the European Ceramic Society, 2013, vol. 33, No. 3, pp. 503-513.
Hsueh et al., "Homogenization and Path Independence of the J-integral in Heterogeneous Materials", Journal of Applied Mechanics, Oct. 2016, vol. 83, pp. 101012-1-101012-3.
Hsueh et al., "Measuring the effective fracture toughness of heterogeneous materials", Experimental Mechanics, 2016, pp. 151-155.
Hutchinson et al., "Mixed Mode Cracking in Layered Materials.", Advances in Applied Mechanics, 1991, vol. 29, pp. 63-191.
Irwin, "Analysis of stresses and strains near the end of a crack traversing a plate.", Journal of Applied Mechanics, Sep. 1957, pp. 361-364.
Janssen, "Specimen for fracture mechanics studies on glass", In Proceedings of the 10th International Congress on Glass, 1974, 10 pgs., Jul. 1974.
Johnson et al., "Catalytic graphitization of three-dimensional wood-derived porous scaffolds", Journal of Materials Research, vol. 26, No. 1, Jan. 2011, pp. 18-25.
Johnson et al., "Thermal conductivity of wood-derived graphite and copper-graphite composites produced via electrodeposition.", Composites Part A, Jun. 26, 2013, vol. 53. pp. 182-189.
Johnson et al., "Wood-derived copper-graphite composites produced via additive-assisted electrodeposition", Composites Science and Technology, Oct. 5, 2013, vol. 89, pp. 61-68.
Kardashev et al, "Young's modulus and internal friction in porous biocarbon white pine wood precursors", Physics of the Solid State, Apr. 2, 2009, vol. 51, No. 12, pp. 2320-2325.
Kardashev et al., "Elasticity and inelasticity of the SiC/Al—13Si—9Mg biomorphic metal ceramics", Physics of the Solid State, Feb. 11, 2008, vol. 50, No. 10, pp. 1807-1812.
Kaul et al., "Nanoindentation analysis of the elastic properties of porous SiC derived from wood", Scripta Materialia, Jan. 19, 2008, vol. 58, No. 10, pp. 886-889.
Kermode et al., "Low-speed fracture instabilities in a brittle crystal", Nature, Oct. 2008, vol. 455, pp. 1224-1227.
Knowles, "A note on the energy-release rate in quasi-static elastic crack-propagation.", SIAM Journal on Applied Mathematics, vol. 41, No. 3, Dec. 1981, pp. 401-412.
Kovalchick et al., "An Experimental Investigation of the Stability of Peeling for Adhesive Tape", Mechanics of Materials, Aug. 9, 2013, vol. 66, pp. 69-78.
Kovalchick et al., "Rate Dependent Adhesion Energy and Nonsteady Peeling of Inextensible Tapes", Journal of Applied Mechanics, vol. 81, No. 4, pp. 041016-1-041016-6, Apr. 2014.

Kumar et al., "Statistical physics models for nacre fracture simulation.", Physical Review E, Oct. 19, 2005, vol. 72, No. 4, pp. 041919-1-041919-9.
Lejeune et al., "Ink-jet printing of ceramic micro-pillar arrays.", Journal of the European Ceramic Society, vol. 29, No. 5, Mar. 2009, pp. 905-911.
Leon Baldelli et al., "Fracture and debonding of a thin film on a stiff substrate: analytical and numerical solutions of a 1d variational model.", Continuum Mechanics and Thermodynamics, vol. 25, No. 2-4, 2013, pp. 243-268.
Leon Baldelli et al., "On the asymptotic derivation of Winkler-type energies from 3D elasticity", Journal of Elasticity, in press, arXiv:1410.0629 Oct. 2, 2014, pp. 1-21.
Lipton et al., "Inverse homogenization and design of microstructure for pointwise stress control.", Quarterly of Applied Mathematics, Feb. 2006, vol. 59, No. 1, pp. 139-161.
Lipton et al., "Optimal design of composite structures for strength and stiffness: an inverse homogenization approach", Structural and Multidisciplinary Optimization, Jan. 20, 2007, vol. 33, No. 4, pp. 351-362.
Lombardi et al., "A modified gencasting procedure to prepare alumina porous components: Process optimization and preliminary mechanical tests", Ceramic Engineering and Science Proceedings, 2008, vol. 29, pp. 287-297.
Malvadkar et al., "An engineered anisotropic nanofilm with unidirectional wetting properties", Nature Materials, Dec. 2010, vol. 9, No. 12, pp. 1023-1028.
Mathieu et al., "Identification of a crack propagation law by digital image correlation", International Journal of Fatigue, vol. 36, No. 1, Mar. 2012, pp. 146-154.
Maurini et al., "Crack patterns obtained by unidirectional drying of a colloidal suspension in a capillary tube: experiments and numerical simulations using a two-dimensional variational approach.", International Journal of Fracture, Nov. 2013, vol. 184, No. 1, pp. 75-91.
Menig et al., "Quasi-static and dynamic mechanical response of *Haliotis rufescens* (abalone) shells", Acta Materialia, 2000, vol. 48, pp. 2283-2398.
Mesgarnejad et al., "A variational approach to the fracture of brittle thin films under out of plane loading", Journal of the Mechanics and Physics of Solids, May 22, 2013. vol. 61, pp. 2360-2379.
Mesgarnejad et al., "Validation simulations for the variational approach to fracture", Computer Methods in Applied Mechanics and Engineering, 2015, vol. 290, pp. 420-437.
Montgomery et al., "A thermoreversible gelcasting technique for ceramic laminates", Scripta Materialia, 2003, vol. 48, No. 6, pp. 785-789.
Abeyaratne et al., "Kinetics of materials with wiggly energies: theory and application to the evolution of twinning microstructures in Cu—Al—Ni shape memory alloy.", Philosophical Magazine A, 1996, vol. 73, No. 2, pp. 457-497.
Alali et al., "Optimal lower bounds on local stress inside random media", SIAM Journal on Applied Mathematics, vol. 70, No. 4, 2009, 1260-1282.
Allaire et al., "Shape optimization by homogenization method", Springer Verlag, 2002, 44 pgs.
Allaire et al., "Minimum stress optimal design with the level set method", Engineering Analysis with Boundary Elements, Jun. 2, 2008, vol. 32, No. 11, pp. 909-918.
Allaire et al., "Topology optimization for minimum stress design with the homogenization method", Structural and Multidisciplinary Optimization, vol. 28, No. 2, Aug. 4, 2004, pp. 87-98.
Ambrosio et al., "Approximation of functional depending on jumps by elliptic functional via t-convergence.", Communications on Pure and Applied Mathematics, vol. 43, No. 8, Dec. 1990, pp. 990-1036.
Atkinson, "On the stress intensity factors associated with cracks interacting with an interface between two elastic media." International Journal of Engineering Science, May 1975. vol. 13, No. 5, pp. 489-504.
Avril et al., "Grid method: application to the characterization of cracks", Experimental Mechanics, vol. 44, No. 1, Feb. 24, 2003, pp. 37-43.

(56) References Cited

OTHER PUBLICATIONS

Badulescu et al., "Investigation of the grid method for accurate in-plane strain measurement", Measurement Science and Technology, Jul. 21, 2009, vol. 20, No. 9, 095102, 17 pgs.
Balay et al., "Efficient management of parallelism in object oriented numerical software libraries.", E. Arge et al., editors, Modern Software Tools in Scientific Computing, 1997, Birkhauser Press, pp. 163-202.
Balay et al., "PETSc Web page", Accessed via the internet URL: http://www.mcs.anl.gov/petsc, Accessed Feb. 17, 2016.
Barthelat et al., "An experimental investigation of deformation and fracture of nacre-mother of pearl.", Experimental Mechanics, vol. 47, No. 3, Mar. 2, 2007, pp. 311-324.
Begley et al., "Micromechanical models to guide the development of synthetic 'brick and mortar' composites", Journal of the Mechanical and Physics of Solids, Mar. 10, 2012, vol. 60, No. 8, pp. 1545-1560.
Belytschko et al., "Dynamic crack propagation based on loss of hyperbolicity and a new discontinuous enrichment.", International Journal for Numerical Methods in Engineering, Jul. 3, 2003, vol. 58, No. 12, pp. 1873-1905.
Bendsøe et al., "Topology Optimization: Theory, Methods and Applications", Springer, 2nd edition, 2003, 393 pgs. (presented in two parts).
Bhattacharya, "Phase boundary propagation in a heterogeneous body.", Royal Society of London Proceedings Series A, 1999, vol. 455, pp. 757-766.
Bluet et al., "Probing the structure of heterogeneous diluted materials by diffraction tomography", Nature Materials, Jun. 2008, vol. 7, No. 6, Apr. 20, 2008, pp. 468-472.
Bonamy et al., "Crackling Dynamics in Material Failure as the Signature of a Self-Organized Dynamic Phase Transition", Physical Review Letters, vol. 101, No. 4, 045501, Mar. 3, 2008, 5 pgs.
Bonamy et al., "Scaling Exponents for Fracture Surfaces in Homogeneous Glass and Glassy Ceramics," Physical Review Letters, vol. 97, No. 13, 135504, Sep. 2006, 5 pgs.
Bouchaud, "Scaling properties of cracks", Journal of Physics: Condensed Matter, 1997, vol. 9, No. 21, pp. 4319-4344.
Bourdin et al., "A variational approach to the numerical simulation of hydraulic fracturing.", In Proceedings of the 2012 SPE Annual Technical Conference and Exhibition, vol. SPE 159154, 2012, 9 pgs.
Bourdin et al., "Morphogenesis and propagation of complex cracks induced by thermal shocks.", Physical Review Letters, Jan. 10, 2014, vol. 112, No. 1, pp. 014301-1-014301-5.
Bourdin et al., "Numerical experiments in revisited brittle fracture.", Journal of the Mechanics and Physics of Solids, 2000, vol. 48, No. 4, pp. 797-826.
Bourdin et al., "Numerical simulation of reservoir stimulation—a variational approach.", Proceedings of the 37th Stanford Geothermal Workshop, Stanford University, CA, Jan. 31, Feb. 2, 2011, 6 pgs.
Bourdin et al., "Secondary thermal cracks in EGS: a variational approach", GRC Transactions, 2010, vol. 34, pp. 319-322.
Bourdin et al., "The variational approach to fracture", Journal of Elasticity, Mar. 15, 2008, vol. 91, No. 1., pp. 5-148.
Bower et al, "A Three-dimensional analysis of crack trapping and bridging by tough particles.", Journal of the Mechanics and Physics of Solids, 1991, vol. 39, No. 6, pp. 815-858.
Bruhwiler et al., "The wedge splitting test: A method of performing stable fracture mechanics tests.", Engineering Fracture Mechanics, Dec. 1990, vol. 35, No. 1-3, Dec. 1990, pp. 117-125.
Bueckner, "A novel principle for the computation of stress intensity factors.", Zeitschrift fuer Angewandte Mathematik & Mechanik, 1970, vol. 50, No. 9, pp. 529-546.
Burger et al., "Phase-field relaxation of topology optimization with local stress constraints.", SIAM Journal on Control and Optimization, Apr. 16, 2006, vol. 45, No. 4, pp. 1447-1466.
Camacho et al., "Computational modelling of impact damage in brittle materials", International Journal of Solids and Structures, 1996, vol. 33, No. 20-22, pp. 2899-2938.
Cazzato et al., "Fracture energy of glass-alumina interfaces via the biomaterial bend test", Journal of American Ceramic Society, 1997, vol. 80, No. 1, pp. 181-188.
Cherepanov, "Crack propagation in continuous media.", Journal of Applied Mathematics and Mechanics, Jan. 24, 1967, vol. 31, No. 3, pp. 503-512.
Cherkaeva et al., "Optimal design for uncertain loading conditions.", In Homogenization (edited by Berdichevsky et al.), 1999, pp. 1-16.
Childers et al., "Interfacial frictional stresses and fracture toughness in biomorphic graphite/copper interfaces", Material Letters, Mar. 14, 2016, vol. 175, pp. 106-109.
Childers et al., "Modeling macro-sized, high aspect ratio through-hole filling by multi-component additive assisted copper electrodeposition.", Journal of the Electrochemical Society, vol. 160, No. 12, Aug. 29, 2013, D3093-D3102.
Christ et al., "Fiber reinforcement during 3d printing.", Materials Letters, vol. 139, Jan. 2015, pp. 165-168.
Chukwudi et al., A variational approach to the modeling and numerical simulation of hydraulic fracturing under in-situ stresses, Feb. 11-13, 2013, In Proceedings of the 38th Workshop on Geothermal Reservoir Engineering Stanford University, Stanford, CA, 10 pgs.
Cosijns et al., "Porous hydroxyapatite tablets as carriers for low-dosed drugs.", European Journal of Pharmaceutics and Biopharmaceutics, Feb. 28, 2007, vol. 67, No. 2, pp. 498-506.
Cox et al., "In quest of virtual tests for structural composites.", Science, vol. 314, No. 5802, Nov. 17, 2006, pp. 1102-1107.
Currey et al., "The mechanical-behavior of some molluscan hard tissues.", Journal of Zoology, 1974, vol. 173, No. 3, pp. 395-406.
Del Piero, "A variational approach to fracture and other inelastic phenomena", Journal of Elasticity, May 9, 2013, vol. 112, No. 1, pp. 3-77.
Dirr et al., "Pinning and de-pinning phenomena in front of propagation in heterogeneous media.", Interfaces and Free Boundaries, vol. 8, No. 1, 2006, pp. 79-109.
Dondl et al., "Effective behavior of an interface propagating through a periodic elastic medium", Jun. 13, 2012.
Duysinx et al., "Topology optimization of continuum structures with local stress constraints", International Journal for Numerical Methods in Engineering, Mar. 31, 1998, vol. 43, No. 8, pp. 1453-1478.
Evans et al., "Model for the robust mechanical behavior of nacre.", Journal of Materials Research, vol. 16, No. 9, Sep. 2001, pp. 2475-2484.
Espinosa et al., "Tablet-level origin of toughening in abalone shells and translation to synthetic composite materials", Nature Communications, Feb. 1, 2011, vol. 2, No. 173, 9 pgs.
Hestenes et al., "Methods of Conjugate Gradients for Solving Linear Systems", Journal of Research of the National Bureau of Standards, Dec. 1952, vol. 49, No. 6, pp. 409-436.
Kierfield et al., "Slow crack propagation in heterogeneous materials", Physical Review Letters, May 2006, vol. 96, 175502, 4 pgs.
Launey et al., "On the mechanic origins of toughness in bone", Annual Review of Materials Research, Feb. 26, 2010, vol. 40, pp. 25-53.
Li et al., "Prediction of fracture toughness of ceramic composites as function of microstructure: I. numerical simulations", Journal of the Mechanics and Physics of Solids, Feb. 2013, vol. 61, No. 2, pp. 472-488.
Li et al., "Prediction of fracture toughness of ceramic composites as function of microstructure: II. analytical model", Journal of the Mechanics and Physics of Solids, 2013, vol. 61, No. 2, pp. 489-503.
Murali et al., "Atomic scale fluctuations govern brittle fracture and cavitation behavior in metallic glasses", Physical Review Letters, Nov. 2011, vol. 107, 215501, 5 pgs.
Nukala et al., "Statistical physics models for nacre fracture simulation", Physical Review E., Jan. 2005, vol. 72, No. 4, 041919, 9 pgs.

(56) References Cited

OTHER PUBLICATIONS

Shao et al., "Discontinuous crack-bridging model for fracture toughness analysis of nacre", Journal of the Mechanics and Physics of Solids, Apr. 27, 2012, vol. 60, No. 8, pp. 1400-1419, 20 pgs.

* cited by examiner

Diverging

Converging inclusion y3: Path *abcd*   y4: Path *efgh*   y5: Path *ijkl*

SYSTEMS AND METHODS FOR DETERMINING THE EFFECTIVE TOUGHNESS OF A MATERIAL AND FOR IMPLEMENTING MATERIALS POSSESSING IMPROVED EFFECTIVE TOUGHNESS CHARACTERISTICS

CROSS-REFERENCE TO RELATED APPLICATIONS

This application claims priority to U.S. provisional patent application Ser. No. 62/077,576 entitled "Enhancement and Asymmetry of Fracture Toughness using Elasto-Geometric Heterogeneity," filed on Nov. 10, 2014, the disclosure of which is incorporated by reference herein in its entirety.

STATEMENT OF FEDERAL FUNDING

This invention was made with government support under Grant No. CMMI1201102 awarded by the National Institutes of Health. The government has certain rights in the invention.

FIELD OF THE INVENTION

The present invention generally relates to determining the effective toughness of materials and also implementing materials having improved fracture mechanics.

BACKGROUND

The 'fracture toughness' of a material is a property that characterizes the respective material's ability to resist fracture assuming the presence of a thin crack. It is typically determined from the 'stress intensity factor' K at which a thin crack in the material begins to grow. The 'stress intensity factor' K is generally meant to characterize the stress state near the tip of a crack (e.g. one caused by a remote load or residual stresses). Notably, the stress intensity factor can be a function of the loading that the crack is subjected to. Conventionally: 'mode I' loading references a normal tensile stress perpendicular to the crack; 'mode II' loading references an in-plane shear loading; and 'mode III' references out-of-plane shearing of the crack. Conventionally, as alluded to above, the fracture toughness of a material is often gleaned from the stress intensity factor at which a thin crack in the material being subjected to mode I loading begins to grow, i.e. its $K_{Ic}$ value. $K_{Ic}$ is typically determined experimentally and generally has the units of stress multiplied by the square root of distance.

Relatedly, the fracture toughness can also be expressed in terms of the energy per unit fracture surface area. This is typically indicated by the 'J-integral.' The J-integral can also be thought of as the energy required to grow a thin crack.

The fracture toughness of a material has conventionally been determined in a number of ways. For instance, 'Charpy impact tests' are often used to determine the amount of energy that can be absorbed during fracture, and this absorbed energy can be indicative of the overall fracture toughness of a material. Active Standard ASTM E23 discusses methods for implementing Charpy impact tests.

Similarly, 'crack resistance curves' or 'R-curves' are also conventionally derived and used to characterize the toughness of a material. R-curves illustrate a material's resistance to crack extension as a function of crack extension. Active Standard ASTM E561 discusses a standard test method for K-R curve determination.

SUMMARY OF THE INVENTION

Systems and methods in accordance with embodiments of the invention determine the effective toughness of a given material, and also implement materials possessing improved effective toughness values. In one embodiment, a method of determining the effective toughness of a material includes: causing a crack to propagate through the material; where the relative constant velocity and the relative overall direction are prescribed and maintained for the duration of the propagation of the crack through the material; measuring the energy release rate of the crack as it propagates through the material; and defining the effective toughness of the material as the maximum value of the measured energy release rate.

In another embodiment, the relative constant velocity and the relative overall direction are assessed based on average values taken over a plurality of internal length scale units.

In yet another embodiment, the relative constant velocity and the relative overall direction are assessed based on average values taken over between approximately five and approximately fifteen internal length scale units.

In still another embodiment, average velocity values that deviate by within approximately 15% are determined to be relatively constant.

In still yet another embodiment, the relative constant velocity and the relative overall direction are assessed based on average values taken over predetermined time intervals, each of which being greater than approximately 3 seconds in length.

In a further embodiment, the displacement field conforms to the relationship: $u(x, y, t) = U(x-vt, y)$ on $\partial \Omega$; where: u is the displacement field; U is the mode-I crack opening displacement; $\Omega$ is the domain; v is velocity; and x and y regard positional information.

In a yet further embodiment, the displacement field conforms to the relationship:

$$u(x, y, t) = \left( \frac{A}{2} \left( 1 - \tanh \frac{\overset{0}{x - vt}}{d} \right) \sin(y) \right);$$

where: u is the displacement field; v is velocity; x and y regard positional information; and A and d are constants.

In a still further embodiment, the material is a heterogeneous material.

In another embodiment, a material includes: a first region characterized by a first elastic modulus; and a second region characterized by a second elastic modulus; where: the first elastic modulus is different than the second elastic modulus; and the effective toughness of the material is thereby greater than it would be if it the material was entirely characterized only by the first elastic modulus or else entirely characterized only by the second elastic modulus.

In yet another embodiment, the material is characterized by a plurality of adjacently-disposed striped regions, where the elastic modulus of each of the stripes alternates between the first elastic modulus and the second elastic modulus.

In still another embodiment, the elastic modulus varies sinusoidally along a first direction of the material.

In still yet another embodiment, the elastic modulus varies in accordance with the relation:

$$E(x) = E_0 - E_A \cos \frac{2\pi x}{\lambda};$$

where: $E_0$ is the maximum elastic modulus; $E_A$ is the amplitude; $\lambda$ is the desired wavelength; and x regards positional information.

In a further embodiment, a material includes: a plurality of regions, each of which being characterized by a different elastic modulus; where the elastic moduli amongst the plurality of regions are asymmetrically distributed so as to give rise to asymmetric effective toughness of the material.

In a yet further embodiment, the regions are characterized by striped geometries.

In a still further embodiment, the material is characterized by a periodic, but asymmetric, distribution of elastic moduli.

In another embodiment, a material includes: inclusions; where the presence of the inclusions causes the material to possess asymmetric effective toughness.

In yet another embodiment, the inclusions are characterized by asymmetric geometries, and thereby cause the material to possess asymmetric effective toughness.

In still another embodiment, the inclusions are characterized by funnel-shaped geometries, and thereby cause the material to possess asymmetric effective toughness.

In still yet another embodiment, the inclusions are disposed within the material in an asymmetric arrangement, and thereby cause the material to possess asymmetric effective toughness.

In a further embodiment, the inclusions are disposed within the material in an arrow-shaped pattern, and thereby cause the material to possess asymmetric effective toughness.

DETAILED DESCRIPTION

Figure 1A:
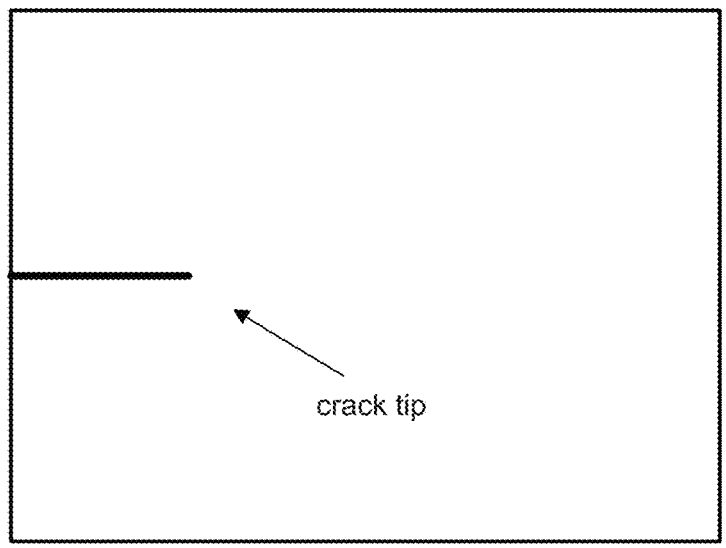
FIGS. 1A-1D illustrate data associated with assessing the effective toughness of a homogenous material in accordance with certain embodiments of the invention.

Turning now to the drawings, systems and methods for determining the effective toughness of materials, and also implementing materials having improved fracture characteristics are illustrated. Fracture mechanics, starting with the work of Alan Arnold Griffith, is a grand success of the past century with the development of a profound theory that can describe crack propagation in complex macroscopic situations. Much of the work of Griffith is embodied in "The phenomena of rupture and flow in solids," *Phil. Trans. R. Soc. Lond.* 221, 193-198, the disclosure of which is hereby incorporated by reference in its entirety. However, this theory requires an empirical parameter—the fracture toughness. How this parameter arises, or how it changes, or even what it means in the microstructural hierarchy of materials has remained incompletely understood.

Over the last few decades a number of composite structures have been developed, especially in the context of ceramics, where microstructural features have been exploited to enhance their respective toughness characteristics. Consequently, there is an extensive literature on the fracture toughness of composite materials: e.g., Bower, A., Ortiz, M., 1991, "A 3-dimensional analysis of crack trapping and bridging by tough particles," *J. Mech. Phys. Solids*, 39, 815-858; Cox, B., Yang, Q., 2006, "In quest of virtual tests for structural composites," *Science* 314, 1102-1107; Evans, A. G., Faber, K. T., 1981, "Toughening of ceramics by circumferential microcracking," *J. Am. Ceram. Soc.* 64, 394-398; Faber, K. T., Evans, A. G., 1983, "Crack deflection processes," *ActaMetall. Mater.* 31, 565-584; Gao, H., Rice, J., 1989, "A first-order perturbation analysis of crack trapping by arrays of obstacles," *J. Appl. Mech.* 56, 828-836.; Hutchinson, J., Suo, Z., 1992, "Mixed-mode cracking in layered materials," *Adv. Appl. Mech.* 29 (January), 63-191; Suresh, S., 1985, "Fatigue crack deflection and fracture surface-contact—micromechanical models," *Metall. Trans.* A16, 249-260. These above-cited disclosures are hereby incorporated by reference in their entirety. The mentioned composites also motivated systematic mathematical formulation of the change of stress intensity with perturbations in the crack front and modulus; see e.g., Gao, H., 1991, "Fracture-analysis of nonhomogeneous materials via a moduli-perturbation approach," *Int. J. Solids Struct.* 27, 1663-1682; and Rice, J., 1985, "1st-order variation in elastic fields due to variation in location of a planar crack front." *J. Appl. Mech.* 52, 571-579. These above-cited papers are hereby incorporated by reference in their entirety. However, the cited works are generally limited to particular microstructures of relevance to composites.

The relation between random microstructures and observable features including morphology of crack surfaces and rate dependence has received much attention with the discovery of some universal scaling laws; see e.g. Bonamy, D., Ponson, L., Prades, S., Bouchaud, E., Guillot, C., 2006, "Scaling exponents for fracture surfaces inhomogeneous glass and glassy ceramics," *Phys. Rev. Lett.* 97, 135504; Bouchaud, E., 1997, "Scaling properties of cracks," *J. Phys. Condens. Mat.* 9, 4319-4344; Ponson, L., Bonamy, D., 2010, "Crack propagation in brittle heterogeneous solids: material disorder and crack dynamics," *Int. J. Fract.* 162, 21-31; and Ramanathan, S., Ertas, D., Fisher, D. S., 1997, "Quasi static crack propagation in heterogeneous media," *Phys. Rev. Lett.* 79, 873-876. These above-cited disclosures are hereby incorporated by reference in their entirety. However, these are limited to random microstructures and use statistical mechanical methods that use randomness in an essential manner. Furthermore, many of them use perturbative methods assuming small contrast. Recently, Srivastava et al. (2014) have studied the role of random inclusions on both toughness and roughness in ductile fracture; see e.g. Srivastava, A., Ponson, L., Osovski, S., Bouchaud, E., Needleman, A., 2014, "Effect of inclusion density on ductile fracture toughness and roughness," *J. Mech. Phys. Solids* 63, 62-79. The above-cited disclosure to Srivastava et al. is hereby incorporated by reference in its entirety.

Nature has exploited microstructure to enhance toughness of nacre and other shells. Various researches have studied the underlying mechanisms and also sought to mimic the microstructure in bio-inspired designs; see e.g. Barthelat, F., Espinosa, H. D., 2007, "An experimental investigation of deformation and fracture of nacre-mother of pearl," *Exp. Mech.* 47, 311-324.; Currey, J. D., Taylor, J. D., 1974, Mechanical-behavior of some molluscan hard tissues," *J. Zool.* 173, 395-406; Evans, A. G., Suo, Z., Wang, R. Z., Aksay, I. A., He, M. Y., Hutchinson, J. W., 2001, "Model for the robust mechanical behavior of nacre," *J. Mater. Res.* 16, 2475-2484.; Menig, R., Meyers, M. H., Meyers, M. A., Vecchio, K. S., 2000, "Quasi-static and dynamic mechanical response of Haliotisrufescens (abalone) shells," *Acta Mater.* 48, 2383-2398.; Nukala, P. K. V. V., Simunovic, S., 2005, "Statistical physics models for nacre fracture simulation," *Phys. Rev. E*72, 041919.; and Begley, M. R., Philips, N. R., Compton, B. G., Wilbrink, D. V., Ritchie, R. O., Utz, M., 2012, "Micromechanical models to guide the development of synthetic 'brick and mortar' composites," *J. Mech. Phys. Solids* 60, 1545-1560. These above-cited disclosures are hereby incorporated by reference in their entirety. Once again, this work is generally limited to particular classes of biologically relevant microstructures.

Through all of these works, there is an understanding that fracture toughness can be increased in a heterogeneous material by various mechanisms including crack deflection and meandering, zone shielding (through transformation toughening, microcrack toughening, crack-field void formation) and contact shielding (through wedging, bridging, sliding, plasticity induced crack closure). Nevertheless, a comprehensive theory that describes the effective toughness of a heterogeneous medium is still to emerge.

There is a well-developed theory that describes the overall or effective properties of heterogeneous materials in the context of elasticity, electrostatics, magnetism and other properties that are characterized by variational principles; see e.g., Milton, G., 2002, *The Theory of Composites*, Cambridge University Press, Cambridge, England; and Nemat-Nasser, S., Hori, M., 1999, *Micromechanics: Overall Properties of Heterogeneous Materials*, Elsevier Science, North-Holland, The Netherlands. The above-cited disclosures are hereby incorporated by reference in their entirety. Many of these methods have been extended to dissipative processes like plasticity in the context of deformation theory or incremental update where one has a variational principle. Unfortunately, such a theoretical development has remained missing in the case of fracture and other free-boundary/free-discontinuity problems. The key difficulty has been that bounds on energy do not necessarily imply bounds on the derivatives of energy: a small bump in the energy landscape may become a very large bump in the forcing leading to changed behavior.

This is more than a theoretical difficulty, but points to the fact that in time-dependent or evolution problems, the effective macroscopic behavior can be very different from the underlying microscopic relations. In one dimension, it is known that a microscopically viscous evolution law can lead to a macroscopically stick-slip behavior; see e.g., Abeyaratne, R., Chu, C., James, R. D., 1996, "Kinetics of materials with wiggly energies: theory and application to the evolution of twinning microstructures in a Cu—Al—Ni shape memory alloy," *Philos. Mag.* A73, 457-497; and Bhattacharya, K., 1999, "Phase boundary propagation in a heterogeneous body," *Philos. R. Soc. Lond.* A455, 757-766. These above-cited disclosures are hereby incorporated by reference in their entirety. Similar results have also been established for quasilinear free-boundary problems; see e.g. Dirr, N., Yip, N. K., 2006, "Pinning and de-pinning phenomena in front propagation in heterogeneous media," *Interface Free Bound*, 8, 79-109; and Dondl, P., Bhattacharya, K., 2015. "Effective behavior of an interface propagating through aperiodic elastic medium," to appear in *Interfaces and Free Boundaries*. These above-cited disclosures are hereby incorporated by reference in their entirety. Recently, Xia et al. (2012, 2013) explored the role of heterogeneity in the mechanics of peeling adhesive tape; see e.g., Xia, S., Ponson, L., Ravichandran, G., Bhattacharya, K., 2012, "Toughening and asymmetry in peeling of heterogeneous adhesives," *Phys. Rev. Lett.* 108, 196101; and Xia, S. M., Ponson, L., Ravichandran, G., Bhattacharya, K., 2013, "Adhesion of heterogeneous thin films—I elastic heterogeneity, *J. Mech. Phys. Solids*, 61, 838-851. These disclosures are hereby incorporated by reference in their entirety. They showed that patterning the elastic stiffness of the tape (with no change in the actual adhesive) can lead to dramatically enhanced and possibly anisotropic and asymmetric resistance to peeling. All of these point to interesting phenomena in fracture.

More fundamentally, note that in the past, the fracture toughness of a material has largely been determined empirically (e.g. via measuring its $K_{Ic}$ value); importantly, the results of such tests are often context dependent. For example, a material can demonstrate different critical stress intensity factors based on its geometry and how it is being loaded. In this sense, the measured toughness values are often a function of the manner in which the sample material is being tested rather than a true measure of a material's intrinsic toughness value.

Against this backdrop, the instant application discloses a robust definition of the 'effective toughness' of a material, the 'effective toughness' being independent of the macroscopic loading context and with no a priori assumption or restriction about the evolution of the crack set at the microscopic scale, as well as systems and methods for computing this effective toughness. Note that the disclosed systems and methods can be used to determine the effective toughness of a heterogeneous media—the disclosed systems and methods are not restrained to characterizing homogeneous media. The effective toughness is meant to characterize a material's inherent resistance to the propagation of a crack; importantly, the computed effective toughness is meant to be an intrinsic material property that is independent of any applied boundary condition. In this way, the 'effective toughness' can serve as a more robust characterization of the toughness of a material.

The instant application further discloses using this notion of 'effective toughness' to implement materials having tailored fracture characteristics. For instance, in many embodiments, the notion of 'effective toughness' is used to implement materials being characterized by elastic heterogeneity, and thereby having improved effective toughness. In numerous embodiments, materials are implemented having asymmetric fracture characteristics. For example, in several embodiments, materials are implemented that include asymmetric elastic characteristics, and thereby have asymmetric fracture characteristics. In a number of embodiments, materials are implemented that include inclusions that give rise to asymmetric fracture characteristics. For instance, in a number of embodiments, materials are implemented that include a periodic array of inclusions that are asymmetric in geometry, and thereby give rise to asymmetric fracture characteristics. In several embodiments, materials are implemented that include inclusions patterned in an asymmetric formation, and thereby give rise to asymmetric fracture characteristics. The development and implementation of materials having asymmetric fracture characteristics can have profound implications, as this can allow for the custom tailoring of fracture situations.

Much of the discussion that follows has been described in "Effective toughness of heterogeneous media," *Journal of the Mechanics and Physics of Solids* 71, (2014), 15-32, to the inventors of the instant application. The disclosure of this above-cited reference is herein incorporated by reference in its entirety.

A discussion of the notion of 'effective toughness' now follows.

Effective Toughness

The notion of fracture toughness in a homogeneous body goes back to the work of A. A. Griffith (his seminal work is discussed and cited above). Consider a body subjected to a certain loading with a smooth crack evolving smoothly with time. An elastic energy release rate or driving force acting on the crack front as the negative of the rate of change of the elastic potential energy U with crack length a can be defined. It can be stated that the crack continues to grow if this energy release rate is equal to a critical value $G_c$:

$$G_c = -\frac{\partial U}{\partial a} \quad (1)$$

The energy release rate is given by the celebrated path-independent J-integral $$J = \int_c \hat{t} \cdot C \hat{n} \, dl \quad (2)$$

where $\hat{n}$ is the outward normal to the contour $\hat{t}$ is the tangent to the crack tip and $$C = \varphi I - (\nabla u)^T \sigma \quad (3)$$

is the Eshelby's energy-momentum tensor or the configurational stress tensor, $$\varphi = \frac{1}{2} e(u).$$

$\mathbb{C} e$ (u) the elastic energy density, u is the displacement, e $(u) = \frac{1}{2}(\nabla u + \nabla u^T)$ the strain and $\sigma$ the Cauchy stress (in the linear elastic setting); see e.g., Cherepanov, G. P., 1967, "Crack propagation in continuous media," *J. Appl. Math. Mech.*, 31, 503-512; and Rice, J. R., 1968, "A path independent integral and the approximate analysis of strain concentration by notches and cracks," *J. Appl. Mech.*, 35, 379-386. These above-cited disclosures are hereby-incorporated by reference in their entirety. In a homogenous material, the J-integral is generally path-independent since the energy-moment tensor is divergence-free. One can also relate the J-integral to rate of dissipation of energy and the configurational force balance; see e.g., Knowles, J. K., 1981, "A note on the energy-release rate in quasi-static elastic crack-propagation," *SIAM J. Appl. Math* 41, 401-412; and Gurtin, M. E., Podio-Guidugli, P., 1996, "Configurational forces and the basic laws for crack propagation," *J. Mech. Phys. Solids*, 44, 905-927. These above-cited disclosures are incorporated by reference in their entirety.

Finally, it is conventional in linear elastic fracture mechanics to perform an asymptotic expansion of the elastic field near the crack tip. For a Mode-I crack (where the crack is opened normal to the crack surface), the displacement fields are given as $$U_x = \frac{K_I}{2\mu}\sqrt{\frac{r}{2\pi}}\,(\kappa - \cos\theta)\cos\frac{\theta}{2} \quad (4)$$

$$U_y = \frac{K_I}{2\mu}\sqrt{\frac{r}{2\pi}}\,(\kappa - \cos\theta)\sin\frac{\theta}{2}$$

$K_I$ is called the stress-intensity factor, $\kappa=(3-v)/(1+v)$, $\mu=E/2(1+v)$, and $(r, \theta)$ are polar coordinates emanating from the crack tip; see e.g., Zehnder, A. T., 2012, "Fracture Mechanics In: Lecture Notes" in *Applied and Computational Mechanics*, No. 62, Springer-Verlag. The above-cited disclosure is hereby incorporated by reference in its entirety. It is conventional to describe the crack-propagation criterion as $K_I \geq K_{Ic}$ where $K_{Ic}$ is known as the fracture toughness of the material. It is entirely equivalent to the considerations above, due to Irwin's relation (Irwin, 1957), $$J = \frac{K_I^2}{E}. \quad (5)$$

Irwin's relation is given in: Irwin, G. R., 1957, "Analysis of stresses and strains near the end of a crack traversing a plate," *J. Appl. Mech.* 24, 361-364. This above-cited disclosure is hereby incorporated by reference in its entirety. With some abuse of terminology, $$G_c = \frac{K_{Ic}^2}{E}$$

can be referred to as the toughness of the material.

The conditions above generally speak to the propagation of an existing crack. An additional criterion is necessary for nucleation of cracks. A general formulation of this remains a topic of active research, but is often specified as a length-scale that represents the size of a critical crack nucleus (See e.g., the work of Zehnder, discussed above).

While the above formulations have been developed with respect to homogeneous materials, the situation can be quite different for heterogeneous materials. First, cracks may not propagate smoothly with time. Instead they may be arrested at obstacles and then suddenly jump. Second, cracks may not propagate along a smooth path but may kink at interfaces and defects. Third, the J-integral is no longer path-independent. Fourth, crack branching and microcracking distant from the main crack may occur so that the notion of a crack itself may be poorly defined. Fifth, the state of stress can be extremely complex and asymptotic analysis may not be feasible. For these and other reasons, the study of the fracture of heterogenous media has conventionally been a difficult subject.

Against this backdrop, the instant application describes systems and methods for determining an 'effective toughness' that describes the results of a macroscopic experiment without having to resolve the microscopic details. In general, the context for this development is a problem where there is a steady and defined crack growth at the macroscopic scale, but where a crack set is completely free to evolve in any manner that it chooses at the microscopic scale.

This problem can be resolved by implementing what can be referred to as a 'surfing boundary condition.' A 'surfing boundary condition' can be thought of as being manifested by a crack 'steadily propagating' through a material in a prescribed 'overall direction.' In particular, the 'steady propagation' of the crack can be understood to be the relative constant velocity of the crack tip as the crack propagates through the material. Similarly, the 'overall direction' references the relative general direction that the crack is propagating in. Thus, for instance, a heterogeneous material may include heterogeneities—e.g. grains in a ceramic, fibers in a composite, or layers in a layered material, and these heterogeneities can be thought of as defining internal length scale units (e.g. the length of one grain defining one length scale unit); the relative concepts discussed above can be adjudged with respect to these 'internal length scale' units. Thus, for instance, when a crack is subjected to a 'surfing boundary condition,' the crack velocity may vary to some extent (e.g. as the crack navigates through/around the heterogeneities) when being adjudged at this internal length scale; however, at the macroscale, which can be understood to be defined by a plurality of the units defining the internal length scale (e.g. five grains, fibers, or layers, as the case may be), where the individualized effect of each of the heterogeneities becomes indistinguishable (rather, their overall effect is observed on the macroscopic scale), the crack velocity will be adjudged to be relatively constant. For example, the average velocity of the crack tip as it propagates through e.g. five internal length scale units (e.g. grains), may not deviate by more than approximately 15% as compared to the average crack tip velocity associated with a next group of five internal length scale units that the crack propagates through; in this way, the crack velocity can be deemed to be relatively constant. Thus, for instance, FIG. 11B (discussed more fully later) illustrates steady macroscopic crack propagation through a material; in other words, although the crack velocity is not entirely constant, it is relatively constant. Note that although a specific percentage was mentioned in defining 'relativity,' it should be appreciated that any suitable criterion can be used to determine whether the crack velocity is 'relatively' constant. For instance, in some contexts, average crack velocities not deviating by more than 20% may be considered to be relatively constant. Similarly, although the average velocity was discussed with respect to a specific number of internal length scale units, the average velocity can be taken over any suitable number of length scale units in order to determine whether crack propagation can be considered to be steady.

Additionally, in many embodiments, the notion of relative overall direction can also be understood with respect to the internal length scale units. For example, when a material is subjected to a surfing boundary condition, the crack propagation direction can vary substantially on the scale of an internal length scale unit; however, when observed on the macroscale—e.g. a plurality of length scale units—the overall propagation direction should be relatively constant. For example, the average direction can be taken as the crack propagates over fifteen internal length scale units. As before, although fifteen internal length scale units are mentioned, the average overall crack direction can be taken over any suitable number of length scale units in accordance with embodiments of the invention. Also similar to before, the average propagation direction over a suitable number of length scale units can be compared relative to the average propagation directions of subsequent pluralities of length scale units to determine whether the average propagation direction can be deemed to be relatively constant. As can be appreciated, any suitable metric can be used to determine whether the propagation direction can be deemed to be relatively constant. For example, in many embodiments, the average propagation direction can be deemed to be relatively constant if the average crack propagation direction over pluralities of internal length scale units does not deviate by more than 30°. It should be emphasized that any suitable criterion can be implemented. For example, the threshold criterion can be one of: 20°, 25°, 30°, 35°, etc. As can be appreciated, the implemented criterion can be contextually dependent. As one example, FIG. 15B (discussed more fully later) illustrates overall direction; in other words, even though the crack meanders at the internal length-scale, it follows an overall direction of left to right, and so follows a relatively 'overall direction.'

At the outset, consider a large domain $\Omega$ with periodic or random microstructure that is subjected to a time-dependent steadily translating crack opening displacement. While the particular from that is taken is not necessarily important, for most of the calculations shown below, the following form is implemented:

$$u(x,y,t)=U(x-vt,y) \text{ on } \partial\Omega \qquad (6)$$

where U is the Mode-I crack opening displacement [e.g. see Equation (4)] with a given $K_I$ and the elastic modulus is taken to be the effective elastic modulus of the material. Through the derivation, to verify that the definition and results are independent of boundary conditions, the following alternate boundary condition is also considered $$u(x, y, t) = \begin{pmatrix} 0 \\ \frac{A}{2}\left(1 - \tanh\frac{x-vt}{d}\right)\sin(y) \end{pmatrix} \qquad (7)$$

for constants A and d. Note that in each case, the boundary condition corresponds to a macroscopic crack propagating in the x-direction with constant imposed velocity v.

The derivations allow the crack set to evolve as it chooses, and the stress state is computed at each time. The macroscopic energy release rate J at each time is computed taking the boundary as the contour. After an initial transient stage, this J(t) falls into a periodic pattern as long as the crack set is away from the boundary; the effective toughness can be defined as the maximum macroscopic energy release rate.

The goal of this formulation is to provide an effective toughness that is a material property independent of specific boundary conditions. Underlying this formulation is a conjectured homogenization result that such a quantity is indeed well defined and that the aforementioned surfing boundary condition can result in its computation. Second, and related, is the conjecture that J-integral reaches a limiting value as the domain become infinitely large. Finally, note that the effective toughness can—in general—be taken to be the maximum value of the J-integral as opposed to the average. This is because the effective toughness is characterized by the critical points in the energy. This is discussed further below.

It remains to study the evolution of the crack set and the elastic fields at the microscopic scale within the domain $\Omega$. A variational fracture field approach of Bourdin et al. is discussed in Bourdin, B., Francfort, G., Marigo, J. J., 2000, "Numerical experiments in revisited brittle fracture," *J. Mech. Phys. Solids* 48, 797-826, and also Bourdin, B., Francfort, G., Marigo, J. J., 2008, "The variational approach to fracture," *J. Elast.* 91, 1-148. These above-cited disclosures are hereby incorporated by reference in their entirety. In the instant derivations, a scalar regularized fracture field v(x,y,t) taking values in [0,1] and such that v=0 corresponds to a complete fracture and v=1 corresponds to intact material. At the nth step, there is a given $v^n$, and the fracture field $v^{n+1}$ and the displacement field $u^{n+1}$ can be solved as minimizers of the energy $$U_{total} = \int_\Omega \left\{ \frac{1}{2}(v^2+\eta)e(u)\cdot\mathbb{C}(x,y)e(u) + \frac{G_c(x,y)}{c_v}\left(\frac{1-v}{\varepsilon} + \varepsilon|\nabla v|^2\right)\right\} dA \qquad (8)$$

$$U_{total} = U_{elastic} + U_{fracture} \qquad (9)$$

where $c_v=8/3$ is a normalization constant, subject to the constraint $0\le v^{n+1}\le v^n\le 1$. Above, $\eta$, $\varepsilon$ are small parameters, and $\mathbb{C}$ and $G_c$ are pointwise elastic modulus and the fracture toughness respectively (note that the heterogeneity of the material is emphasized by explicitly noting their spatial dependence), and $e(u)=(\nabla u+\nabla u^T)/2$ is strain. Thus, the derivations can be applicable to both homogenous materials as well as heterogeneous materials.

The minimizer has the property that v=1 everywhere except in small narrow regions of width $O(\varepsilon)$. These narrow regions can be interpreted as cracks. In fact, it can be shown rigorously that the energy above Gamma-converges to a sum of elastic and fracture energies as $\varepsilon\to 0$; see e.g., Ambrosio, L., Tortorelli, V. M., 1990, "Approximation of functional depending on jumps by elliptic functional via t-convergence," *Comm. Pure Appl. Math.* 43, 999-1036. The above-cited disclosure is hereby incorporated by reference in its entirety. Roughly, the minimizers of this energy (8) converges to the minimizers of the traditional energy $$\int_\Omega \frac{1}{2}e(u)\cdot\mathbb{C}(x,y)e(u)dA + \int_\Gamma G_c(x)dl \qquad (10)$$

where $\Gamma$ is an unknown crack set.

In other words, the regularized fracture field approach above may be viewed as an approximation (regularization) of the variational approach to fracture proposed by Francfort and Marigo (1998). This in turn is a natural extension of the ideas of Griffith that does not require a priori the restriction that cracks are smooth and they propagate smoothly. In short, the approach followed here provides an accurate numerical approximation to crack propagation with no a priori assumptions on the crack geometry or evolution. Furthermore, this approach is rate independent.

Although the fracture toughness is assumed to be isotropic, and the interfacial effects are neglected in the stated derivations, note that these are not limitations of the instant framework.

Note that the functional $U_{total}$ is separately convex in u and v: so the problem of minimizing it in u for fixed v is well-posed, as is the problem of minimizing in v for fixed u. It is non-convex in (u,v) due to the first term ($v^2\nabla u\cdot\mathbb{C}\nabla u$). This is the reason that crack sets can spontaneously nucleate and jump. However, this makes it difficult to solve. But the equations can be solved sequentially, and this leads to the Euler-Lagrange equation $$\nabla\cdot((v^2+\eta)(\mathbb{C}e(u))=0, \qquad (11)$$

For the elastic equilibrium, while optimality with respect to v involves solving a constrained minimization problem. Both problems can be implemented on a supercomputer using unstructured linear finite elements. For example, the basic infrastructure for the mesh management and parallel linear algebra can be provided by PETSc, and the constrained optimization is based on TAO; see e.g. Balay, S., Gropp, W., Curfman McInnes, L., Smith, B., 1997, "Efficient management of parallel is min object oriented numerical software libraries," In: Arge, E., Bruaset, A. M., Langtangen, H. P. (Eds.), *Modern Software Tools in Scientific Computing*, Birkhäauser Press, Cambridge, Mass., USA, pp. 163-202; and Munson, T., Sarich, J., Wild, S., Benson, S., McInnes, L. C., 2012, Tao2.0 "Users Manual, Technical ReportANL/MCS-TM-322," Mathematics and Computer Science Division, Argonne National Laboratory. These above-cited disclosures are incorporated by reference herein in their entirety.

Following "The variational approach to fracture," to Bourdin, cited above, it is noted that for a given regularization parameter £ and mesh size h, the fracture toughness is amplified by a factor $$G_c^{num} = G_c\left(1 + \frac{h}{c_v \varepsilon}\right) \quad (12)$$

The effect can be accounted for in any implemented numerical simulations.

In continuing the stated derivations, it is useful to non-dimensionalize the equations. Typical values of Young's modulus $E_0$ can be used to set the energy scale; similarly a typical value of the length scale $$L_0 = \frac{G_c}{E} = \left(\frac{K_{Ic}}{E}\right)^2 \quad (13)$$

can also be used to non-dimensionalize the equations. The model that is used is rate-dependent, and so only time-scale is given by the boundary condition, and so it is regarded as non-dimensional. Specifically, the total energy $U_{total}$ in (8) is divided by $E_0 L_0^3$ and the following relations are established:

$$\bar{\mathbb{C}} = \frac{\mathbb{C}}{E_0}, \bar{G_c} = \frac{G_c}{E_0 L_0}, \bar{\varepsilon} = \frac{\varepsilon}{L_0}, \bar{\Omega} = \frac{1}{L_0}\Omega, \bar{u} = \frac{u}{L_0}, \bar{x} = \frac{x}{L_0}. \quad (14)$$

The same expression is obtained as in equation (8) except each quantity is replaced by its non-dimensional counterpart (v and η are already non-dimensional). So the bar can be dropped, and the quantities in equation (8) can be treated as being non-dimensional. Note that this scaling is different from what is typically used in fracture mechanics of homogenous materials. Typically, the displacement is scaled by $\sqrt{G_c L/E}$ where L is the size of the domain. This makes the elastic and fracture energies in equation (10) comparable, and thereby renders fracture parameter-independent. However, this typical scaling is not effective in the stated problem since heterogeneous materials are considered and since a regularized theory is used.

The following non-dimensional values are used unless otherwise stated.

$$E=1, G_c=1, v=0.2, \varepsilon=0.5, h=0.1, K_f=1.5 \quad (15)$$

Note that the numerical discretization h is used to be much smaller than ε for convergence.

The following discussion on classic linear elastic fracture mechanics is presented for context, and can provide useful insights pertaining to the above discussion and the further examples presented below; see e.g. "Fracture Mechanics" in *Lecture Notes in Applied Computational Mechanics*, to Zehnder, and "Fracture-analysis of nonhomegenous materials via a moduli-perturbation approach" to Gao, cited above.

Consider an infinite body with elastic modulus $\mathbb{C}(x,y)$ and a semi-infinite crack $\Gamma=(-\infty, 0)\times\{0\}$ subjected to far-field Mode-I loading. It is assumed that the elastic contrast is small so that $\mathbb{C}(x,y)=\mathbb{C}^0+\mathbb{C}^1(x,y)$ with $\mathbb{C}^0$ uniform and $|\mathbb{C}^1|<<|\mathbb{C}^0|$. The solution to this problem can be obtained asymptotically by making the ansatz that the elastic displacement field $u=u^0+u^1$ with $|u^1|<<|u^0|$. It follows that $u^0$ is the solution to the problem in the homogenous medium with modulus $\mathbb{C}^0$ and thus given by equation (4) for an isotropic elastic material. Furthermore, $u^1$ also satisfies a problem in the homogeneous medium with modulus $\mathbb{C}^0$, but with an additional body force from the heterogeneity:

$$\mathbb{C}^0_{ijkl}u^1_{k,lj} = -(\mathbb{C}^1_{ijkl}u^0_{k,l})_{,j} =: -b_i \quad (16)$$

In the instant context, what is of interest are situations where $\mathbb{C}^1$ is discontinuous and thus the derivative on the right-hand side has to be interpreted in the distributional sense. Specifically, if $\mathbb{C}^1$ is uniform and isotropic on $\Omega$ and zero outside, then one has a concentrated body force on the boundary of $\Omega$ and $$b_i = \int_{\partial\Omega} \delta(x-y)(\lambda^1 \epsilon_{kk}^0 n_i + 2\mu^1 \epsilon_{ij}^0 n_j)) dl_y, \quad (17)$$

where n is the outward normal to $\Omega$.

Equation (16) can be solved by superposition of (i) a body with no crack but subjected to the given body force and (ii) a body with a crack whose crack faces are subject to the tractions equal and opposite to those inferred from problem (i). Problem (i) can be solved by using Papkovitch-Neuber-Boussinesq potentials to obtain $$u^1 = \frac{1}{2\mu}(\nabla(\phi + x \cdot \psi) - 4(1-v)\psi) \quad (18)$$

Where φ and ψ satisfy Poisson's equations $$\Delta\phi = -\frac{1}{2(1-v)}b\cdot x, \Delta\psi = \frac{1}{2(1-v)}b \quad (19)$$

that are solved using the fundamental solution (log |x| in two dimensions). Then, the stress field $\sigma^{1i}$ and the tractions $t^{\pm}$ that they impose on the location of the crack faces (±denotes the two crack faces) can be obtained.

Problem (ii) can be solved using the Bueckner weight function; see. e.g. Bueckner, H. F., 1970, "A novel principle for the computation of stress intensity factors," Z. Angew, *Math. Mech.*, 50, 529-546. The disclosure of this above-cited reference is incorporated by reference herein in its entirety. Define the complex function $R=(t_n-it_s)$ where $t_n$ and $t_s$ are the normal and shear components of the fraction on the + crack face. Then, complex stress intensity factor $K^*=\sqrt{\pi}(K_I-iK_{II})$ due to the perturbed field is given by $$K^* = \frac{\sqrt{2}}{\pi}\int_{-\infty}^{0} R(t)|t|^{-1/2} dt. \quad (20)$$

Figure 1B:
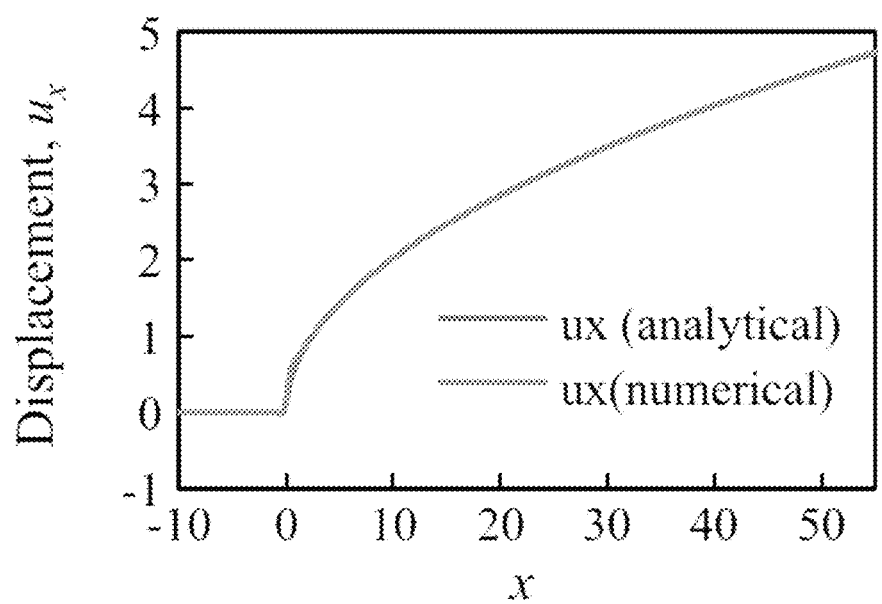
Figure 1C:
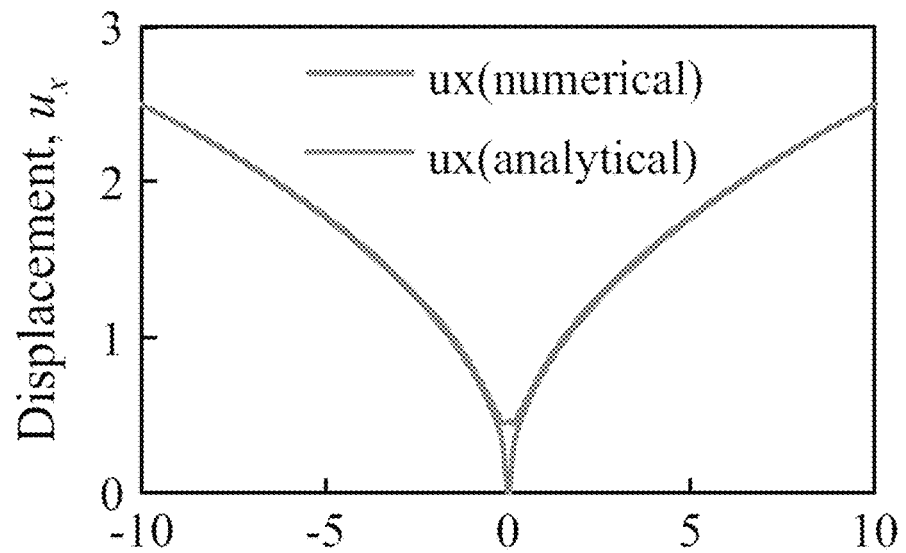

FIGS. 1A-1D illustrate using the above-stated derivations to compute the effective toughness of a homogenous material in accordance with certain embodiments of the invention. In particular, FIG. 1A illustrates the tested sample that is a 65 unit by 48 unit sample with an initial crack length of 10. 'Surfing boundary conditions' are implemented to characterize the propagation of the crack. In particular, in the illustrated embodiment, the surfing boundary conditions take the form of equation (6). More specifically, in the illustrated embodiment, $K_I$=1.0 and $G_c$=1.5. The rest of the parameters are as stated in equations (15). The computed horizontal displacement field $u_x$ at t=0$^+$ is shown in FIGS. 1B and 1C along the x- and y-axis respectively, with the origin located at the crack tip. Note that they agree very well with the analytic $K_I$ field, equation (4), except close to the crack tip due to the regularization.

Figure 1D:
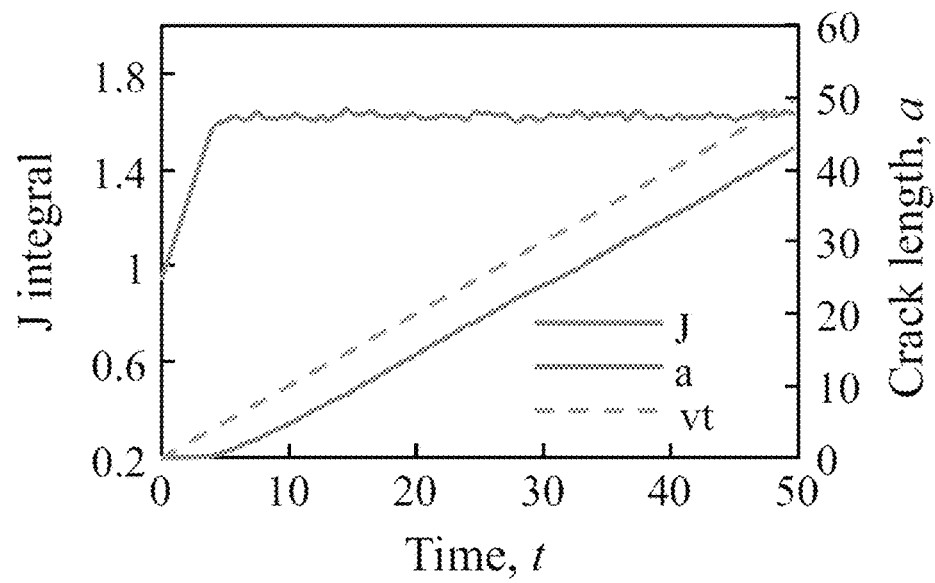

FIG. 1D illustrates the computed J-integral along the boundary as well as the position of the crack. Note that the initial J is very close to the expected value $$\frac{K_I^2}{E} = 1;$$

it is slightly smaller because of the regularization at the crack tip. Since J is lower than the $G_c$ for the material, the crack does not grow. As time progresses and the applied opening displacement translates to the right, the value of J at the boundary increases. The crack begins to grow as soon as J reaches the value and then grows steadily with the velocity of the imposed boundary condition as J remains constant. Thus, the critical J inferred from the boundary conditions when the crack propagates steadily is in fact equal to the toughness of the material. In effect, FIGS. 1A-1D illustrate the viability of the above-described derivation and methodologies within the context of a homogeneous material.

Note that while a certain surfing boundary condition was illustrated with respect to FIGS. 1A-1D, any of a variety of surfing boundary conditions can be implemented in accordance with embodiments of the invention. For example, the surfing boundary condition corresponding with equation (7) can be implemented in accordance with many embodiments of the invention.

Figure 2A:
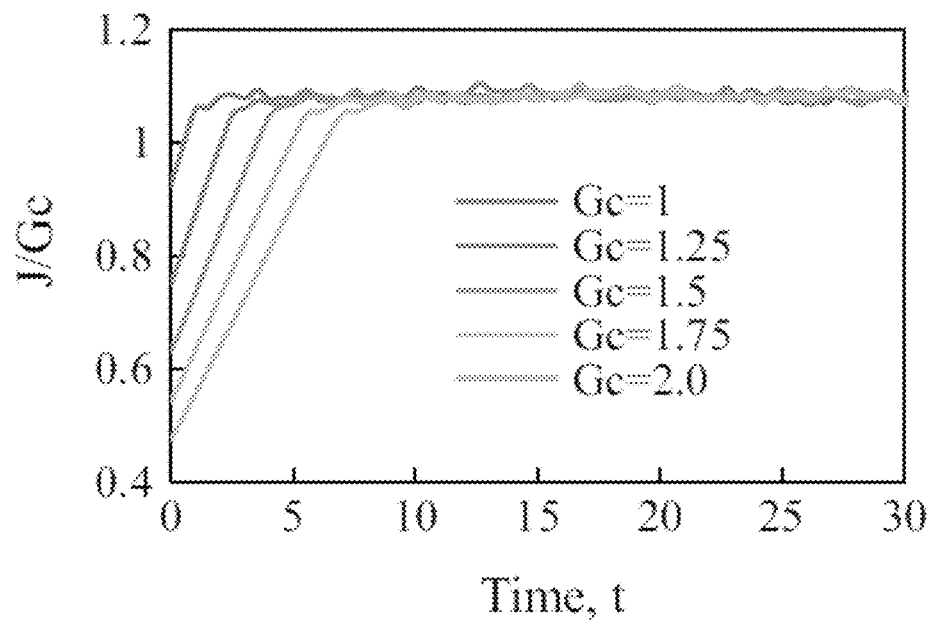
FIGS. 2A-2D illustrate data associated with assessing the effective toughness of a homogenous material in various circumstances in accordance with certain embodiments of the invention.
Figure 2B:
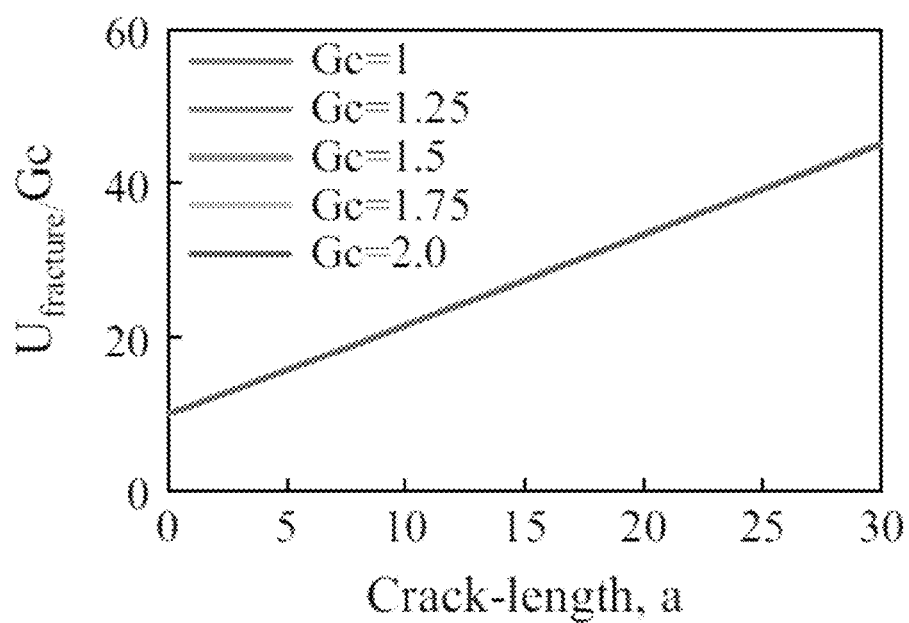
Figure 2C:
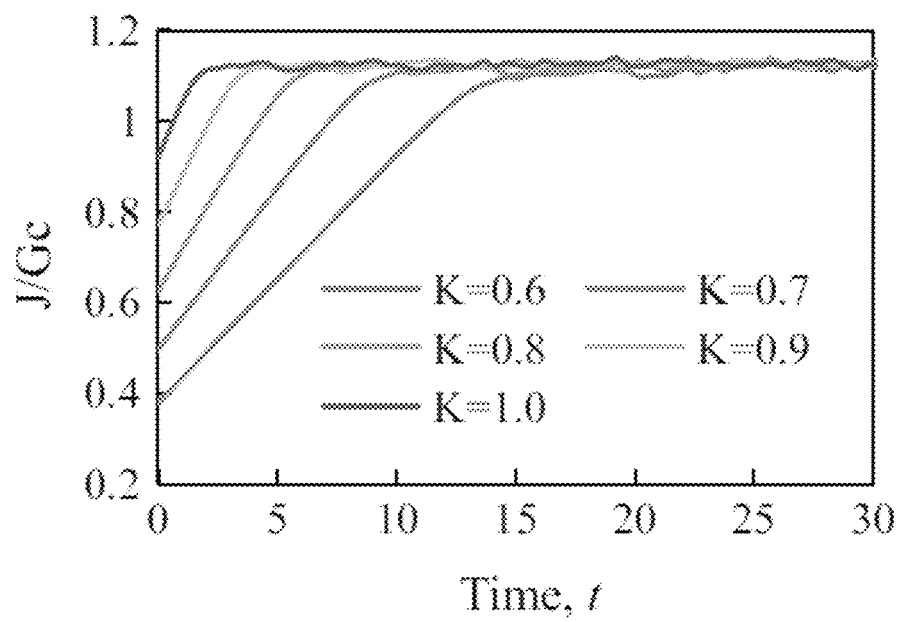
Figure 2D:
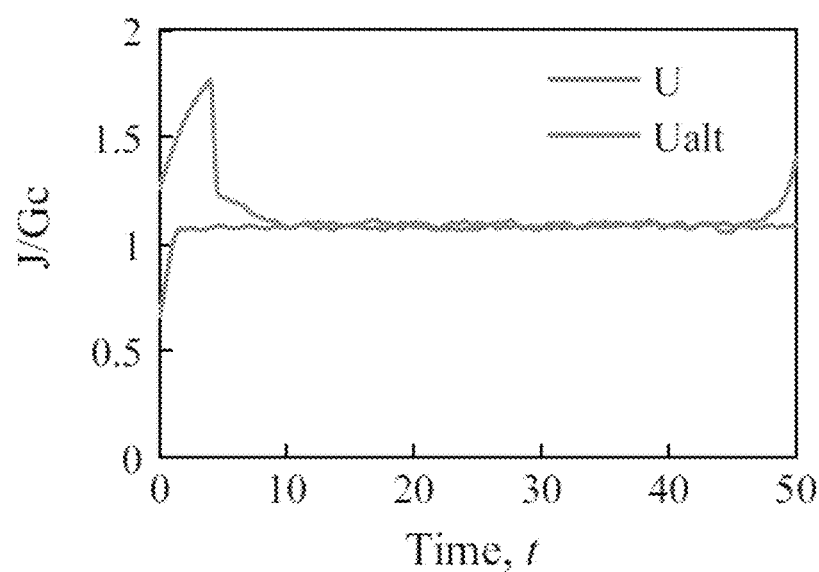

FIGS. 2A-2D illustrate the efficacy of the described methodologies in various circumstances. For example, FIG. 2A illustrates J/$G_c$ as a function of time for varying $G_c$ values. Note that for each case, the critical J inferred from the boundary conditions when the crack propagates steadily is in fact equal to the toughness $G_c^{num}$ of the material. Similarly, FIG. 2B illustrates the $U_{fracture}/G_c$ as a function of crack length, a for various values of $G_c$. For the various values, the slope of the curves are exactly equal to $G_c^{num}$ as would be expected in a homogeneous material. FIG. 2C illustrates the results of the same computations illustrated above, but with various values of applied $K_I$ (holding $G_c$=1.5 fixed). Notice that while the initial value of J reflects the applied $K_I$, the critical value is independent of it. FIG. 2D illustrates the alternate surfing boundary condition corresponding with equation (7), with a $G_c$=1.5. It is illustrated that in this case, the transient creates a higher J, but it quickly reaches the steady value of $G_c^{num}$=1.6. Accordingly, it is seen that the computed $G_c$ is independent of the boundary condition.

Figure 3A:
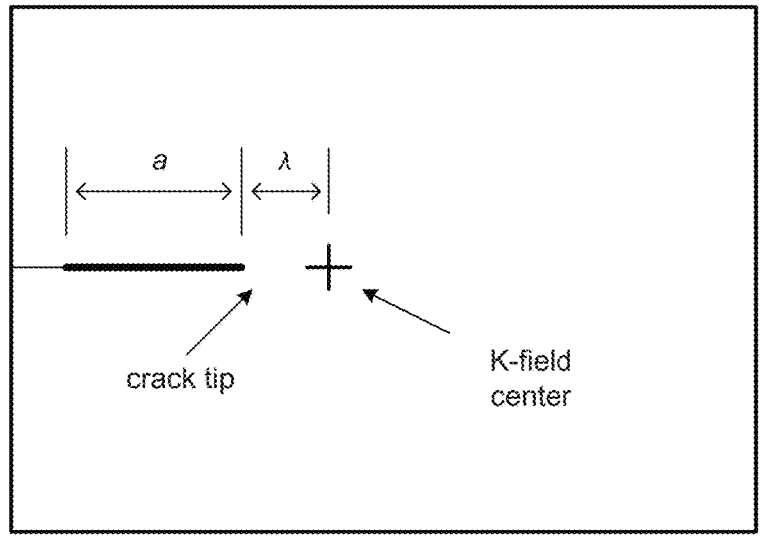
FIGS. 3A-3D illustrate data associated with assessing the effective toughness of a material where there is an offset between the respective crack tip and the K-field in accordance with certain embodiments of the invention.
Figure 3B:
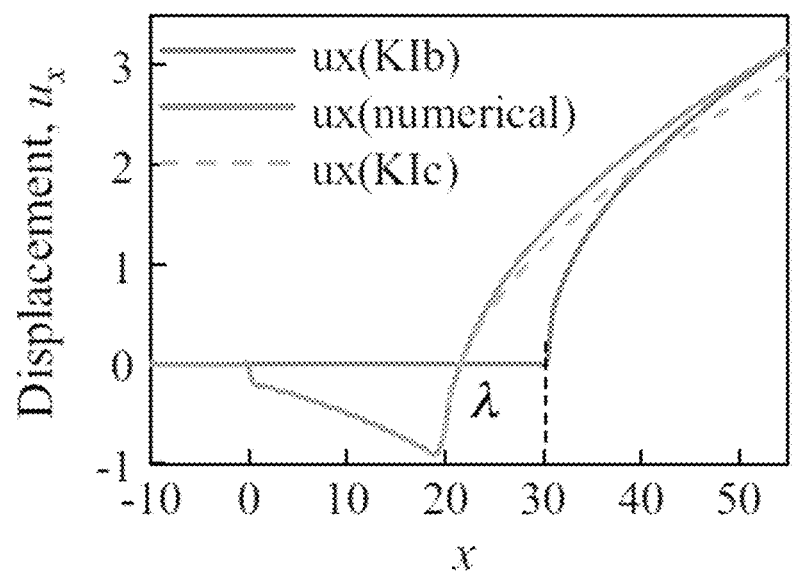
Figure 3C:
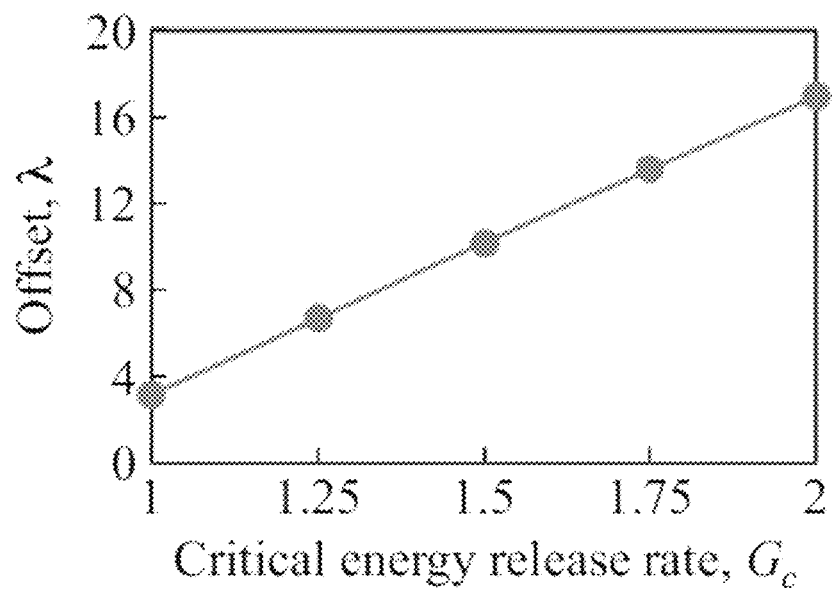
Figure 3D:
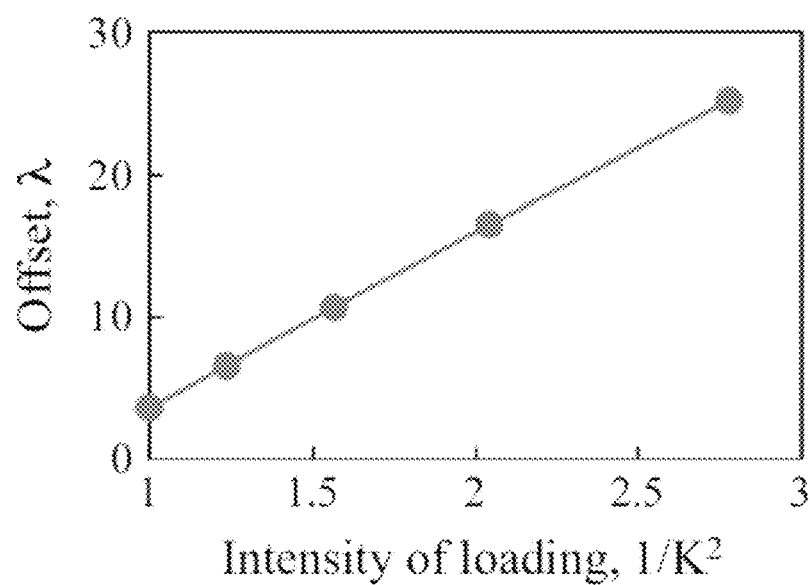

Recall that when the applied $K_I$ is lower than that corresponding to the material at $G_c$, the crack tip trails the center of the applied boundary condition. FIGS. 3A-3D illustrate applying a surfing boundary condition to the situation where the applied boundary condition is offset from the crack tip. In particular, FIG. 3A illustrates how the applied boundary condition center is offset from the crack tip. In particular, it is depicted that the K-field center is offset from the crack tip by a distance λ. FIG. 3B shows the horizontal displacement field along the x-axis with the original crack tip as the origin. Note that the displacement field is similar to that corresponding to $K_{Ic}$ near the crack tip, but changes in the far field to that corresponding to the applied boundary value. FIG. 3C shows that the offset is proportional to $G_c$ for a fixed applied $K_I$. FIG. 3D illustrates that the offset is inversely proportional to the square of the applied $K_I$ for a fixed $G_c$. These relations are as expected from linear elastic fracture mechanics.

Figure 4:
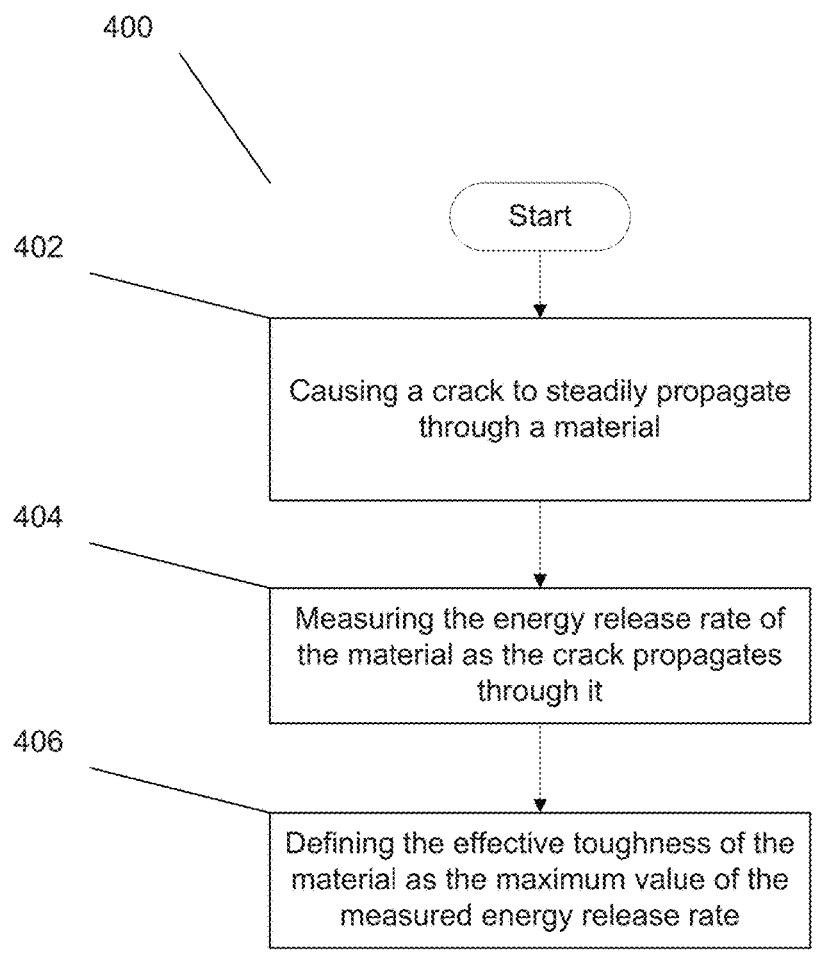
FIG. 4 illustrates a method for determining the effective toughness of a material in accordance with certain embodiments of the invention.

While the above discussion has principally regarded the theoretical underpinning for the notion of 'effective toughness,' as well as sample data illustrating its efficacy, many embodiments of the invention include specific methods for measuring the effective toughness of a material. For example, FIG. 4 illustrates a process for measuring the effective toughness of a material. In particular the process 400 includes causing 402 a crack to steadily propagate through a material. In many embodiments, the 'steady' propagation of the crack is assessed from a macroscopic perspective (as alluded to above). In many embodiments, the 'steady crack propagation' is characterized by the average crack tip velocity over a predetermined period of time being relatively constant throughout the propagation of the crack, as well as a broad overall propagation direction being maintained. Thus for instance, in some embodiments, a predetermined period of time of 2 seconds is established; accordingly, the crack tip velocity will be relatively constant when measured across the various 2 second intervals for the duration of the propagation of the crack. Of course, it can be appreciated that while the example of a 2 second predetermined period of time is given, it should be appreciated that any suitable predetermined period of time can be implemented in accordance with embodiments of the invention. Thus for instance, predetermined periods of time of 2, 3, 4, and 5 seconds can each be implemented in accordance with embodiments of the invention.

In many embodiments, the 'steady crack propagation' is characterized by the average crack tip velocity and average crack direction over a predetermined length or distance being relatively constant throughout the propagation of the crack. This concept was previously elaborated on above. Thus, for instance, in some embodiments, a predetermined distance of five internal length scale units is established; and the average velocity of the crack tip as it propagates through the various five unit segments constituting the overall crack propagation is relatively constant. As before, whether the average velocity across the various five unit sections is 'relatively' constant can be adjudged using any suitable criterion. For example, average velocities not deviating by more than 15% can be deemed to be 'relatively' constant. Additionally, as alluded to previously, these notions can also be used to adjudge whether the crack propagation direction can be deemed to be relatively constant. To reiterate, it can be appreciated that while the example of five internal length scale units is given, any suitable predetermined distance can be implemented in accordance with embodiments of the invention. Thus for instance, predetermined distances of seven, nine, eleven, thirteen and fifteen units can each be implemented in accordance with embodiments of the invention. Additionally, different numbers of length scale units can be used in assessing average crack tip velocity and average crack propagation direction. Recall, that the intent is to establish the overall steady propagation of the crack.

Note that the steady propagation of the crack can be implemented in any of a variety of ways in accordance with embodiments of the invention. For example, any suitable testing apparatus can be used to provoke the steady propagation of the crack. The process 400 further includes measuring 402 the energy release rate of the material as the crack propagates through it. As can be appreciated, the energy release rate of the material can be measured 404 in any suitable way in accordance with many embodiments of the invention. The process further includes 406 defining the 'effective toughness' of the material as the maximum value of the measured energy release rate. From the discussion above, it can be appreciated that this 'effective toughness' can serve as a robust measure for the tested material's inherent toughness characteristics. As can be appreciated, the process described in FIG. 4 is generalized and can be implemented in any of a variety of ways in accordance with many embodiments of the invention. Accordingly, the example below presents one specific methodology for measuring the effective toughness of a material in accordance with certain embodiments of the invention.

EXAMPLE

Figure 5A:
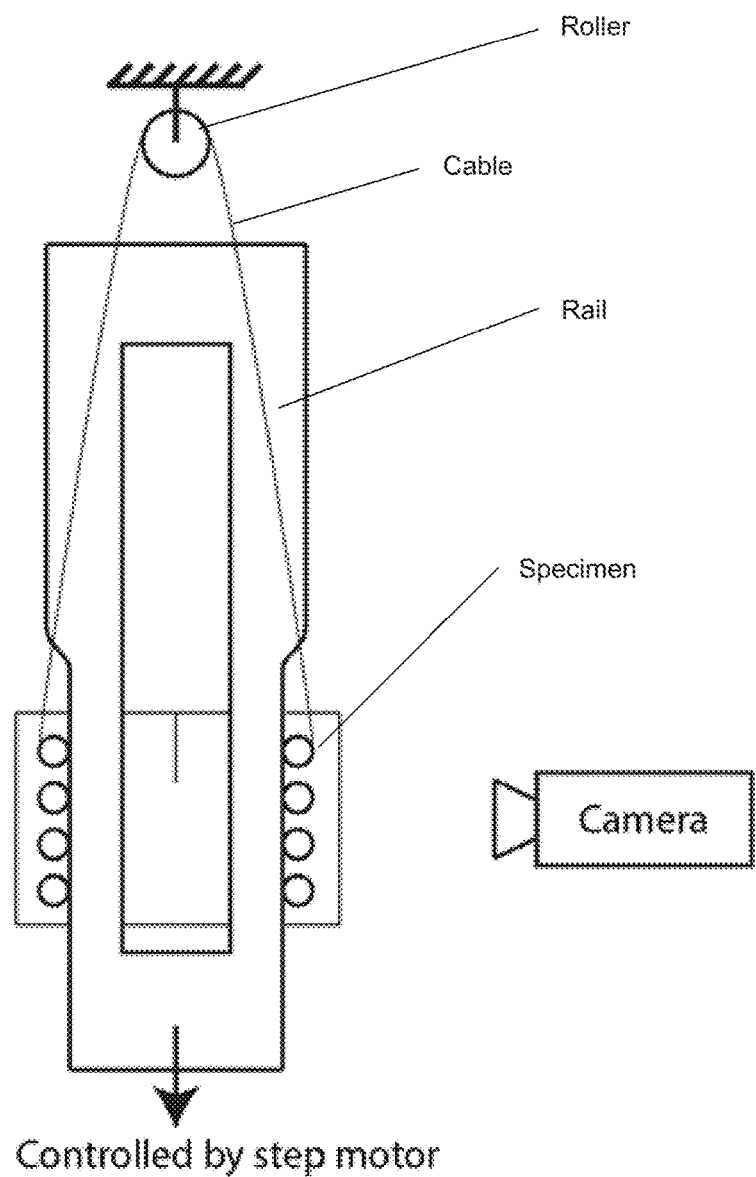
FIGS. 5A-5C illustrate a testing configuration for determining the effective toughness of a material in accordance with an embodiment of the invention.
Figure 5B:
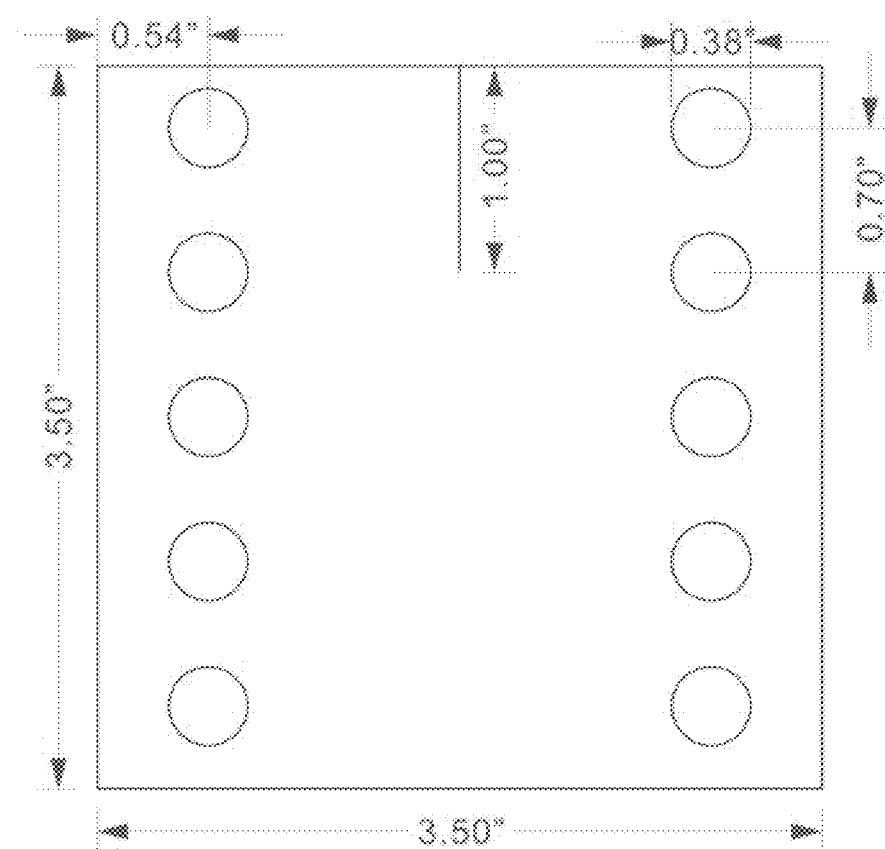
Figure 5C:
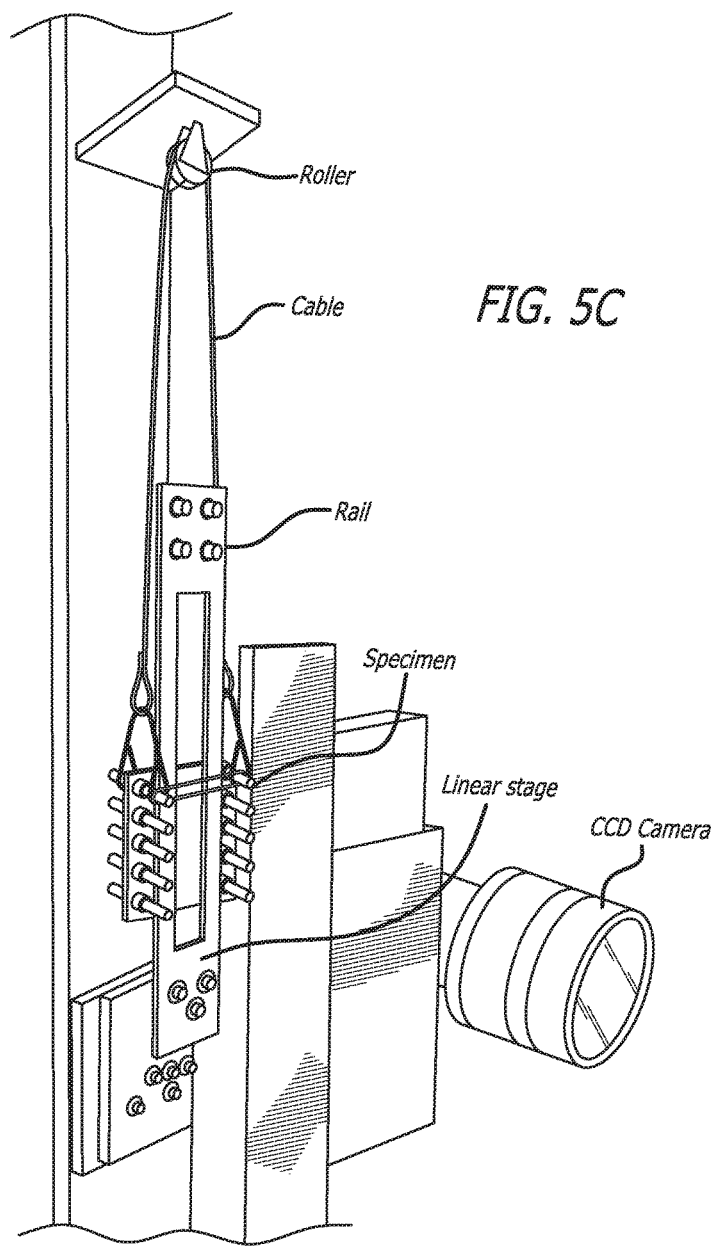

FIGS. 5A-5C illustrate a testing configuration that can be implemented to measure the effective toughness of a material in accordance with an embodiment of the invention. In particular, FIG. 5A depicts a diagram of the testing apparatus. More specifically, it is illustrated that the testing apparatus includes a specimen, disposed on a rail, and in conjunction with a cable/roller system that helps control the specimen; a step motor helps control the specimen. FIG. 5B illustrates a material sample that can be used in conjunction with the testing apparatus illustrated in FIG. 5A. Although, a particular specimen sample size is discussed in relation to this example, it should of course be appreciated that a sample size of any dimension can be implemented in accordance with many embodiments of the invention. FIG. 5C illustrates a photograph of the testing apparatus.

In this example, the specimen was cut from ⅛" thick Homalite H-911 sheets using a laser cutter. Rods were then inserted into the specimen and were attached to a specifically shaped rail with rollers; the rail is disposed on a linear stage. The linear stage pulls the rail downwards while the specimen is held fixed by the cables. As a result of the shape of the rails, when the linear stage pulls the rail down and the specimen slides along the rail, the rail imposes a smoothly translating crack opening displacement that approximates the above-stated surfing boundary conditions. Accordingly, the macroscopic energy release rate can be determined by measuring the macroscopic stress intensity factor. More precisely, the existence of a K-dominant region can be assumed, and digital image correlation can be used. A random fine speckle pattern is applied on the specimens. When the specimen is deformed, a CCD camera observes the deformation of the pattern. A global data analysis method can then be used to calculate the stress intensity factor.

Figure 6:
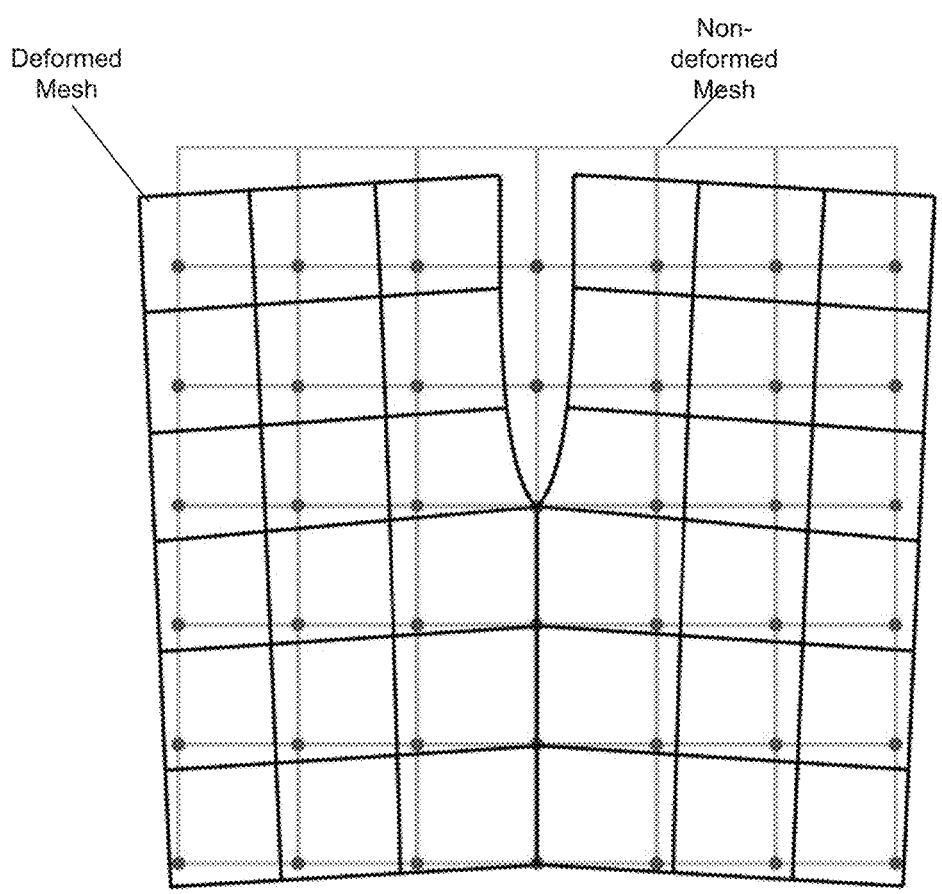
FIG. 6 illustrates sample deformed meshes observed when propagating a crack through a material to determine its effective toughness in accordance with an embodiment of the invention.

The grey level in the deformed image is related to the grey level in the reference image by $$f(x) = g(x + u(x)) \tag{21}$$

where u(x) is the displacement field in reference configuration. FIG. 6 illustrates reference and deformed meshes that are observed. It is also known that the mode-I asymptotic displacement field is $$u(x; K_I, x_0) = \frac{K_I}{2\mu} \sqrt{\frac{r}{2\pi}} U(\theta; \kappa) \tag{22}$$

where μ,K corresponds to the material properties, r,θ is the polar coordinate with origin coinciding with crack tip position $x_0$, θ=0 coinciding with crack propagate direction, and $K_I$ is the stress intensity factor. Thus, the deformed position of each pixel for a reference image f(x) with given stress intensity factor $K_I$ and crack tip position $x_0$ can be calculated. Linear interpolation can then be used to establish the grey value for these points that are enclosed in the deformed meshes and use background value for these points that are not enclosed in the deformed meshes. This way, deformed reference image g(x; $K_I, x_0$) can be calculated.

The cost function can be defined as the difference between the experiment observation and the deformed reference image, as is shown in the following equation:

$$\int_\Omega \|G(x) - g(x; K_I, x_0)\|^2 d\Omega \tag{23}$$

where G(x) is the experiment observation and g(x; $K_I, x_0$) is the deformed reference image with given stress intensity factor and crack tip position. Minimizing the cost function above with respect to $K_I$ and $x_0$ gives the optimal stress intensity factor and the optimal crack tip position.

In general the following optimization problem is not convex $$\min_{x_0, K_I} \int_\Omega \|G(x) - g(x; K_I, x_0)\|^2 d\Omega \tag{24}$$

Figure 7:
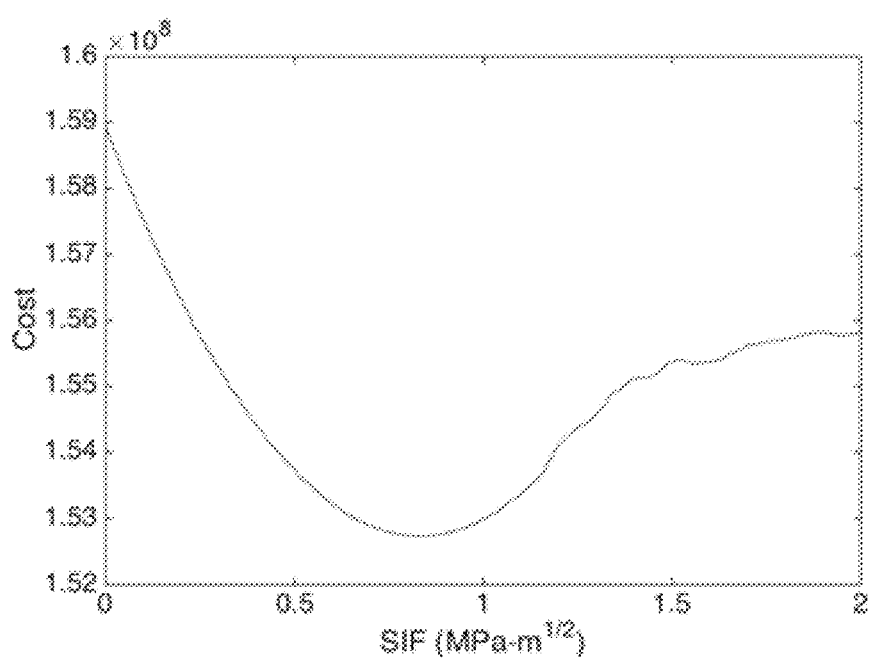
FIG. 7 illustrates a plot of a cost function vs. stress intensity for a given crack tip position that was obtained when determining the effective toughness of a material in accordance with an embodiment of the invention.

However, the cost function versus the stress intensity for a fixed crack tip position $x_0$ is depicted in FIG. 7, and is seen that the function is convex when the stress intensity factor is smaller than a certain critical value. Thus, it is necessary to establish the minimum value for a given crack tip position when the initial guess is small enough. The discussion below utilizes 0.5 MPa·√m as the initial guess.

To calculate, the optimal pair ($K_I$, $x_0$), the deformed reference image and the experiment observation image were compared, and an initial guess for the crack tip position $\tilde{x}_0$ was made. A region A was then constructed with initial guess $\tilde{x}_0$ as the center. For every crack tip position contained in region A, the corresponding optimal stress intensity factor and the cost function were calculated. On the basis of these calculations, the optimal pair with minimum cost function can be chosen.

Figure 8:
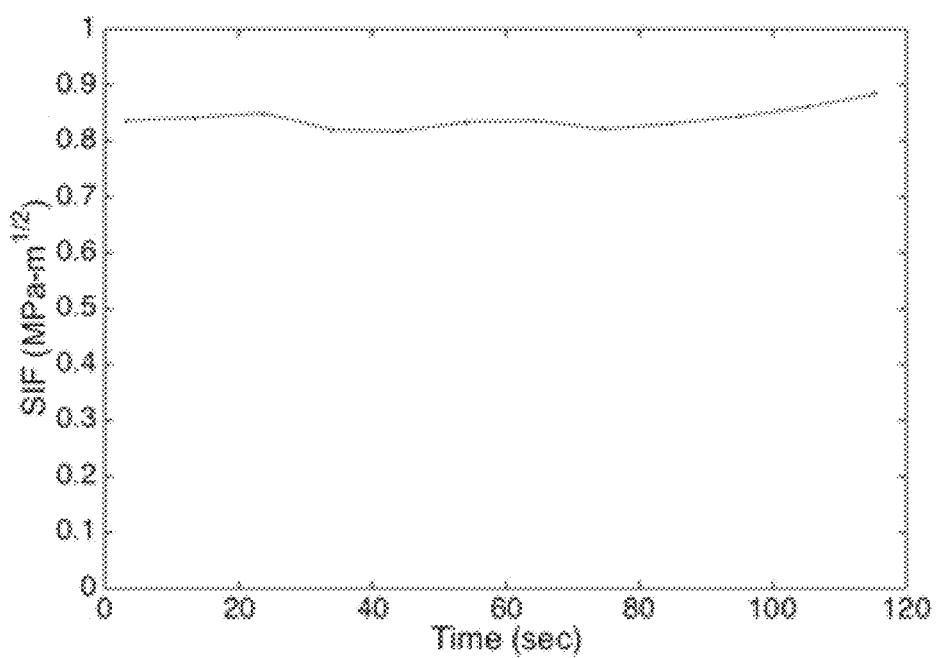
FIG. 8 illustrates a stress intensity plot that was obtained when determining the effective toughness of a material in accordance with an embodiment of the invention.

This procedure was applied to the images of the crack propagation in the previously discussed and depicted homalite specimen; the stress intensity plots are depicted in FIG. 8. As can be seen from FIG. 8, the stress intensity factor is quite stable in homogeneous material as the crack propagates steadily through the specimen. This result is in agreement with findings regarding the properties of linear elastic fracture mechanics: $K_I = \sqrt{G_c E}$.

Figure 9:
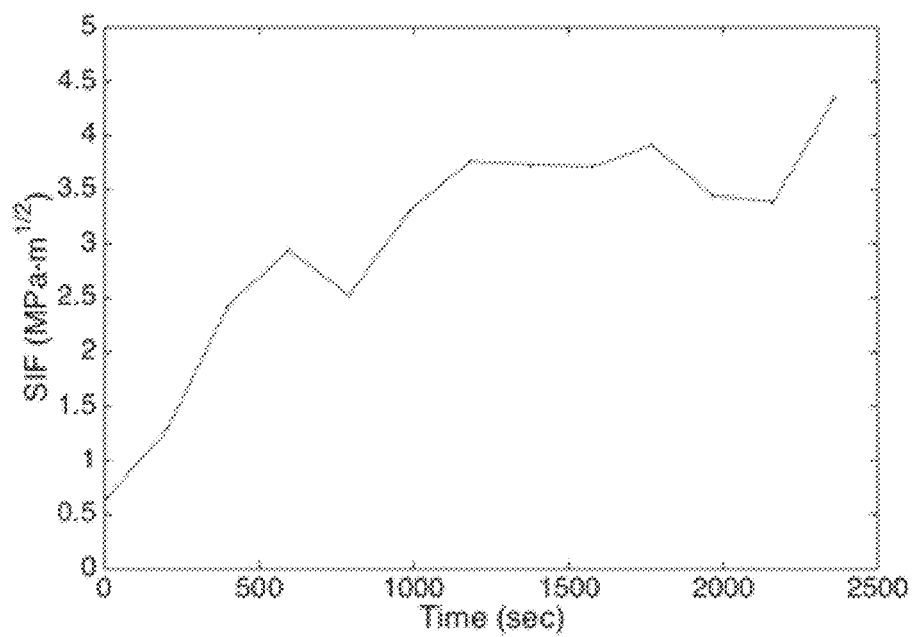
FIG. 9 illustrates a stress intensity plot that was obtained when determining the effective toughness of a heterogeneous material in accordance with an embodiment of the invention.

This procedure was also applied to heterogeneous specimens having holes. It was observed that when the crack tip is trapped in a hole, the driving force (or stress intensity factor) is increased dramatically; FIG. 9 shows this result. In effect, more energy would need to be applied to the crack tip for the crack to propagate. Thus, in this case, the effective toughness of the heterogeneous material is higher than that of the homogeneous material.

In essence, the above described methodologies provide for effective ways of evaluating the non-boundary condition dependent, inherent toughness of a given material.

Effective Toughening Due to Elastic Heterogeneity

In many embodiments, the above understanding of effective toughness is used in implementing materials having robust effective toughness due to elastic heterogeneity. Elastic heterogeneity can be implemented in any of a variety of ways to result in a toughened material in accordance with embodiments of the invention. For example, in many embodiments, a material having a Young's modulus varying in an oscillatory manner along a first direction within a material is implemented. In a number of embodiments, a material having alternating 'stripes' being characterized by different Young's moduli can be implemented. Although, to be clear, elastic heterogeneity within a material to result in a toughened material can be implemented in any of a variety of ways in accordance with many embodiments of the invention.

The first involves smooth modulation and was studied by Gao in 1991 in the low contrast regime, and also provides further verification of the above-described numerical methods for determining the effective toughness of materials.

Figure 10A:
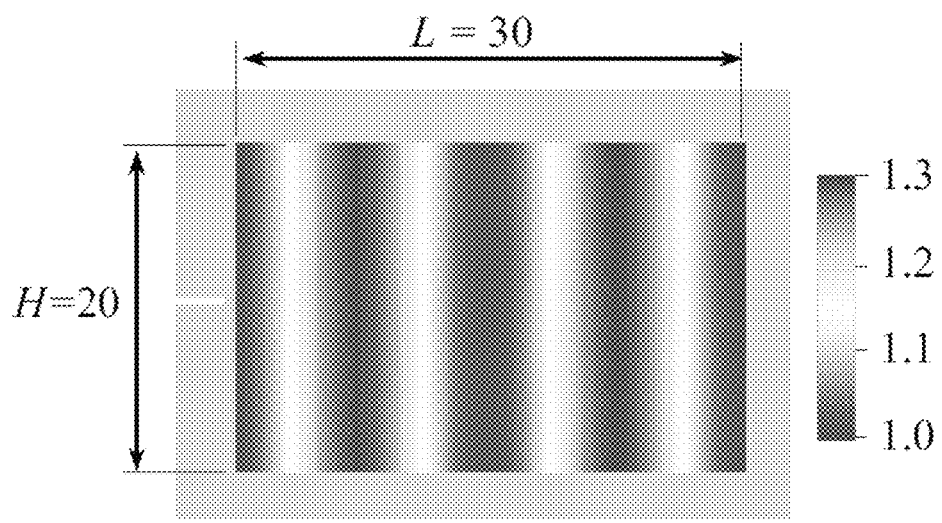
FIGS. 10A-10B illustrate implementing elastic heterogeneity in the form of a sinusoidally varying elastic modulus to derive an effectively tough material in accordance with certain embodiments of the invention.
Figure 10B:
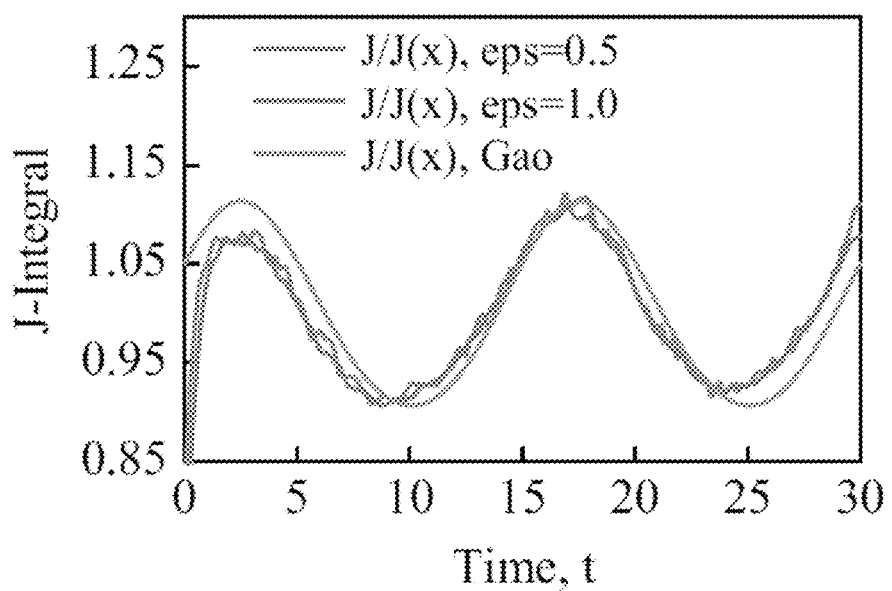

For example, FIGS. 10A-10B illustrate a material having a Young's modulus that varies in a sinusoidal manner in accordance with certain embodiments of the invention. Such materials were studied by Gao in 1991 in the absence of the notion of effective toughness. In effect, Gao disclosed that varying elastic characteristics caused a varying stress intensity factor, but Gao did not disclose that it made the overall material tougher. In particular, FIG. 10A illustrates a domain with Young's modulus smoothly varying in the x-direction.

$$E(x) = E_0 - E_A \cos \frac{2\pi x}{\lambda} \quad (25)$$

In the illustrated embodiment, Poisson's ratio and the fracture toughness are kept uniform at $v=0.2$ and $G_c=1$. In the illustrated embodiment, for computational efficiency, and also due to subtle point regarding the J-integral which is discussed later, the microstructure is kept in the core of the domain and is surrounded by a material with a homogeneous elastic region with elastic modulus equal to the effective modulus of the heterogeneous medium as shown in FIG. 10A. More specifically, it is depicted that the elastic modulus varies sinusoidally in the x-direction from $E_{min}=1$ to $E_{max}=1.3$ (with $E_0=1.15$, $E_A=0.15$, $\lambda=0.15$). A crack is introduced as shown, and a surfing boundary condition is applied with $K_f=1.5$. It is found that the crack propagates smoothly along a straight line $\{y=0\}$. The computed J at the boundary (normalized by $G_c^{num}$) for two values of $\varepsilon$ is shown in FIG. 10B.

It is found that the macroscopic J increases as the crack reaches the compliant region and then decreases as the crack reaches the stiff region. Briefly, the state of stress is heterogeneous and it is low in the regions with low elastic modulus. Therefore, a larger driving force is required to propagate the crack through this region. Importantly, the crack has to reach a macroscopic value that is 1.10 times higher than the uniform pointwise value before it can propagate through a macroscopic distance. Therefore, the macroscopic effective toughness is higher than the uniform pointwise toughness of the medium. Note that in the illustrated embodiment, the crack path remains straight in this example so that this higher value has little to do with crack deviation. Therefore, it can be concluded that elastic heterogeneity is in itself an 'effective toughening' mechanism. Note that since the crack propagation is smooth and there is no instability or re-nucleation involved, the computed J is independent of the value of $\varepsilon$ as shown.

It has been verified that the computed J on the boundary is independent of the constant $K_f$ in the surfing boundary condition. Similar to the scenario depicted in FIG. 2C for the homogeneous case, the time when the crack begins to propagate changes with the constant $K_f$ in the boundary condition, but not the driving force at which it begins propagation.

Gao had studied this problem (in his publication cited above) in the low contrast regime described above. Using similar techniques, he has shown that $$\frac{K(x)}{K_\infty} = 1 + \frac{3-4v}{8(1-v)} \frac{E_A}{E_\infty} \left( 2\cos\left(\frac{2\pi x}{\lambda} + \pi\right) + \sin\left(\frac{2\pi x}{\lambda} + \pi\right) \right) \quad (26)$$

where $K(x)$ is the stress-intensity factor at the crack-tip when it is at the position x and $K_\infty$ is the macroscopic stress-intensity factor. Irwin's formula, equation (5), can be used (separately at the tip and at infinity) to obtain the ratio of the crack-tip energy release rate $J_{tip}(x)$ to the macroscopic energy release rate J. Using the crack propagation criterion $J_{tip}(x)=G_c$ gives the value of the macroscopic energy release rate J when the crack-tip is at the point x. This is also shown in FIG. 10B. In effect, FIG. 10B further verifies the discussed computational approach for computing effective toughness, and relatedly illustrates how it can be used to compute the effective toughness of a material having elastic heterogeneity.

Figure 11A:
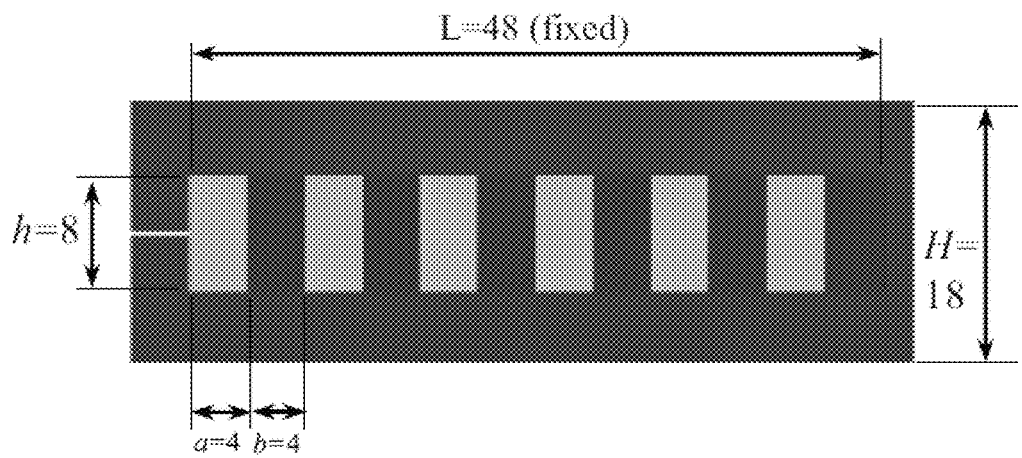
FIGS. 11A-11B illustrate implementing elastic heterogeneity in the form of alternating elastic modulus values to derive an effectively tough material in accordance with certain embodiments of the invention.
Figure 11B:
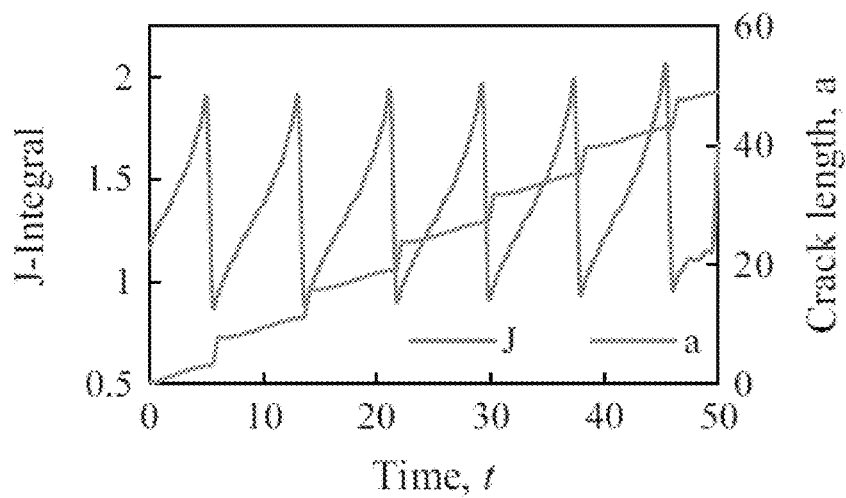

While the above example has regarded the implementation of a material having sinusoidally varying stiffness characteristics, in many embodiments, layers of material having alternative stiffness characteristics are implemented. FIGS. 11A and 11B illustrate a material having layers having alternating stiffness characteristics. In particular, FIG. 11A illustrates that a material includes alternating layers of material having alternating stiffness characteristics. Further, in the illustrated embodiment, the stripes have equal areal fraction and are of width 2 (or period 4). The Poisson ratio is uniform at 0.2, and importantly, the fracture toughness is uniform at $G_c=1$. Finally $\varepsilon=0.25$. For computational efficiency, and also due to subtle point regarding the J-integral which is discussed later, the microstructure is kept in the core of the domain (48×8) and surrounded by a material with a homogeneous elastic region with elastic modulus equal to the effective modulus of the heterogeneous medium.

In the illustrated embodiment, a crack of length 5 is introduced as before and a surfing boundary condition is applied with $K_f=1.5$. It is observed that the crack does not propagate smoothly. Instead, it gets trapped in the compliant layer (before the interface separating the compliant and stiff layers) and the computed J on the boundary begins to rise. The crack eventually breaks through when J reaches a critical value and jumps across the interface and bulk of the stiff material. This is accompanied with a drop in J. The crack then grows slowly and smoothly for a short distance before getting trapped once again. Moreover, the crack path remains straight.

An important observation here in the illustrated embodiment is that the applied J has to reach a value of 1.91 before the crack can propagate through a macroscopic distance (the average of the three peaks are taken since one has end effects on the subsequent ones). Thus, the effective toughness is characterized by $G_c^{eff}=1.91$. Note that this is strictly larger than the uniform toughness of the medium $G_c^{eff}=1.15$.

Furthermore, the crack path remains straight and it is again shown that elastic heterogeneity is in itself a toughening mechanism.

Figure 12A:
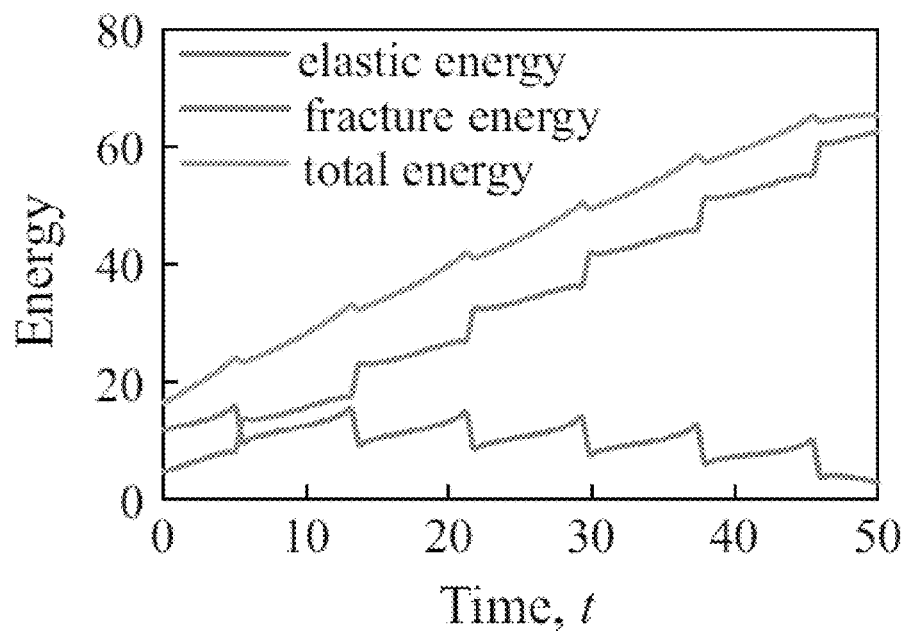
FIGS. 12A-12D illustrate plots of various parameters pertaining to the material illustrated in FIGS. 11A-11B and implemented in accordance with certain embodiments of the invention.
Figure 12B:
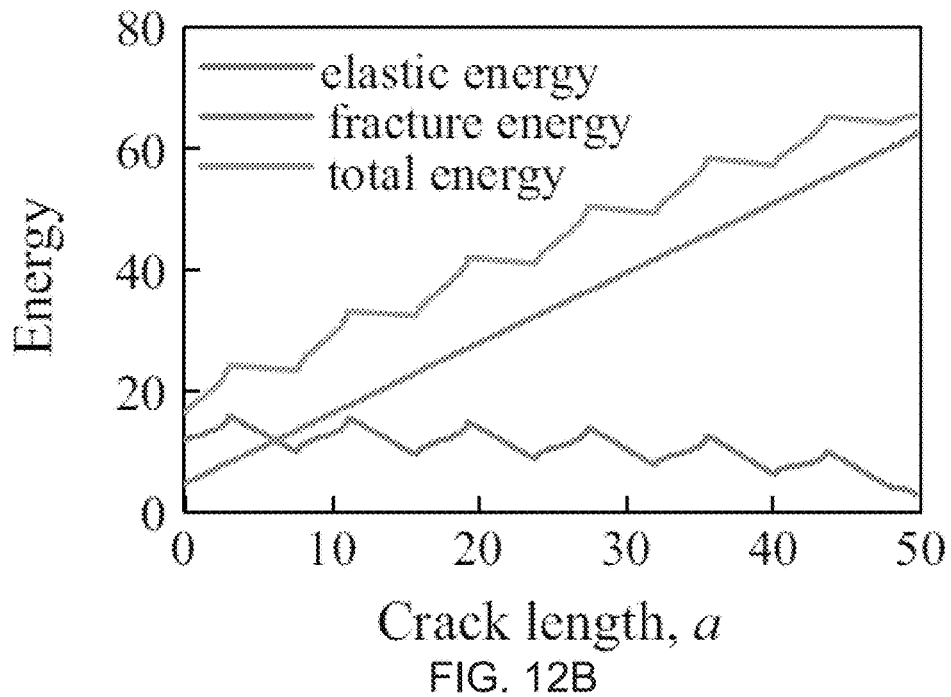
Figure 12C:
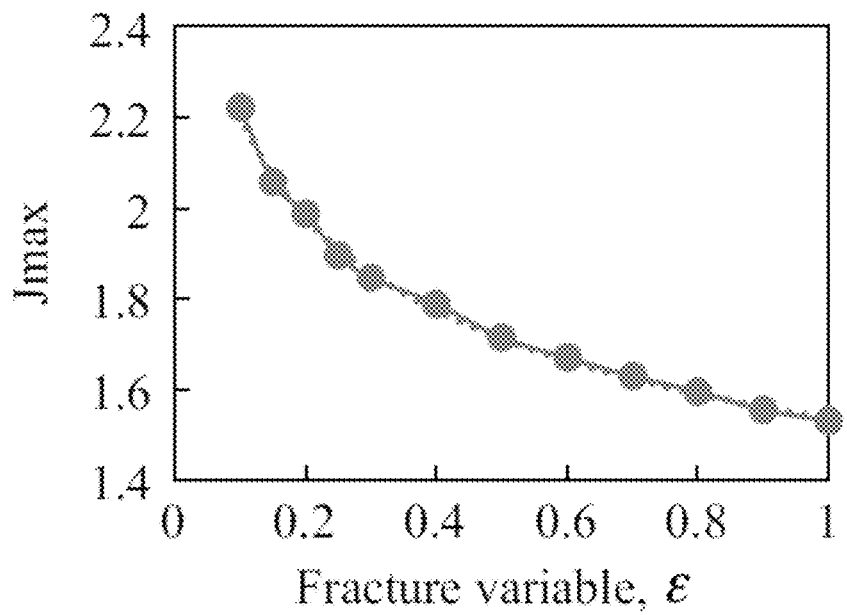
Figure 12D:
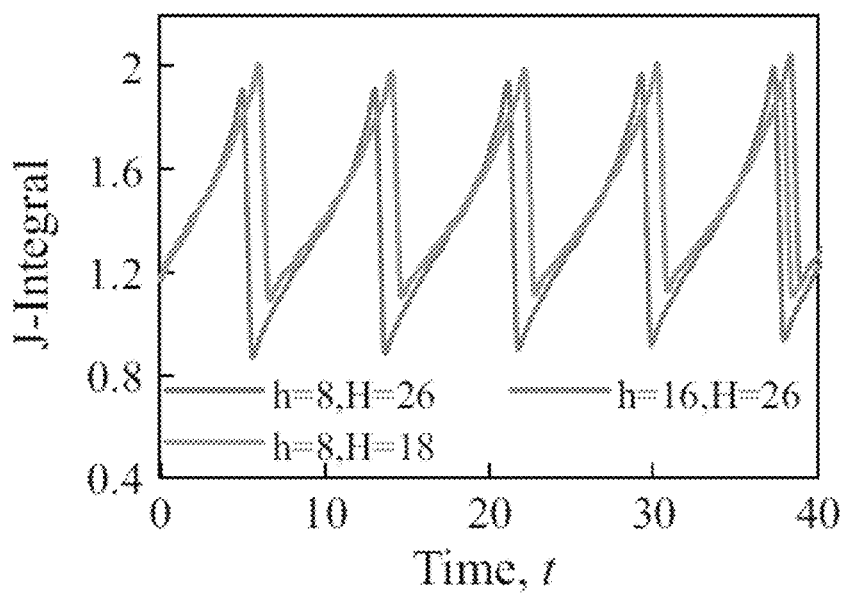

FIGS. 12A-12D show further details of the example presented above with respect to FIGS. 11A-11B. FIGS. In particular, FIGS. 12A-12B show the total elastic and fracture energy as a function of time and as a function of crack length respectively. Notice that the elastic energy builds up as the crack is trapped and is suddenly released when the crack jumps. The fracture energy does exactly the opposite. The total energy also shows oscillations. FIG. 12C shows the effect of ε (the regularization parameter) keeping h=ε fixed. Notice that this value increases with decreasing ε. FIG. 12D shows the results of the computation with domains of various sizes. It is found that the result is essentially independent of the domain size. It is also verified the independence with respect to boundary condition by repeating the calculation with various applied $K_I$ as well as the alternate boundary condition, equation (7).

While embodiments of the invention are not bound to any stated beliefs, it is believed that there are two reasons for the toughening. First, in the absence of the crack, the compliant region has a lower value of stress than the stiff region. Therefore, if the width of the stripes is large enough, the crack tip experiences a lower driving force when it is in the compliant region. Thus, the macroscopic driving force has to be increased to propagate it through this region. A simple calculation shows that this would lead to an increase in $G_c^{eff}$ exactly equal to the ratio of the effective Young's modulus to that of the compliant material. In the discussed example, this would mean $G_c^{contrast}=1.5$ so that $G_c^{contrast,num}=1.725$, but this is lower than what is observed.

Figure 13A:
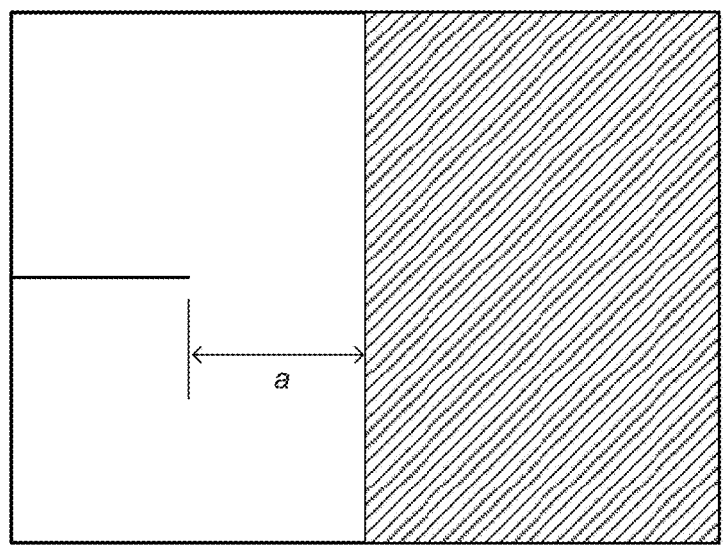
FIGS. 13A-13B illustrate a semi-analytic study of a crack approaching an interface with a stiffer material in an infinite domain in accordance with certain embodiments of the invention.
Figure 13B:
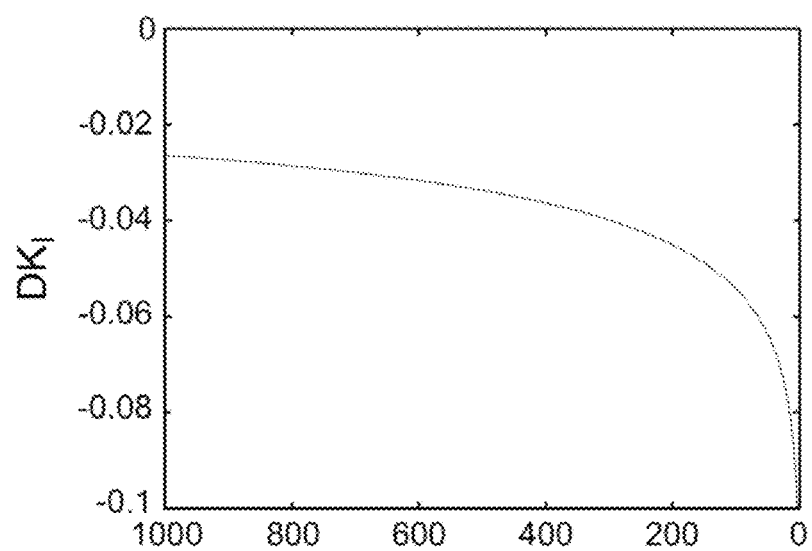

This points to the second reason. As the crack approaches the stiff region from the compliant region, some of the driving force on the boundary is consumed in suddenly deforming the stiff region. Thus, continued propagation of the crack can require even higher macroscopic driving force. This is depicted qualitatively in FIGS. 13A-13B using the semi-analytic method. Consider an infinite domain, with a semi-infinite crack approaching the interface between a compliant region (left) and a stiff region (right) as shown in FIG. 13A. As the crack approaches the interface, it is seen that the crack intensity factor and the driving force on the crack front decreases as shown in FIG. 13B. Thus sustained propagation requires increased driving force.

Note that the $K_I$ diverges as the crack-tip approaches the interface, as noted by Atkinson; see e.g. Atkinson, C., 1975, "On the stress intensity factors associated with cracks interacting with an interface between to elastic media," *Int. J. Eng. Sci.* 13, 489-504. The above-cited reference is hereby incorporated by reference in its entirety. In fact, Zak and Williams (1963) showed that when the crack tip is at the interface going from a compliant to a stiff material, the stress field at the crack-tip is not singular and so that the stress-intensity factor is zero; see e.g., Zak, A. R., Williams, M. L., 1963, "Crack point stress singularities at a bi-material interface," *J. Appl. Mech.* 30, 142-143. Thus the crack is arrested at this interface and has to re-nucleate. This depends on the crack-initiation criterion and thus depends on the value of ε.

Figure 14A:
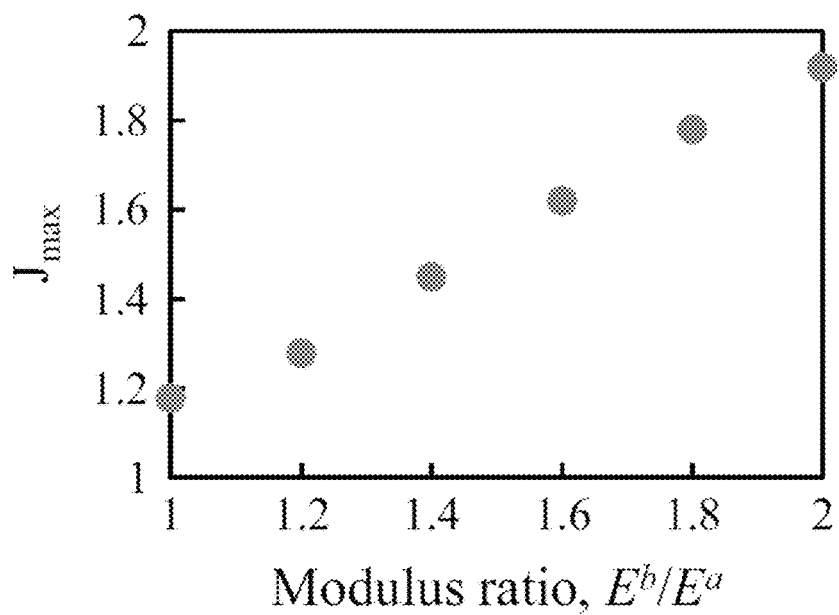
FIGS. 14A-14C illustrate a parameter study of the effective toughness of the material characterized by constituent stripes having elastic heterogeneity with respect to elastic contrast, strip width, and volume fraction in accordance with certain embodiments of the invention.
Figure 14B:
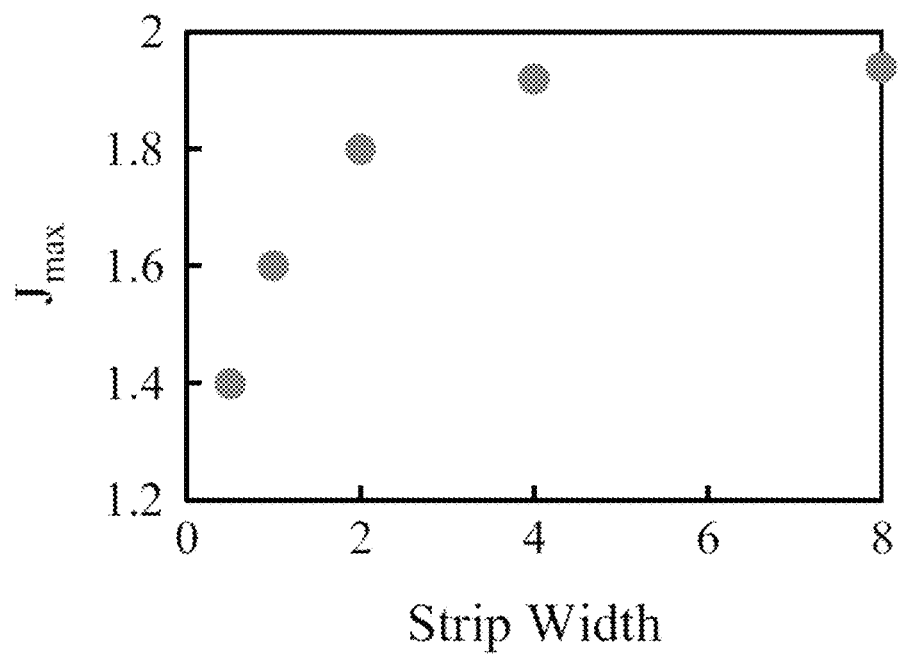
Figure 14C:
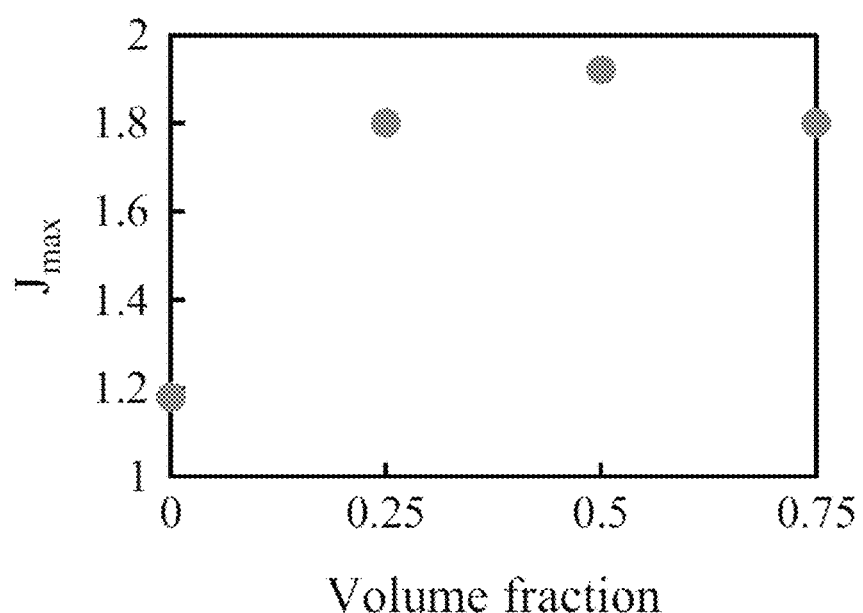

The calculation for various values of parameters (for ε=0.25, h=0.1 fixed) are repeated and the results are shown in FIGS. 14A-14C. FIG. 14A shows how the effective toughness varies with elastic contrast. As the contrast increases, so can the effective toughness due to the contrast in state of stress. FIG. 14B shows the effective toughness for various values of the strip width holding the elastic contrast at 2. Notice that the toughness increases with strip width saturating at 1.91 but decreases to the uniform microscopic value of 1.15 with decreasing length-scale. To understand this, notice that the regularized model has a length-scale due to ε. If the scale of the heterogeneity is small compared to this length-scale, the crack tip sees a uniform elastic material. Since the toughness is uniform in the stated case, it can behave as if it is in a homogeneous medium and there is no toughening. FIG. 14C shows that volume fraction has some effect, but this is related to length-scales. In these calculations, the period is held fixed at 4, and so the width of one material or the other becomes small when the volume fraction approaches 0 or 1.

Note that since the continued propagation is dictated by re-initiation of the crack once it reaches the interface, the interfacial toughness can play an important role. Indeed He and Hutchinson (1989) showed that the crack can deflect into the interface if the interfacial toughness is small enough; see e.g. He, M. Y., Hutchinson, J. W., 1989, "Crack deflection at an interface between dissimilar elastic materials," *Int. J. Solids Struct.* 25, 1053-1067. The above-cited disclosure is hereby incorporated by reference in its entirety. In the illustrated example, the interfacial toughness is exactly the same as the bulk toughness.

Figure 15A:
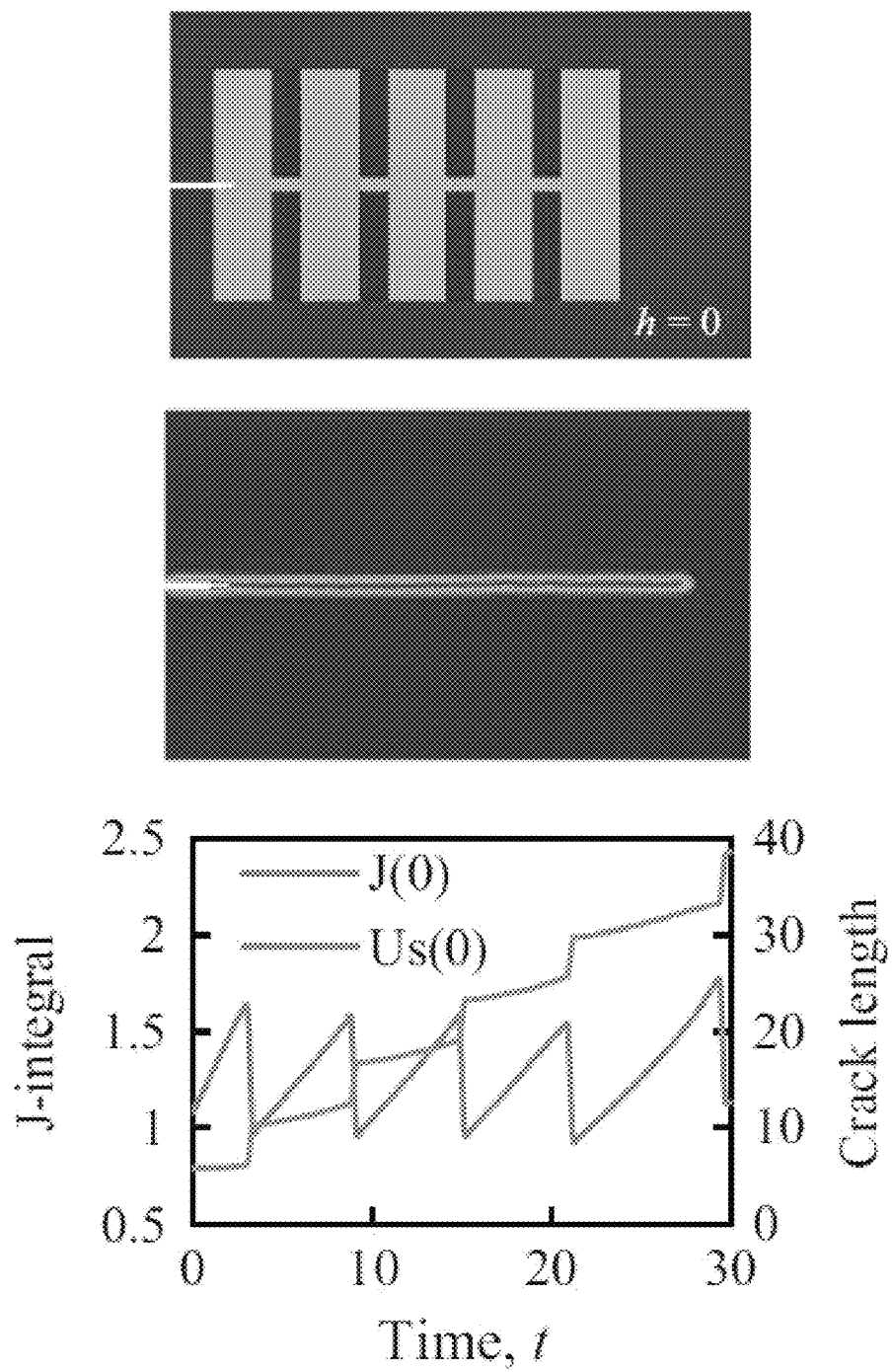
FIGS. 15A-15C illustrate the effects of tortuous crack propagation in a material characterized by elastic heterogeneity in accordance with certain embodiments of the invention.
Figure 15B:
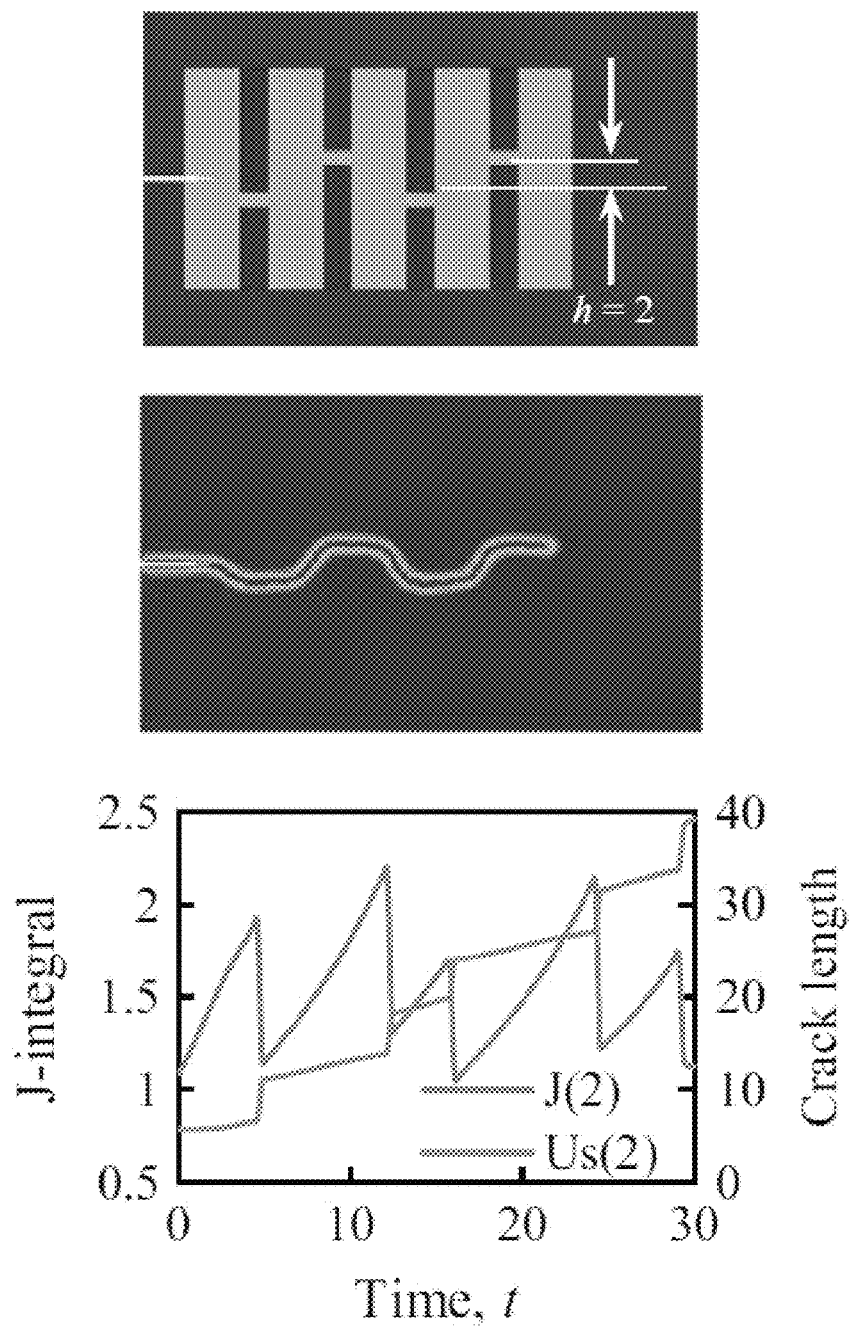
Figure 15C:
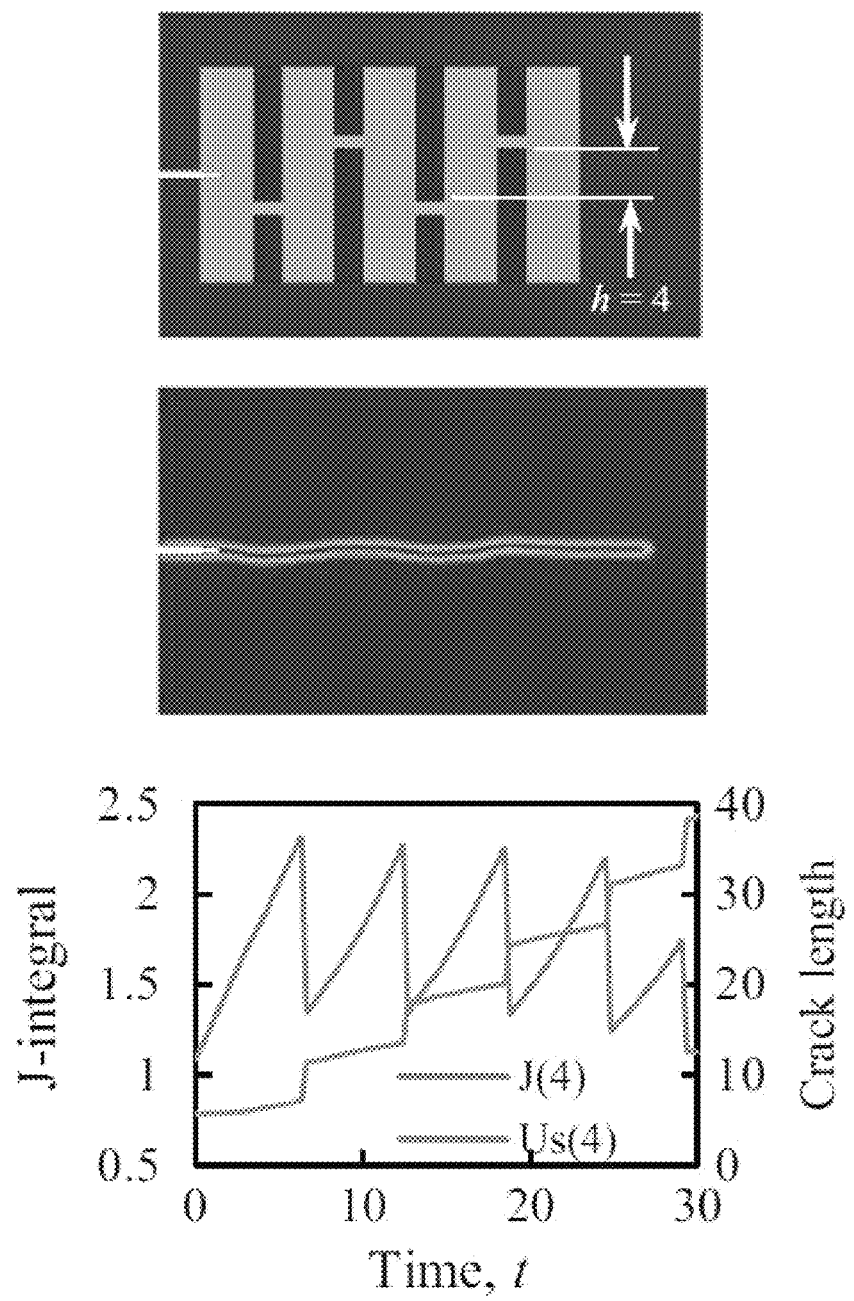

While the above discussions have presumed a crack propagating in a straight manner, in many instances, a crack may not necessarily propagate in a straight manner. FIGS. 15A-15C illustrate the effect on fracture characteristics that a tortuous crack propagation can have. In the illustrations, Young's moduli are taken to be 1 and 4, the width of each layer is 2 and the break in the stiff layer has height 1. The fracture toughness is taken to be uniform at $G_c=1$. The gaps in the different layers are either aligned as shown on the left column of the figure or staggered as shown in the middle and right columns.

When the gaps are all aligned, as in FIG. 15A, the crack propagates straight through the gaps. Still the applied J is not constant because the elastic fields are heterogeneous. Once again, the crack is trapped as it approaches the stiff stripes and discontinuously advances through the gaps. Furthermore, the effective toughness $G_c^{eff}=1.6$ is strictly higher than the uniform microscopic $G_c=1$.

When the gaps are moderately misaligned as shown in middle column of FIGS. 15B-15C, the crack meanders back and forth in a discontinuous manner to take advantage of the gaps. The macroscopic J is not uniform and the effective toughness $G_c^{eff}=2.3$ is strictly higher than the uniform microscopic $G_c=1$. Note that in this example, the overall crack length is larger than in the case FIG. 15A. Though the bottom row shows that the crack length is the same at the end of the simulation in FIGS. 15A and 15B, the crack has traveled a great macroscopic distance in FIG. 15A. This increased crack length would suggest a toughness of 1.5 which is lower than the computed number. Once again, effective toughness is higher than effective surface area.

As the offset between the gaps increase beyond a certain point, the crack no longer meanders, but propagates straight in a jerky manner as if were passing through a layered material as shown in FIG. 15C. The effective toughness is also similar to that of a layered material.

Figure 16A:
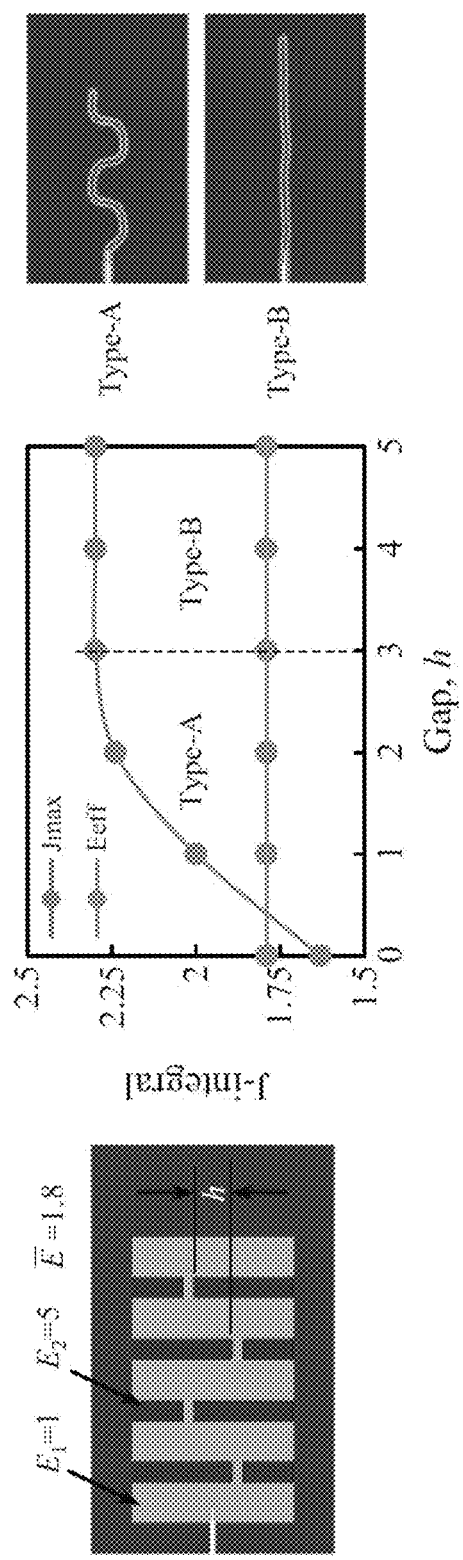
FIGS. 16A-16B illustrate the effect of gap misalignment in materials characterized by elastic heterogeneity in accordance with certain embodiments of the invention.
Figure 16B:
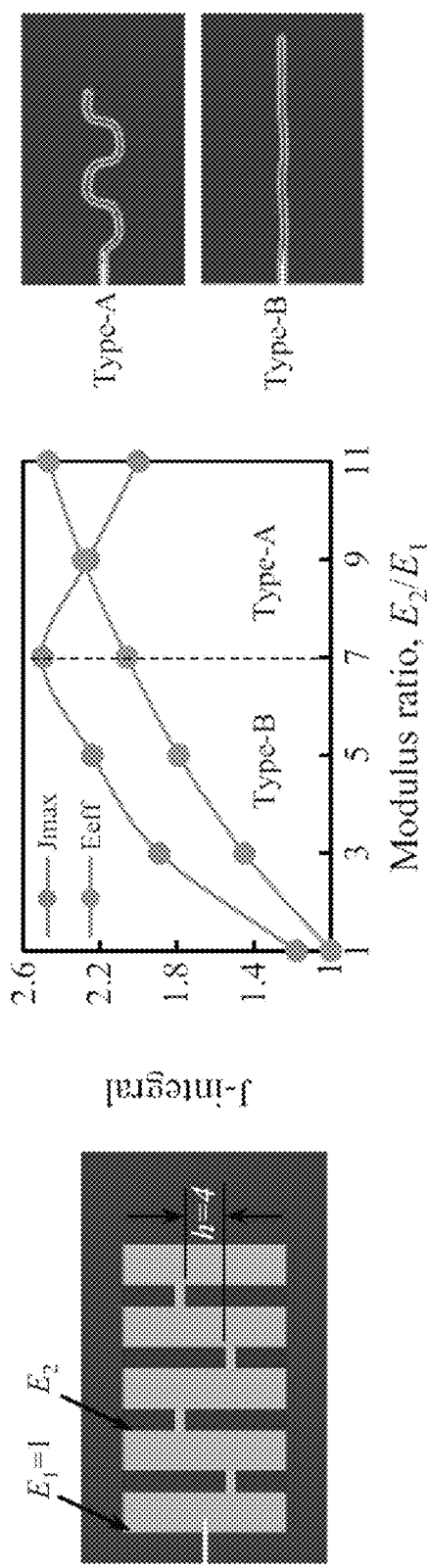

FIG. 16A shows how the effective toughness can change with the misalignment in the gaps. It is seen that it starts at a value greater than the pointwise toughness as discussed above when all the gaps are aligned, and increases with misalignment as the cracks meander to take advantage of the gaps. At some point (h=3 in the illustration), the toughness reaches the value that it would have if the material had no gaps; beyond that the crack propagates straight and the effective toughness saturates. FIG. 16B shows the effect of elastic contrast when the gap is held fixed at h=4. At small contrast, the crack propagates straight but meanders at large contrast.

Accordingly, it is seen how the previously described understanding of effective toughness can be used to implement and study materials having elastic heterogeneity. While a number of examples of materials having elastic heterogeneity have been discussed, it should be appreciated that the above-stated principles can be used to implement any of a variety of materials, e.g. not necessarily only those materials having sinusoidal varying elastic moduli or those having stripes being characterized by alternating moduli. The elastic moduli can vary in any of a variety of ways in accordance with many embodiments of the invention. For example, in some embodiments, the elastic modulus varies in a non-periodic fashion. Additionally, it is also demonstrated how materials can be implemented that result in a tortuous crack propagation, and thereby increasing the overall effective toughness of the material, in accordance with embodiments of the invention.

Effective Toughness Due to Fracture Toughness Heterogeneity

While, the above discussion has regarded the implementation of materials having elastic heterogeneity and thereby having improved effective toughness, in many instances, materials can be implemented that are characterized by fracture toughness heterogeneity.

Figure 17A:
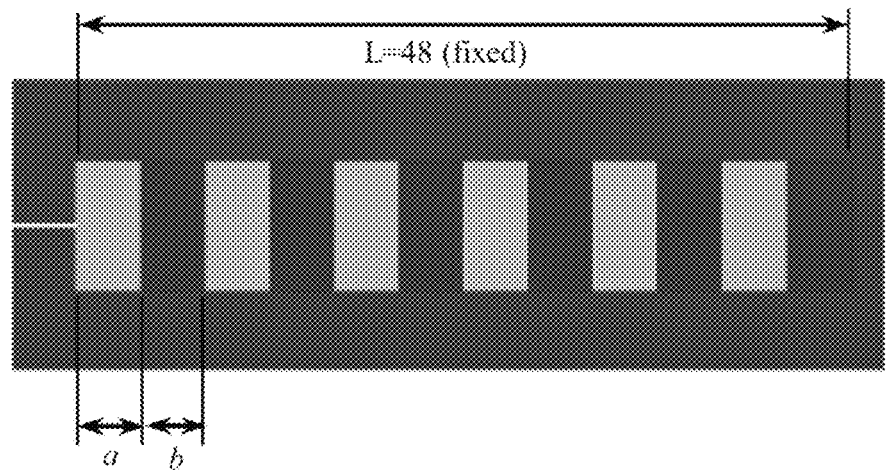
FIGS. 17A-17E illustrate the toughening of a material due to toughness heterogeneity.
Figure 17B:
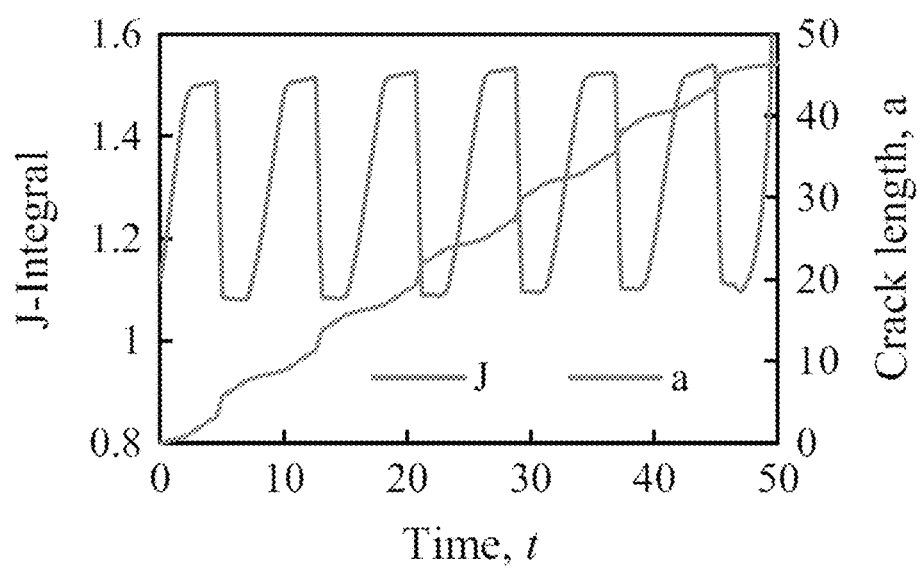
Figure 17C:
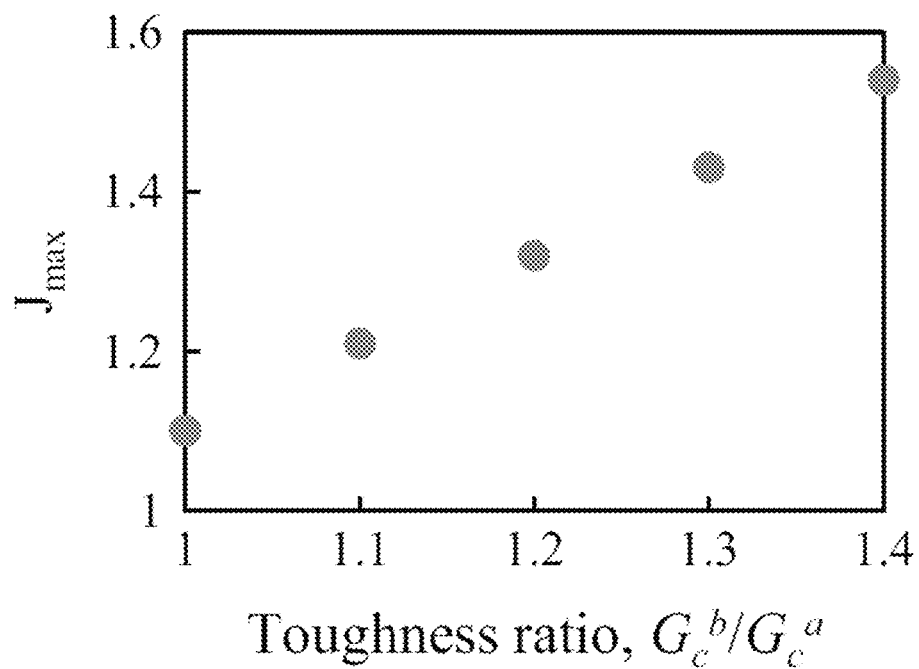
Figure 17D:
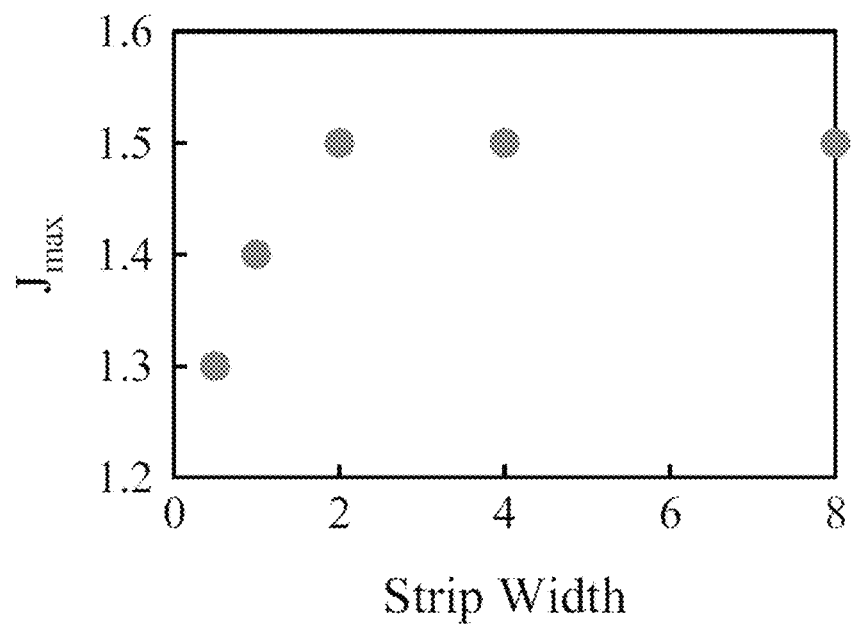
Figure 17E:
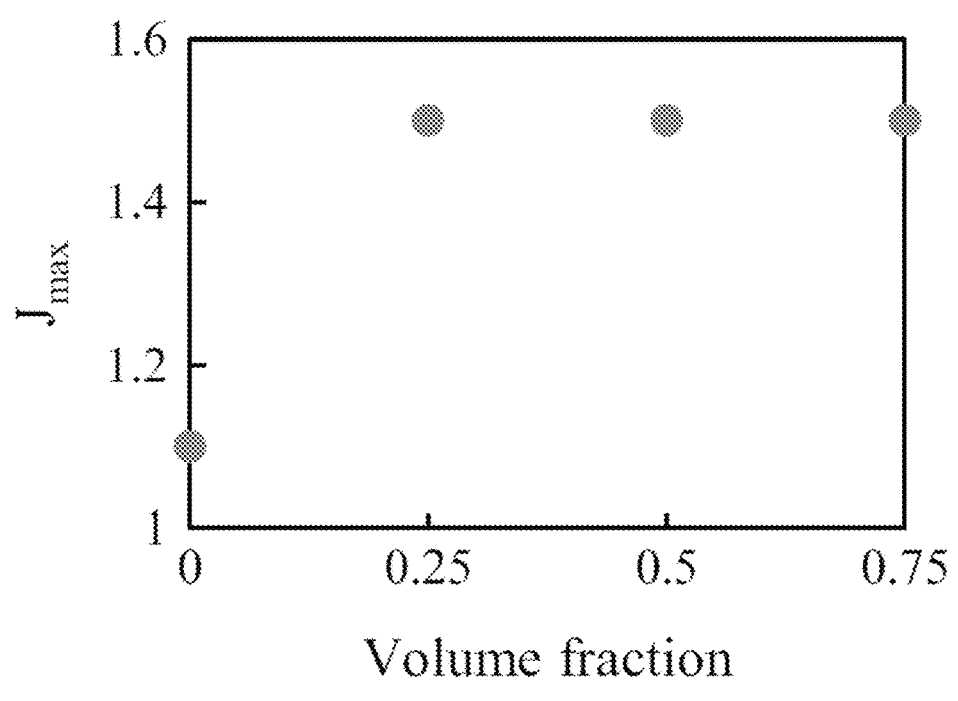

FIGS. 17A-17E illustrate the situation of a stripe domain with uniform elastic modulus but alternating fracture toughness. In particular, FIG. 17A illustrates that the general setup is similar to that seen above with respect to FIG. 11A. Since the elastic modulus is uniform, the J integral is path independent and thus, the applied stress intensity is equal to the stress intensity at the crack tip. Hence, the crack propagates when and only when the macroscopic J is equal to the value of $G_c$ at the crack-tip. Thus it is expected that the applied J to alternate between two values of $G_c^{num}$. This is what is seen in FIG. 17B. Further it is seen that the crack is trapped at the interface between the low and high toughness stripes before jumping through. Finally, in the illustration, the crack can propagate through macroscopic distances only when the applied J reaches the larger of the two values. Consequently the effective toughness is equal to the larger—and not the average—of the two values of $G_c^{num}$. Importantly, the effective toughness is different from the average surface energy. FIGS. 17C-17E show a parameter study.

In the illustration, $G_c^{eff}$ is always equal to the larger of the two $G_c$. The effective toughness is independent of the strip width and the volume fraction—it falls at small length-scales and volume fraction because the regularized model can fail to see the heterogeneity when the scale of the heterogeneity becomes smaller than ε.

While the above example is presented with respect to materials having stripes characterized by alternating fracture toughness values, note that the fracture toughness values can vary in any of a variety of ways. For example, materials having fracture toughness values that vary sinusoidally can be implemented.

Asymmetric Effective Toughness

The role of asymmetry in surface properties, and its exploitation in both nature and in engineering, is only now being recognized; see e.g. Malvadkar, N. A., Hancock, M. J., Sekeroglu, K., Dressick, W. J., Demirel, M. C., 2010, "An engineered anisotropic nanofilm with unidirectional wetting properties," Nat. Mater, 9, 1023-1028. The above-cited disclosure is hereby incorporated by reference in its entirety.

In many embodiments, materials demonstrating asymmetric effective toughness are implemented. It has long been understood that the toughness of composite media can be anisotropic, i.e., the toughness can depend on the direction of propagation of the crack. The instant application shows that the toughness can also depend on the sense of propagation, and that this sense can be controlled. In effect, the state of stress at the crack tip depends not only on the location of the crack-tip and the tangent to the crack at the tip, but also on the position of the entire crack set.

The asymmetry of the crack propagation can be controlled in any of a variety of ways in accordance with embodiments of the invention. For example, in some embodiments, implemented materials are made to include an asymmetric distribution of elastic moduli. In numerous embodiments, implemented materials are made to include asymmetric inclusions. Each of these methodologies can be used to implement materials having asymmetric effective toughness in accordance with many embodiments of the invention.

Figure 18A:
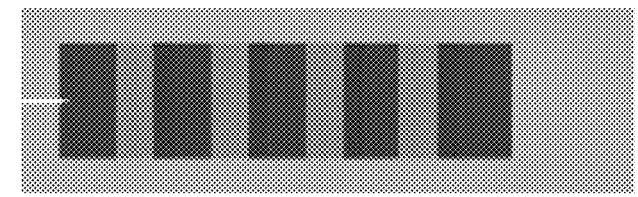
FIG. 18A-18C illustrate a material characterized by asymmetric elastic moduli in accordance with certain embodiments of the invention.
Figure 18A:
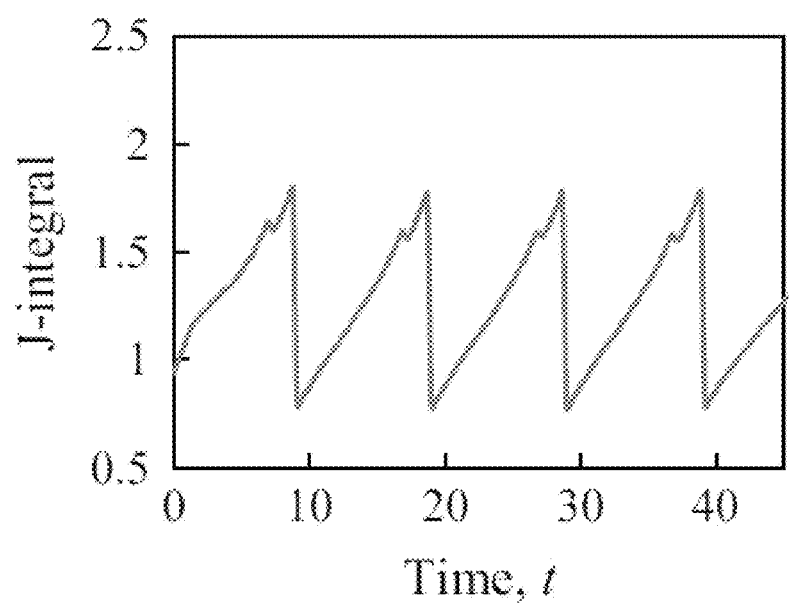
Figure 18B:
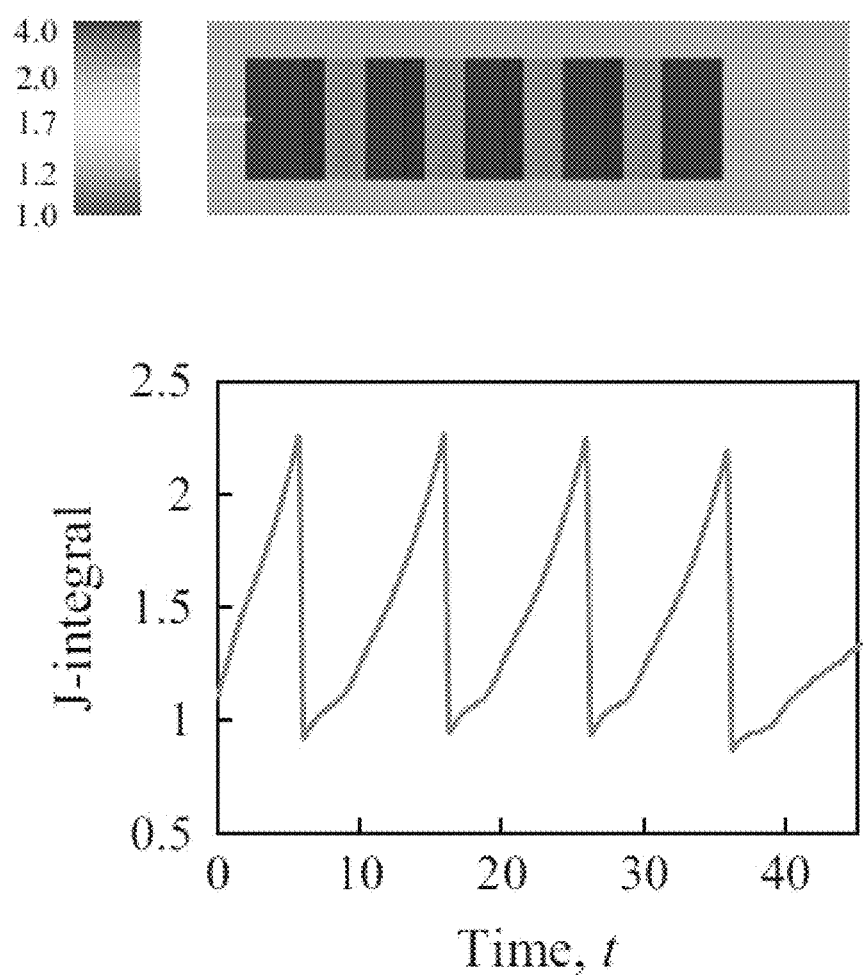
Figure 18C:
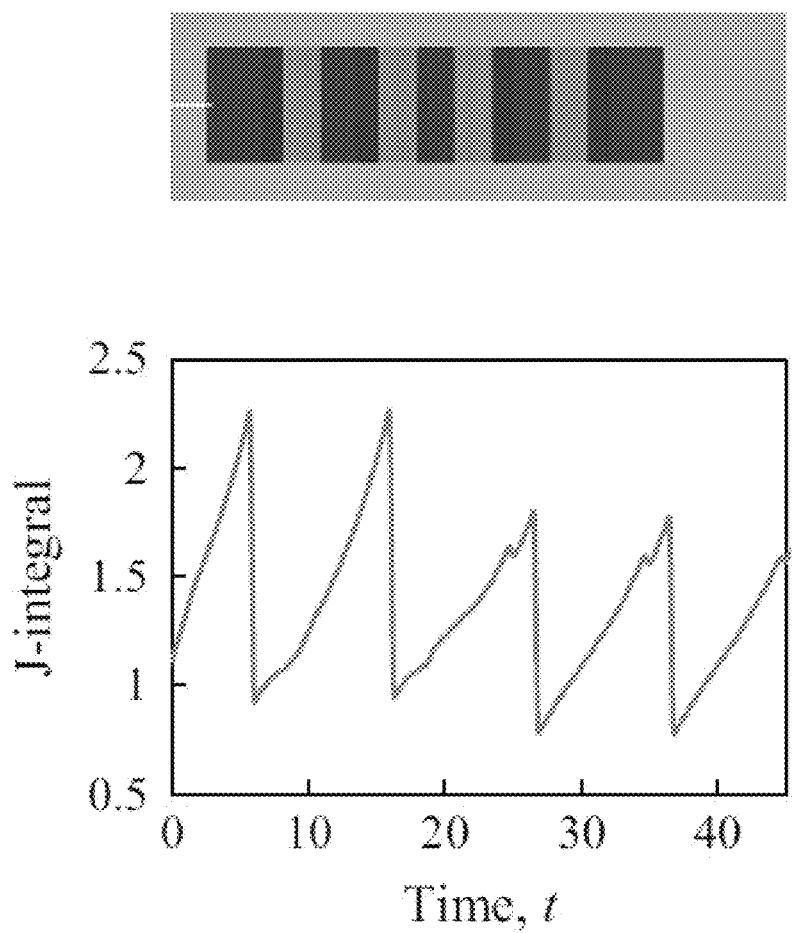

In one example, FIGS. 18A-18B illustrate a material including stripes with a periodic, but asymmetric, distribution of elastic moduli. In particular, FIG. 18A illustrates that the modulus rises in four gradual steps before dropping rapidly while the pattern is inverted in FIG. 18B. In other words, the two figures show the same asymmetric geometry, but flipped horizontally with respect to each other. The toughness is taken to be uniform. A crack introduced on the left of each geometry and driven to the right. Therefore, the two columns depict the crack being driven in opposite sense relative to the pattern. In both cases the crack propagates straight. However, the computed J for the two cases are quite different and not related by symmetry. In particular, the effective toughness is different in the two directions. To understand this, recall that the effective toughness in the previous example of stripes with alternating elastic moduli depends on the elastic contrast. In this example, the contrast going in one direction is different from that in the other direction. In short, effective toughness can be made to be asymmetric in accordance with many embodiments of the invention. FIG. 18C put the two modulations together in two halves, and it is seen that the two halves have different effective toughness.

Figure 19A:
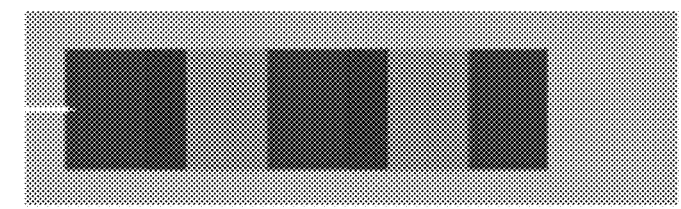
FIGS. 19A-19B illustrate a material characterized by asymmetric elastic moduli as well as increased strip width in accordance with certain embodiments of the invention.
Figure 19A:
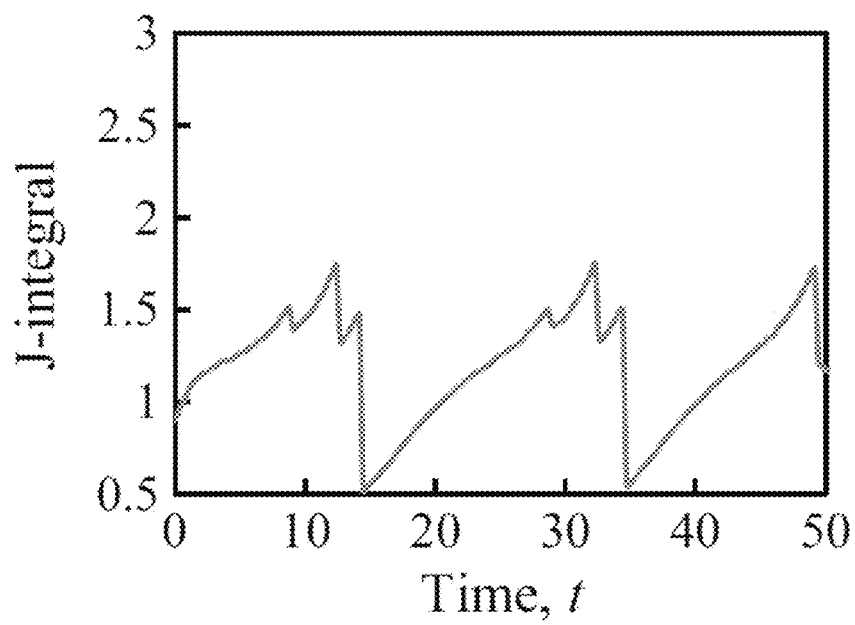
Figure 19B:
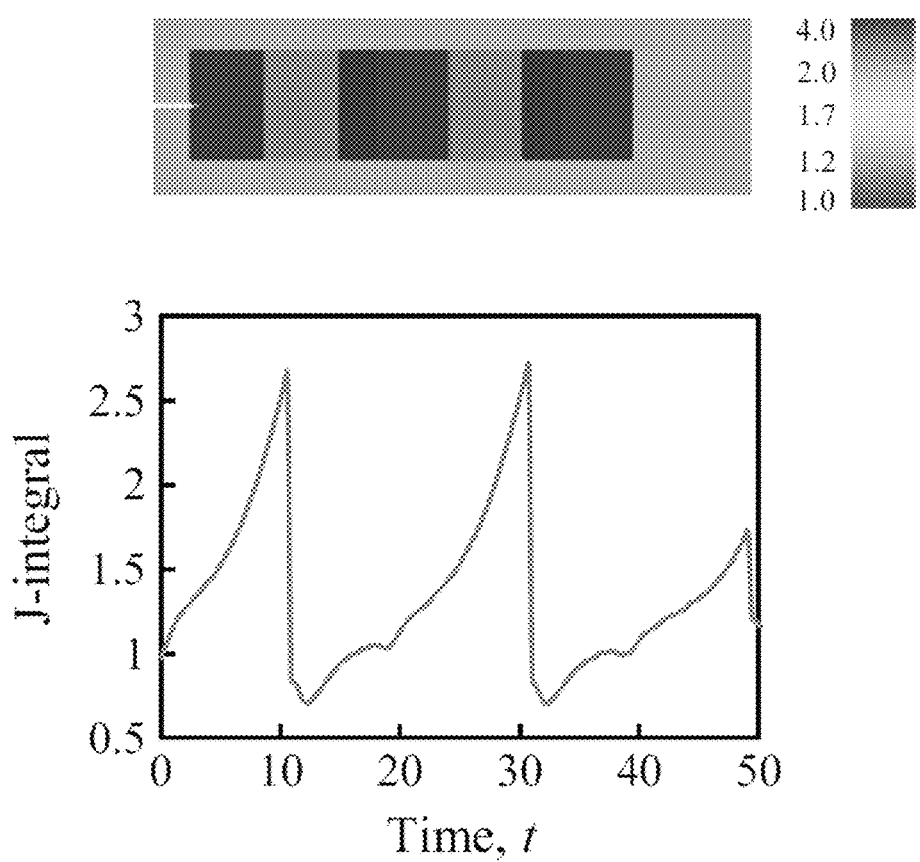

FIGS. 19A-19B repeats the example with increased strip width to find increased contrast. It is expected that the asymmetry vanishes as the length-scale decreases to the inherent length-scale of fracture, and to increase with increasing length-scale with an eventual saturation.

Figure 20A:
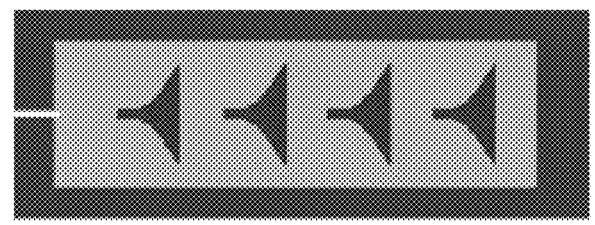
FIGS. 20A-20C illustrate the implementation of materials including asymmetric inclusions in accordance with certain embodiments of the invention.
Figure 20A:
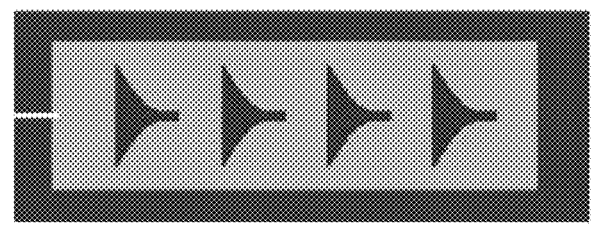
Figure 20B:
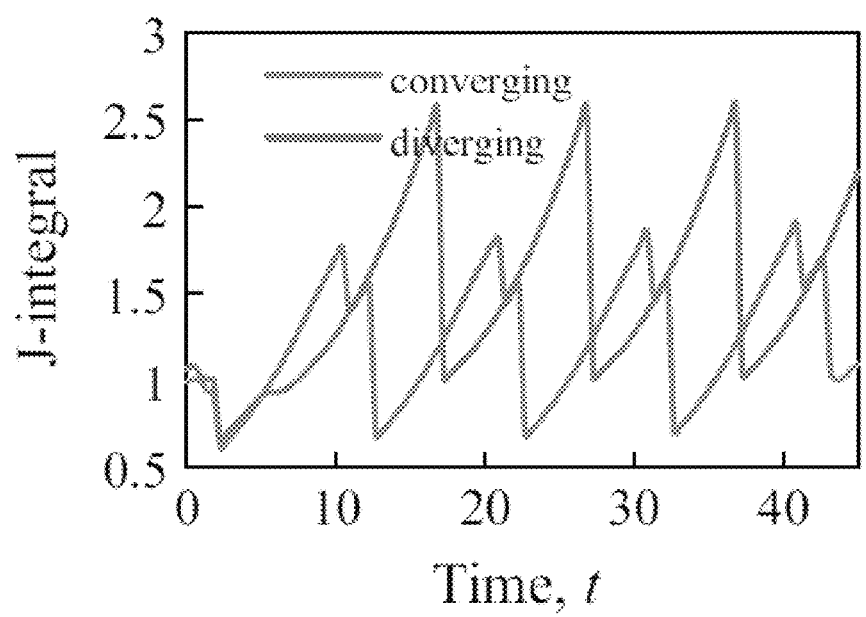
Figure 20C:
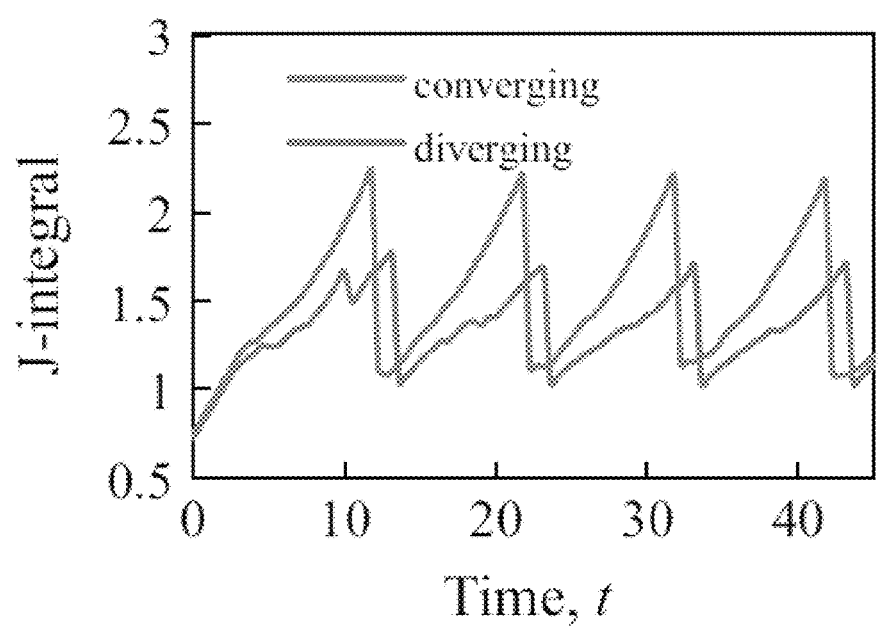
Figure 21A:
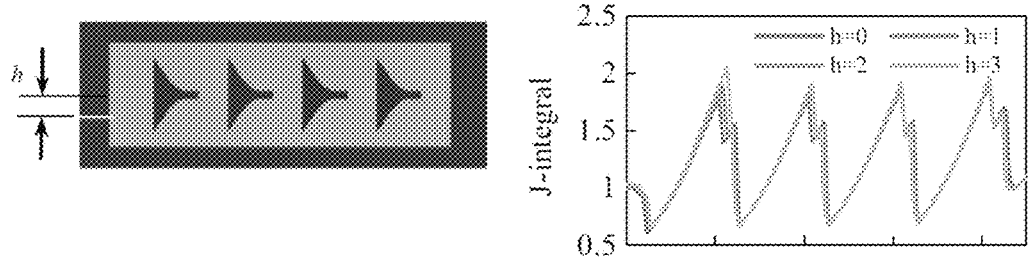
FIGS. 21A-21B illustrate the fracture mechanics pertaining to materials being characterized by asymmetric inclusions in certain situations in accordance with certain embodiments of the invention.
Figure 21B:
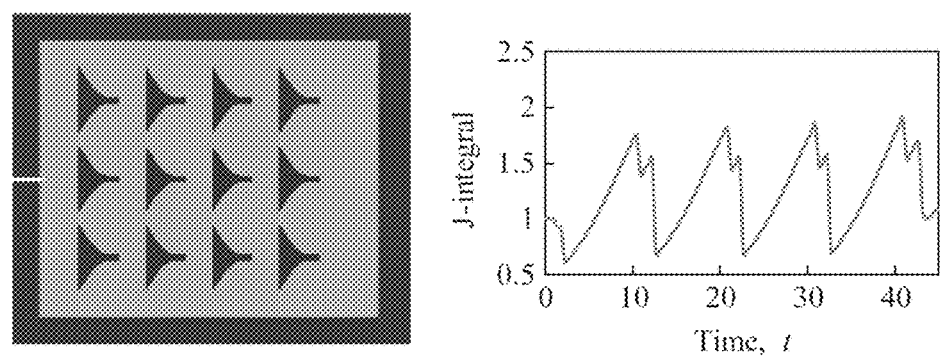

FIGS. 20A-20C illustrate the implementation of asymmetric inclusions within a material to thereby cause effective toughness asymmetry in accordance with many embodiments of the invention. In the illustrated embodiment, the toughness is again homogeneous. FIG. 20A shows the computational domain in two orientations. FIG. 20B shows the computed J vs. time as the crack propagates through the domain with compliant inclusions in a stiff matrix in two directions. The effective toughness is asymmetric. FIG. 20C shows the case of a domain with stiff inclusions in a compliant matrix. The effective toughness is asymmetric, but less than before. FIGS. 21A and 21B show that the computed results do not change if the initial crack is offset form the pattern, or if one has multiple rows of pattern so that the computed effective toughness represents a material rather than a structural property.

Figure 22A:
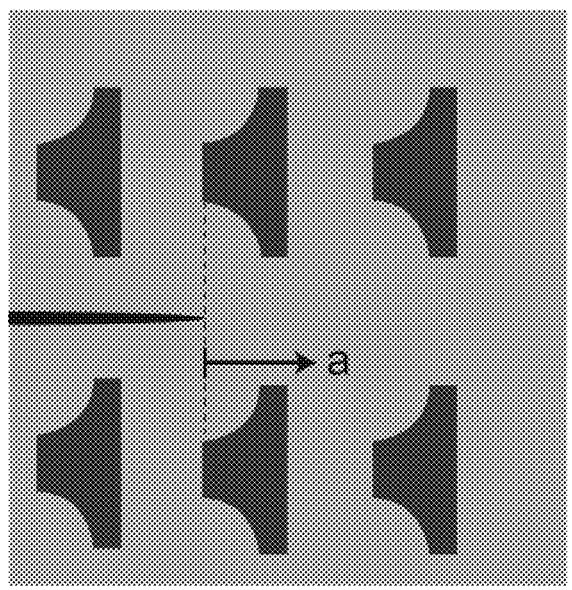
FIGS. 22A-22E illustrate crack propagation in between a symmetric row of asymmetric inclusions in accordance with certain embodiments of the invention.
Figure 22B:
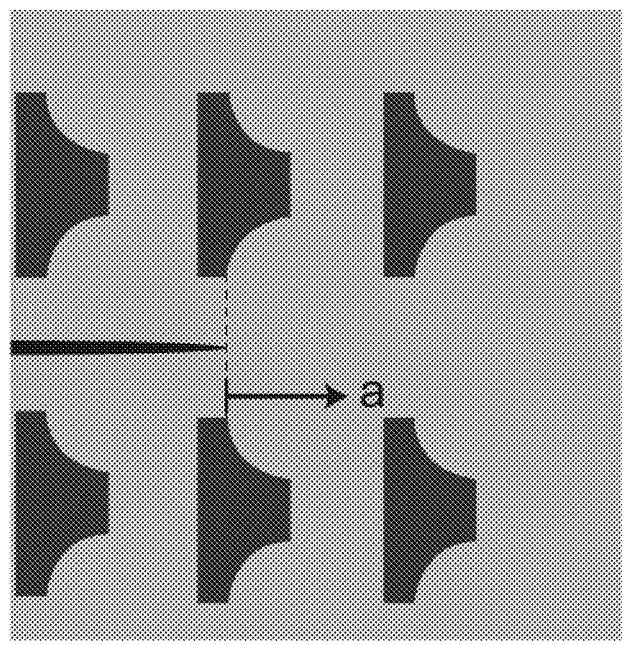
Figure 22C:
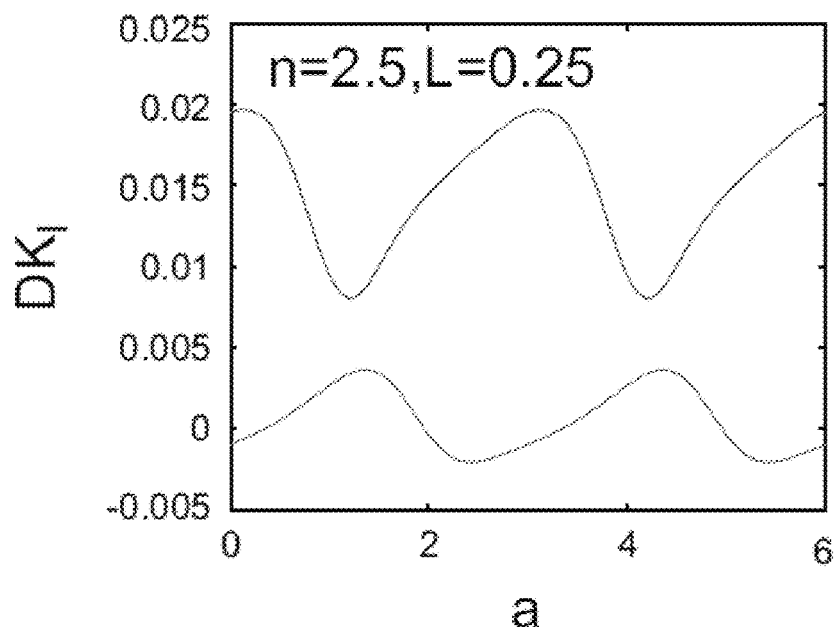
Figure 22D:
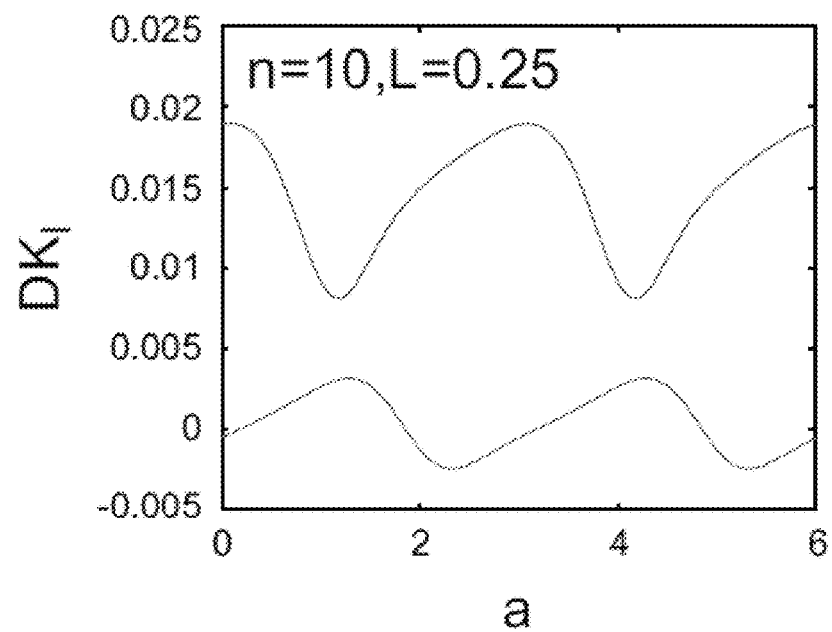
Figure 22E:
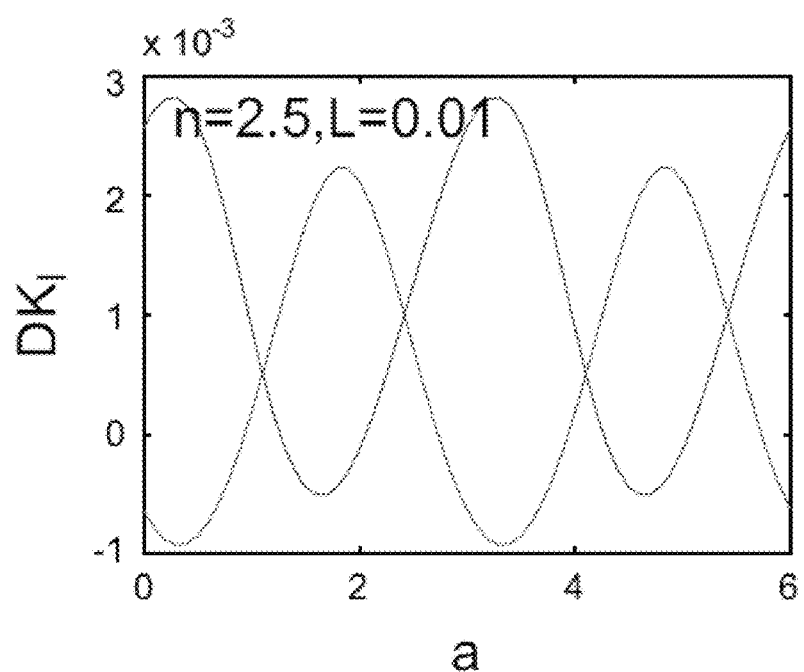

The simulations above are supplemented with semi-analytic calculations. In some instances, the computational method can have difficulty when the crack-tip touches the heterogeneity. So w a variant where the crack propagates between a symmetric row of inclusions is considered in FIGS. 22A-22E. Once again, the cracks are run in two opposite directions relative to the asymmetric pattern, and it is seen that there is a contrast in the resulting stress-intensity factor at the crack tip. The shape of the two curved regions are varied using various polynomial curves of the form $y=\pm(x-c_1)^n+c_0$ for various powers n, but this has little effect as shown in FIGS. 16C and 16D for n=2.5 and n=10. However, the width of the fat portion has an important effect as shown in FIG. 22C-22E for L=0.25 and L=0.1.

Figure 23:
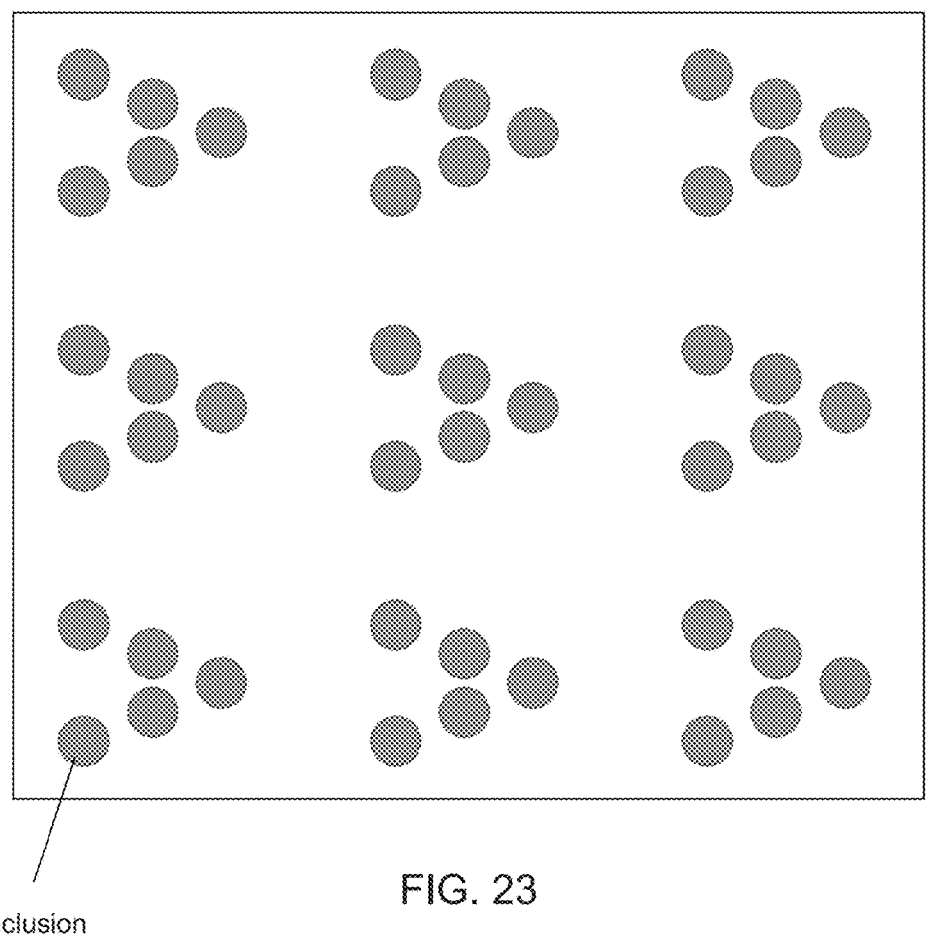
FIG. 23. illustrates a material including inclusions disbursed in an asymmetric arrangement so as to provoke asymmetric fracture characteristics in accordance with certain embodiments of the invention.

Note that while several of the examples have depicted materials including inclusions having an asymmetric geometry, which thereby give rise to asymmetric fracture characteristics, fracture characteristic asymmetry can be caused by any of a variety of microstructural architecture in accordance with embodiments of the invention. For example, in many embodiments, a material includes spherical inclusions in a pattern that gives rise to asymmetric fracture characteristics. Thus, for instance, FIG. 23 illustrates a material including spherical inclusions that are distributed in a periodic arrow pattern, which can thereby give rise to asymmetric fracture characteristics in accordance with embodiments of the invention. Of course, it should be appreciated that inclusions can be implemented and patterned in any of a variety of suitable ways to give rise to asymmetric fracture characteristics in accordance with many embodiments of the invention.

Figure 24A:
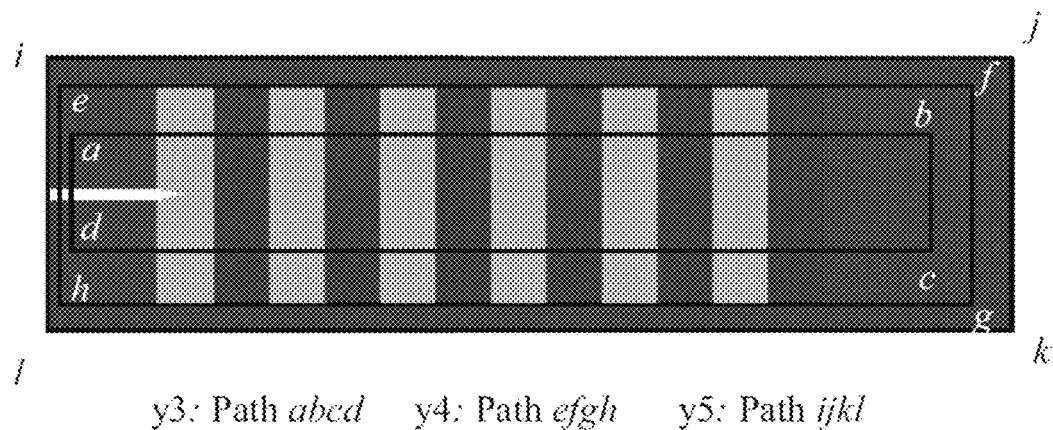
FIGS. 24A-24B illustrate the computation of a J-integral along three paths of a heterogeneous material embedded within a padded region in accordance with certain embodiments of the invention.
Figure 24B:
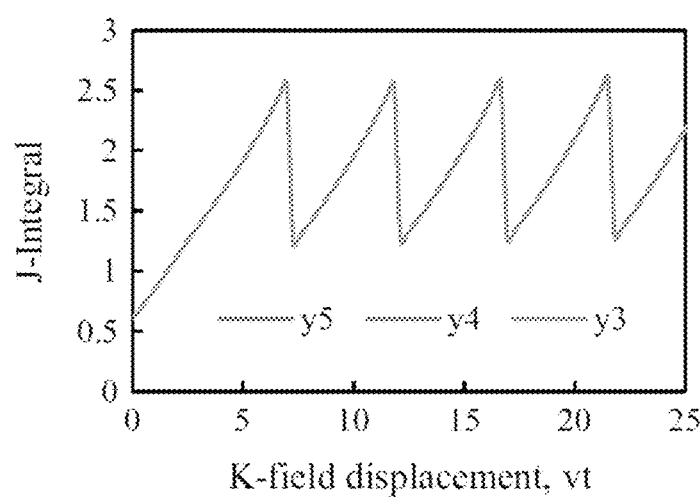

FIGS. 24A-24B further illustrate the viability of the disclosed methods. In particular, FIG. 24A illustrates the J-integral computed on three paths within a heterogeneous material that is within a padded region: at the outer boundary of the padded region, at the inner boundary of a padded region, and through the interior of the heterogeneous material. FIG. 24B illustrates how the first two paths agree exactly as one would expect, but so does the third.

These examples illustrate how the elastic heterogeneity and the fact that the state of stress is nonlocal, and thus depends on the entire crack set. It is emphasized that by noting that the examples have been modified by making the elastic moduli uniform but the effective toughness heterogeneous in an asymmetric manner. No asymmetry is seen since the effective toughness in both directions is determined by the maximum value of the pointwise toughness. Note that the development and implementation of materials having asymmetric fracture characteristics can have profound implications. For instance, by carefully developing such materials, the failure of a material can be controlled—e.g. if a material is at risk for failure, its implementation can be such that if and when it fails, at least the consequences can be reduced. While several examples have been given pertaining to implementing materials having asymmetric fracture characteristics, it should be clear that fracture asymmetry can be implemented in materials in any of a variety of ways in accordance with embodiments of the invention. For example, it should be clear that inclusions of any of a variety of suitable shapes can be incorporated in accordance with embodiments of the invention, not necessarily only those depicted in the above mentioned figures.

Methodologies for Fabricating Materials Having Tailored Toughness Characteristics While the above has discussion has largely focused on developing the notion of effective toughness, describing methodologies for evaluating the effective toughness, and describing the general structure of several materials possessing interesting toughness characteristics, many embodiments of the invention are directed to particularly effective methodologies for fabricating the above-described materials having interesting toughness characteristics. For example, in many embodiments, additive manufacturing technologies are used to fabricate such materials. For instance, the above description indicates how the toughness characteristics of a material can be tailored in interesting ways, but the tailoring generally requires precise control over the development of the microstructure (e.g. the development of precisely shaped inclusions, and/or the precise placement of inclusions within a material; and also the implementation of elastic heterogeneity within a material). Additive manufacturing technologies can allow these very precise structures to be so developed. While, additive manufacturing technologies have typically been implemented within the context of plastics, in many embodiments, such additive manufacturing techniques are implemented in the context of ceramics to develop ceramic materials having interesting toughness characteristics in accordance with the descriptions above. In other words, whereas material synthesis has traditionally largely been implemented in the context of fiber reinforced composites, laminated composites, porous materials, materials with random inclusions, acicular structures, etc., many embodiments of the invention regard the implementation of additive manufacture technologies to yield materials having the above-stated interesting toughness characteristics.

In many embodiments, the additive manufacture of the described materials is based on either: (1) oxide-void couples or (2) modulus mismatched oxide pairs. In many instances, the general additive manufacturing strategy for the material synthesis includes creating a sacrificial template around which a ceramic matrix is created; the sacrificial layer is then removed and either left as void or infiltrated with a second phase. As can be appreciated, the geometry, size and spacing of the templates will be an outgrowth of the theoretical models proposed above. For example, in a number of embodiments, the sacrificial template is developed so as to cause the implementation of geometrically asymmetric inclusions (e.g. funnel shaped inclusions)—as demonstrated above, such inclusions can give rise to materials having asymmetric effective toughness characteristics. Similarly, in a number of embodiments, the sacrificial template is developed so as to cause the implementation of inclusions disposed in an asymmetric arrangement (e.g. an 'arrow-shaped' pattern); as also demonstrated above, such a pattern can give rise to asymmetric effective toughness characteristics. Note also that although oxides are mentioned here, in many embodiments, nitrides and carbides can be similarly implemented. In other words, embodiments of the invention are not restricted to the implementation of oxides.

In many embodiments, the choice of processing methodologies relies on the ability to form a pattern with the desired fidelity while allowing for easy infiltration and densification of the ceramic matrix. In some instances, 2D microstructures are implemented, where the patterned inclusions are continuous through the thickness of the system. In numerous embodiments, 3D inclusion arrays are developed and designed as proposed above with respect to asymmetric inclusions. These printed patterns can be produced using photopolymers via commercially available polymer printing techniques. These can enable 100-micron resolution resulting in inclusions at the millimeter scale. Of course, it can be appreciated that the printed patterns can be produced using any of a variety of suitable techniques in accordance with embodiments of the invention. Note also that certain commercial printers having greater resolution can be used to implement inclusions on an even smaller scale. Additionally, in a number of embodiments, layer-by-layer stereolithography is used to synthesize the desired materials; in several embodiments, inkjet techniques are used. These techniques can offer significant range of possible feature sizes and resolutions, and can enable the implementation of inclusions on the order of microns to tens of microns.

In many embodiments, the implemented additive manufacturing strategies implement low viscosity materials that can easily flow around patterned voids. Importantly, these methods can also lend themselves to interface tailoring through deposition around patterns prior to matrix infiltration or down patterned holes.

Figure 25:
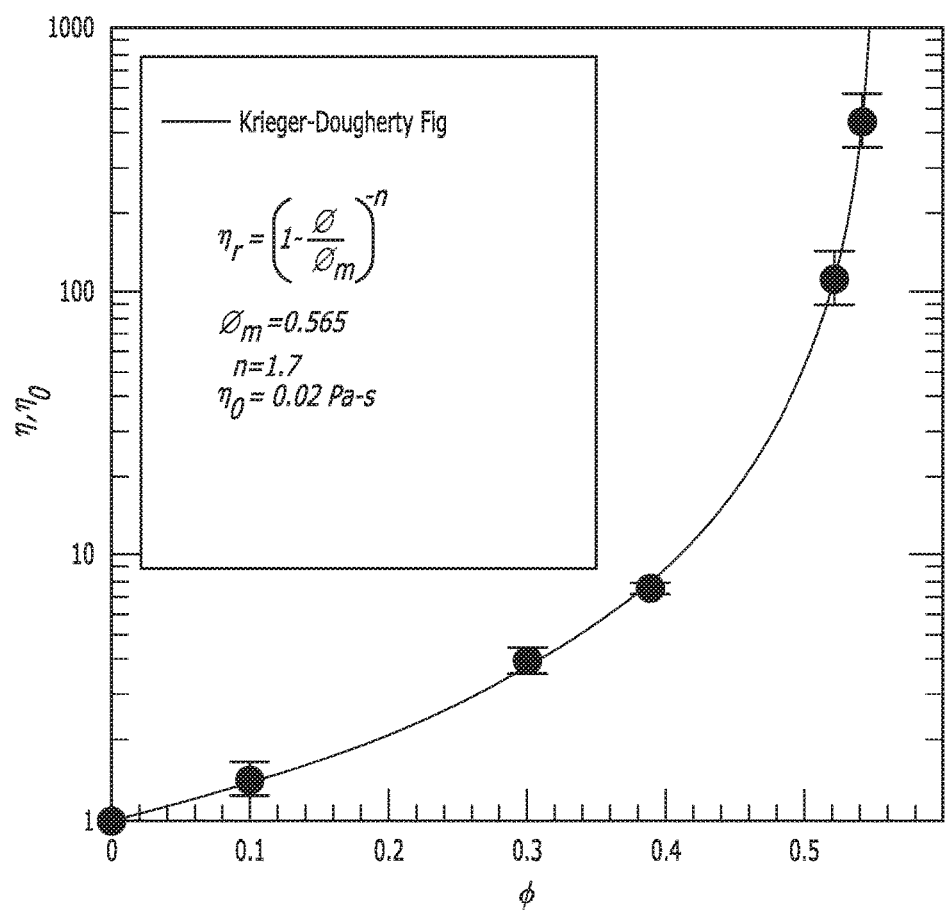
FIG. 25 illustrates viscosity characteristics for slurries that can be implemented in the additive manufacture of materials having tailored fracture characteristics in accordance with certain embodiments of the invention.

In many embodiments, 'gelcasting' is implemented to synthesize a desired material. In general, gelcasting involves the production of a low-viscosity slurry by mixing ceramic powders into a polymerizable monomer or thermoreversible gel. In both instances, the polymer serves as a vehicle for casting into the desired shape. The slurries can have characteristically high ceramic solids loading, often greater than 50% volume, but have sufficiently low viscosity for easy flow as shown in FIG. 25. Through the addition of a chemical initiator (or by changing the temperatures of the thermoreversible gels), a cross-linked network can be created, such that the filled gel, which has conformed to the shape of the pattern is rigid enough for further processing. The body can then be dried, taken to elevated temperature to remove the polymer network, and heated further for solid-state sintering of the remaining ceramic particles to achieve full density. Because typical gelcast bodies include high solids loadings, little shrinkage is expected on drying.

Many embodiments rely on the viscous flow of a low melting amorphous powder. For example, in a number of embodiments, a candidate powder is an $SnO_2$—$P_2O_5$ system, which is characterized by some of the lowest melting sealing glasses for the electronics industry. To create a dense solid, a glass powder suspension can be taken to temperatures in which viscous flow is activated (viscosities between $10^6$ and $10^8$ Pa-s). Densification rates at early stages are linear in time, and directly proportional to the surface energy, and inversely proportional to the glass viscosity and particle size.

Figure 26A:
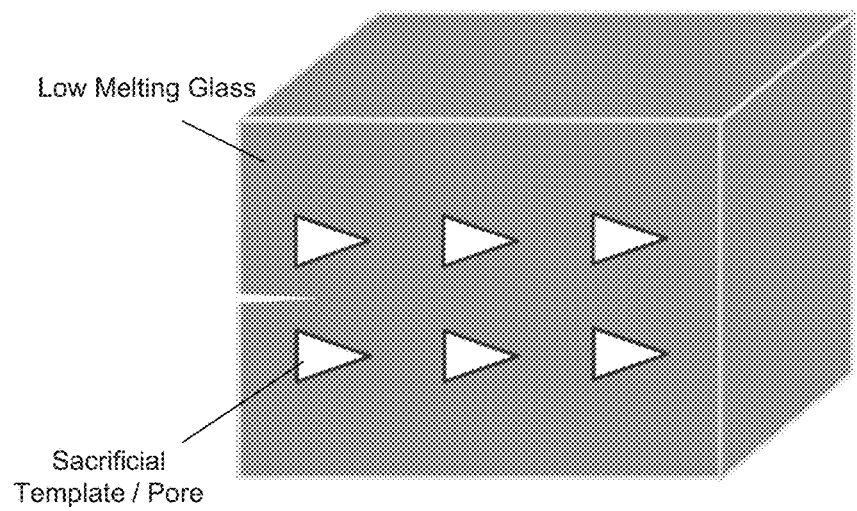
FIGS. 26A-26D illustrate various additive manufacturing strategies that can be used to fabricate materials having tailored fracture characteristics in accordance with certain embodiments of the invention.

FIGS. 26A-26D illustrates processing schemes that can be used to achieve desired mismatch pairs in accordance with embodiments of the invention. In particular, FIG. 26A illustrates a processing scheme for the situation where $E_1 \gg E_2$. In this scenario, it is depicted that the patterned inclusion can be a non-cylindrical pore ($E_2=0$). As can be appreciated, the patterns can be additively manufactured. In the as-printed state, a slurry of glass powder can infiltrate the network, and taken to a temperature where viscous flow is rapid. Once densified, the sacrificial template can phase can be removed by plasma etching, leaving a glass matrix with patterned pores.

Figure 26B:
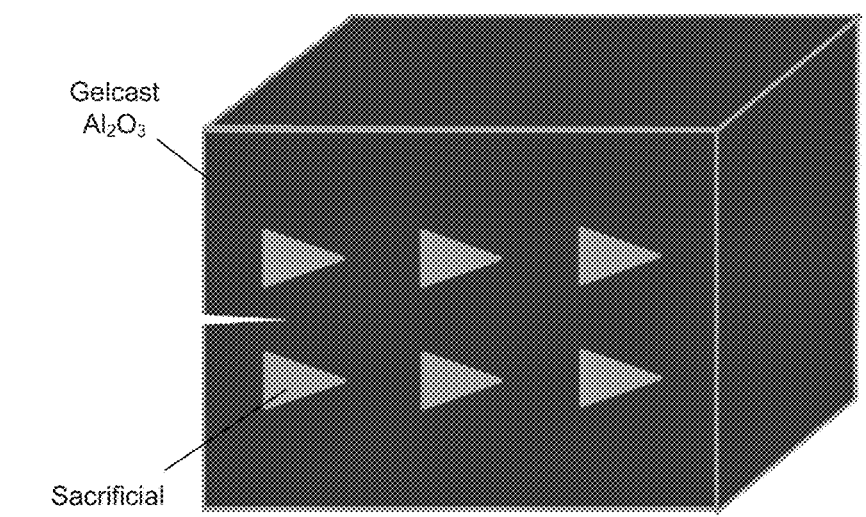

FIG. 26B illustrates a scenario for $E_1 > E_2$; in the illustrated embodiment, the matrix is instead produced by gelcasting $Al_2O_3$ ($E_1=400$ GPa), where heating commences with the sacrificial template in place. En route to the sintering temperature, the template volatilizes from the system, leaving in its place the patterned pore channel. Note that the shape of the sacrificial pores (carbon pores, starches, organic polymers) gelcast systems reproduce the shape of the porogen with great fidelity. In the illustrated embodiment, the channels can be back-filled with glass slurries and taken to temperature to achieve densification by viscous flow in the glassy phase. Given that flow and densification will take place within dense $Al_2O_3$, the work of Scherer and Garino who examined viscous sintering on rigid plates can be relied on; see e.g. G. W. Scherer and T. Garino, "Viscous sintering on a rigid substrate," *J. Am. Ceram. Soc.*, 68:216-220, 1985.

This above-cited disclosure is hereby incorporated by reference in its entirety. In many instances, the modulus mismatch in the final two-phase structure will be in the $30 < E_1/E_2 < 60$.

Figure 26C:
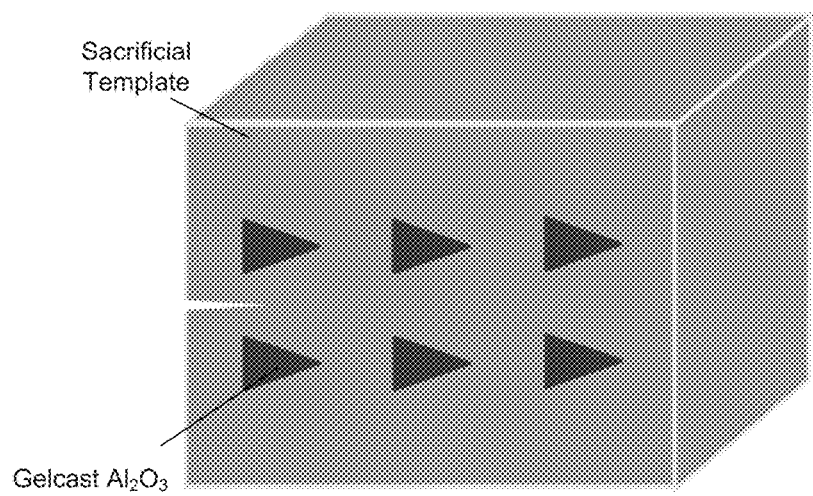

FIG. 26C illustrates the condition of $E_1 < E_2$; 3D printing is depended on to create the sacrificial matrix leaving patterned holes for infiltration. The patterned inclusions can be produced by gelcasting $Al_2O_3$, with the template matrix removed during the heating and sintering step. The template can be back-filled with a low melting glass slurry, as in the previous example. However, the glass now creates the low modulus matrix. In a number of instances, this process results in a modulus mismatch $E_1/E_2$ of between approximately 0.02 and approximately 0.03. Note that thermal mismatch stresses may influence crack growth.

Figure 26D:
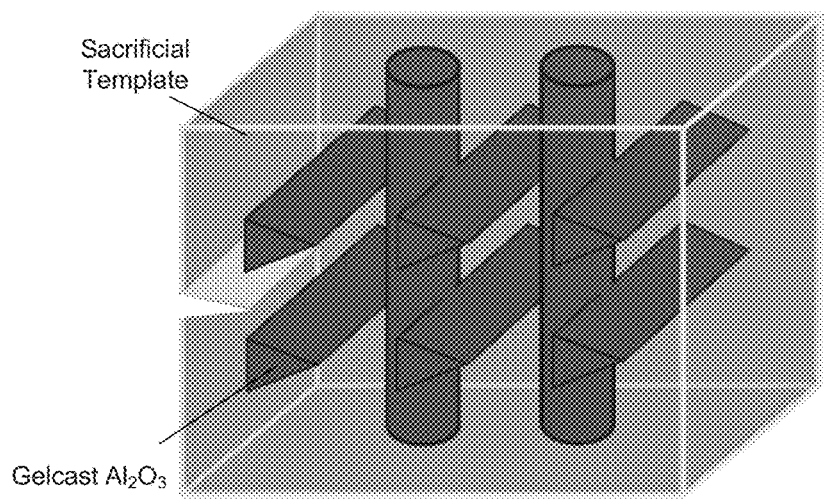

FIG. 26D illustrates that the sacrificial template can be additively manufactured to include patterned holes for infiltration.

Note that the interface fracture toughness can play a critical role in determining whether a crack will deflect along the inclusion or penetrate it. Interphases like BN or carbon provide interface toughnesses ($G_c^I$) less than 2 J/m$^2$, which promote crack deflection. In contrast, glass alumina interfaces have been measured as high as 15 J/m$^2$, which often result in crack penetration of the inclusion. The proposed 3D printing and casting strategies will allow deposition of interphases to alter interface toughnesses.

Figure 27:
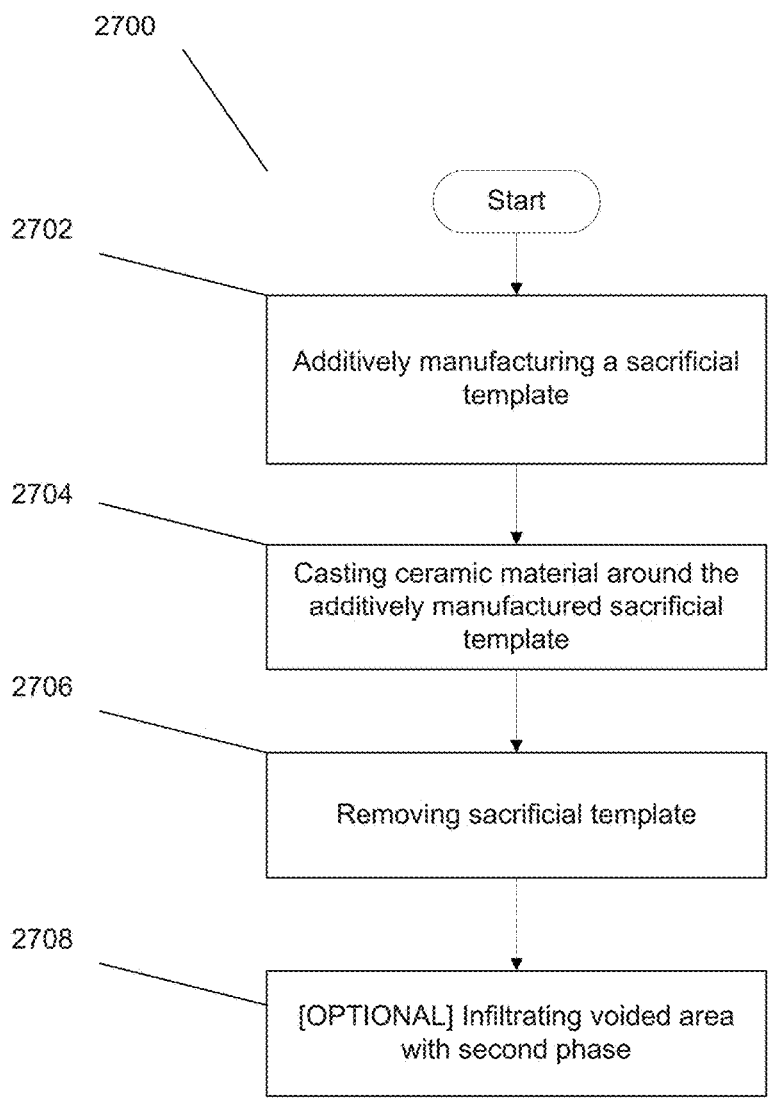
FIG. 27 illustrates a process for fabricating a material having desirable effective toughness characteristics in accordance with certain embodiments of the invention.

In accordance with the discussion above, FIG. 27 illustrates a generalized method for fabricating a material having desired effective toughness characteristics in accordance with many embodiments of the invention. In particular, the method 2700 includes additively manufacturing 2702 a sacrificial template. As can be appreciated, the sacrificial template can be additively manufactured so as to enable the implementation of inclusions within the materials that can give rise to desired asymmetric effective toughness characteristics, e.g. in accordance with the above discussion. For example, in many embodiments, the sacrificial template is configured to enable the implementation of inclusions being characterized by asymmetric geometries. In a number of embodiments, the sacrificial template is configured to enable the implementation of inclusions disposed within a material in an asymmetric arrangement. The method 2700 further includes casting 2704 ceramic material around the additively manufactured sacrificial template. Any of a variety of methodologies can be used to cast 2704 the ceramic material around the sacrificial template in accordance with many embodiments of the invention. For example, as can be appreciated from the discussion above, gelcasting methodologies can be used. In a number of embodiments, a ceramic material is cast using a low melting amorphous powder. To be clear, any suitable method can be implemented in accordance with many embodiments of the invention. The method 2700 further includes removing 2706 the sacrificial template. As can be appreciated, the sacrificial template can be removed using any suitable technique in accordance with many embodiments of the invention. For example, in some embodiments, plasma etching is used to remove the sacrificial template. Upon removal, the cast ceramic includes voids. The method 2700 optionally includes infiltrating the voided area 2708 with a second phase material. Any suitable second phase material can be implemented. In this way, a heterogeneous material having desired effective toughness characteristics can be implemented.

As can be inferred from the above discussion, the above-mentioned concepts can be implemented in a variety of arrangements in accordance with embodiments of the invention. Accordingly, although the present invention has been described in certain specific aspects, many additional modifications and variations would be apparent to those skilled in the art. It is therefore to be understood that the present invention may be practiced otherwise than specifically described. Thus, embodiments of the present invention should be considered in all respects as illustrative and not restrictive.

What is claimed is:

1. An elastically heterogeneous material comprising:
   at least a first region comprising a first material characterized by a first elastic modulus; and
   at least a second region comprising a second material characterized by a second elastic modulus, wherein:
   an elastic modulus ratio between the first elastic modulus and the second elastic modulus is greater than 2 or less than ½;
   the width and the length of each of the regions are greater than the length-scale of fracture of the material of said region; and the effective toughness of the elastically heterogeneous material is greater than if the material was characterized entirely by the toughness of the first material or by the toughness of the second material.

2. The elastically heterogeneous material of claim 1, wherein the elastically heterogeneous material is characterized by a plurality of adjacently-disposed regions characterized by striped geometries, wherein the elastic modulus of each of the regions alternates between the first elastic modulus and the second elastic modulus.

3. An elastically heterogeneous material comprising:
   a plurality of regions each comprising one of at least two different materials, each material being characterized by a different elastic modulus, such that the elastic modulus ratio between any two adjacent regions is greater than 2 or less than ½, wherein the width and the length of each of the regions are greater than the length-scale of fracture of the material of said region; and
   wherein the elastic moduli amongst the plurality of regions are asymmetrically distributed so as to give rise to a directionally asymmetric effective toughness of the elastically heterogeneous material.

4. The elastically heterogeneous material of claim 3, wherein the regions are characterized by striped geometries.

5. The elastically heterogeneous material of claim 4, wherein the elastically heterogeneous material is characterized by regions having a periodic, but asymmetric, distribution of different elastic moduli.

6. The elastically heterogeneous material of claim 5, wherein the distribution of elastic moduli includes at least one abrupt transition from low to high elastic modulus between regions and at least one tapered transition from low to high elastic modulus between regions.

7. The elastically heterogeneous material of claim 6, wherein the abrupt transition defined a difference in elastic modulus of at least a factor of 30.

8. The elastically heterogeneous material of claim 6, wherein the width of the regions with the lowest elastic modulus is larger than the widths of the remaining regions.

9. The elastically heterogeneous material of claim 3, further comprising connecting gaps between regions containing the material of either the first or second elastic modulus, wherein the connecting gaps between consecutive regions are offset such that a tortuous path is established during crack propagation.

10. An elastically heterogeneous material comprising:
    at least a first region comprising a first material characterized by a first elastic modulus;
    a plurality of inclusions comprised of a second material characterized by a second elastic modulus;
    wherein the inclusions comprise bodies having asymmetric geometries characterized by specific directionality; and
    wherein the presence of the inclusions causes the elastically heterogeneous material to have a directionally asymmetric effective toughness such that the effective toughness of the elastically heterogeneous material is greater than it would be if the material was entirely characterized only by the toughness of either the first or second materials alone.

11. The elastically heterogeneous material of claim 10, wherein the inclusions are arranged in a periodic array.

12. The elastically heterogeneous material of claim 11, wherein the inclusions are characterized by one of either arrow-shaped or funnel-shaped geometries, and wherein the inclusions are disposed in one of the following orientations:
    wherein the inclusions have a lower elastic modulus than the surrounding material in which they are disposed, and wherein the one of either arrow-shaped or funnel-shaped geometries of the inclusions are disposed in a diverging arrangement; and
    wherein the inclusions have a higher elastic modulus than the surrounding material in which they are disposed, and wherein the one of either arrow-shaped of funnel-shaped geometries of the inclusions are disposed in a converging arrangement.

13. The elastically heterogeneous material of claim 10, wherein the inclusions are disposed within the material in an asymmetric arrangement.

14. The elastically heterogeneous material of claim 13, wherein the inclusions are disposed within the material in one of either a funnel-shaped or an arrow-shaped pattern, wherein the inclusions are disposed in one of the following orientation
    wherein the inclusions have a lower elastic modulus than the surrounding material in which they are disposed, and wherein the one of either funnel-shaped or arrow-shaped geometries of the inclusions are disposed in a diverging arrangement; and
    wherein the inclusions have a higher elastic modulus than the surrounding material in which they are disposed, and wherein the one of either funnel-shaped or arrow-shaped geometries of the inclusions are disposed in a converging arrangement.

15. The elastically heterogeneous material of claim 10, wherein the inclusions are voids disposed within the first material.

16. The elastically heterogeneous material of claim 10, wherein the inclusions are microstructural architectures comprised of distinct inclusions distributed in a periodic directional pattern disposed in one of the following orientations:
    wherein the inclusions have a lower elastic modulus than the surrounding material in which they are disposed, and wherein the pattern of the inclusions are disposed in a diverging arrangement; and
    wherein the inclusions have a higher elastic modulus than the surrounding material in which they are disposed, and wherein the pattern of the inclusions are disposed in a converging arrangement.

* * * * *